(12) United States Patent
Harding et al.

(10) Patent No.: US 9,066,901 B2
(45) Date of Patent: *Jun. 30, 2015

(54) C-MET RECEPTOR REGULATION BY ANGIOTENSIN IV (AT4) RECEPTOR LIGANDS

(75) Inventors: Joseph W. Harding, Pullman, WA (US); John W. Wright, Pullman, WA (US); Patrick D. Elias, Pullman, WA (US); Brent J. Yamamoto, Pullman, WA (US); Leen H. Kawas, Pullman, WA (US)

(73) Assignee: Washington State University, Pullman, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/547,601

(22) Filed: Jul. 12, 2012

(65) Prior Publication Data

US 2013/0023475 A1 Jan. 24, 2013

Related U.S. Application Data

(63) Continuation-in-part of application No. 11/972,487, filed on Jan. 10, 2008, now Pat. No. 8,236,761, which is a continuation-in-part of application No. 11/774,517, filed on Jul. 6, 2007, now Pat. No. 7,910,555, and a continuation-in-part of application No. PCT/US2007/015572, filed on Jul. 6, 2007.

(60) Provisional application No. 60/819,201, filed on Jul. 7, 2006.

(51) Int. Cl.

| | |
|---|---|
| *A61K 38/22* | (2006.01) |
| *C07K 14/475* | (2006.01) |
| *A61K 38/00* | (2006.01) |
| *A61P 3/04* | (2006.01) |
| *A61P 25/00* | (2006.01) |
| *C07K 14/47* | (2006.01) |
| *A61K 38/08* | (2006.01) |
| *A61K 38/18* | (2006.01) |
| *C07K 14/705* | (2006.01) |
| *C07K 5/087* | (2006.01) |
| *C07K 5/09* | (2006.01) |
| *C07K 5/093* | (2006.01) |
| *C07K 5/103* | (2006.01) |
| *C07K 5/11* | (2006.01) |
| *C07K 5/113* | (2006.01) |
| *G01N 33/50* | (2006.01) |
| *G01N 33/68* | (2006.01) |
| *C07K 5/107* | (2006.01) |
| *C07K 5/083* | (2006.01) |
| *C07K 5/065* | (2006.01) |
| *C07K 5/072* | (2006.01) |
| *C07K 5/062* | (2006.01) |
| *C07K 5/068* | (2006.01) |

(52) U.S. Cl.
CPC ........... *A61K 38/085* (2013.01); *A61K 38/1833* (2013.01); *C07K 14/705* (2013.01); *C07K 5/0812* (2013.01); *C07K 5/0815* (2013.01); *C07K 5/0819* (2013.01); *C07K 5/101* (2013.01); *C07K 5/1019* (2013.01); *C07K 5/1021* (2013.01); *G01N 33/502* (2013.01); *G01N 33/5023* (2013.01); *G01N 33/6893* (2013.01); *G01N 2800/044* (2013.01); *C07K 5/0817* (2013.01); *C07K 5/1016* (2013.01); *C07K 5/0808* (2013.01); *C07K 5/06078* (2013.01); *C07K 5/06095* (2013.01); *C07K 5/06034* (2013.01); *C07K 5/06086* (2013.01); *C07K 5/06113* (2013.01)

(58) Field of Classification Search
CPC ............. A61K 38/085; A61K 38/1833; C07K 14/705; C07K 5/0812; C07K 5/0815; C07K 5/0819; C07K 5/101; C07K 5/1019; C07K 5/1021; C07K 5/0817; C07K 5/1016; C07K 5/0808; C07K 5/06113; C07K 5/06086; C07K 5/06034; C07K 5/06095; C07K 5/06078; G01N 33/502; G01N 33/5023; G01N 33/6893; G01N 2800/044

See application file for complete search history.

(56) References Cited

U.S. PATENT DOCUMENTS

2002/0147129 A1* 10/2002 Mendelsohn et al. ............ 514/2

OTHER PUBLICATIONS

Kawas et al "Mimics of the Dimerization Domain of Hepatocyte Growth Factor Exhibit Anti-Met and Anticancer Activity" J Pharm and Exp Ther 339:509-518. Published online Aug. 22, 2011.*
Kawas et al "Development of angiotensin IV analogs as hepatocyte growth factor/Met modifiers" J Pharm and Exp Ther 340:539-548.*
Masino, J Alexander "Identification of the angiotensin IV receptor antagonist, norleual, as a novel inhibitor of angiogenesis and tumor growth" Dissertation. University of Washington. UMI Number: 3096890. Published May 2003.*
Wright and Harding "Brain renin-angiotensin—A new look at an old system" Progress in Neurobiology 95:49-67. Published online Jul. 13, 2011.*
Grammatopoulos T "Angiotensin II protects against a-synuclein toxicity and reduces protein aggregation in vitro" Biochem Biophys Res Comm 363:846-851. Published Sep. 12, 2007.*
Yamamoto et al "The Angiotensin IV Analog Nle-Tyr-Leu-psi-(CH2-NH2)3-4-His-Pro-Phe (Norleual) Can Act as a Hepatocyte Growth Factor/c-Met Inhibitor" J Pharmacol Exper Ther 333:161-173. Published online Jan. 19, 2010.*
McCoy A "Pharmacokinetic Characterization of Angiotensin IV Analogs with Therapeutic Potential for Cancer and Dementia" Dissertation. Published May 2010.*
Kadoyama et al. "Therapeutic Potential of Hepatocyte Growth Factor for Treating Neurological Diseases" Current Drug Therapy 6:197-206. Published 2011.*
"Neurologic Diseases" MedlinePlus. Accessed on Internet at <www.nlm.nih.gov/medlineplus/neurologicdiseases.html>. Originally published 2003.*

* cited by examiner

*Primary Examiner* — James H Alstrum Acevedo
*Assistant Examiner* — Zachary J Miknis
(74) *Attorney, Agent, or Firm* — Whitham Curtis Christofferson & Cook, PC

(57) ABSTRACT

Angiotensin-like factor compositions and methods for using them to diagnose, prevent and/or treat conditions associated with c-Met dysregulation, are provided. The conditions include cancer, obesity, conditions associated with obesity, and neurodegenerative diseases such as general dementia, Alzheimer's disease, Parkinson's disease, Amyotrophic Lateral Sclerosis, traumatic brain injury and spinal cord trauma.

8 Claims, 29 Drawing Sheets

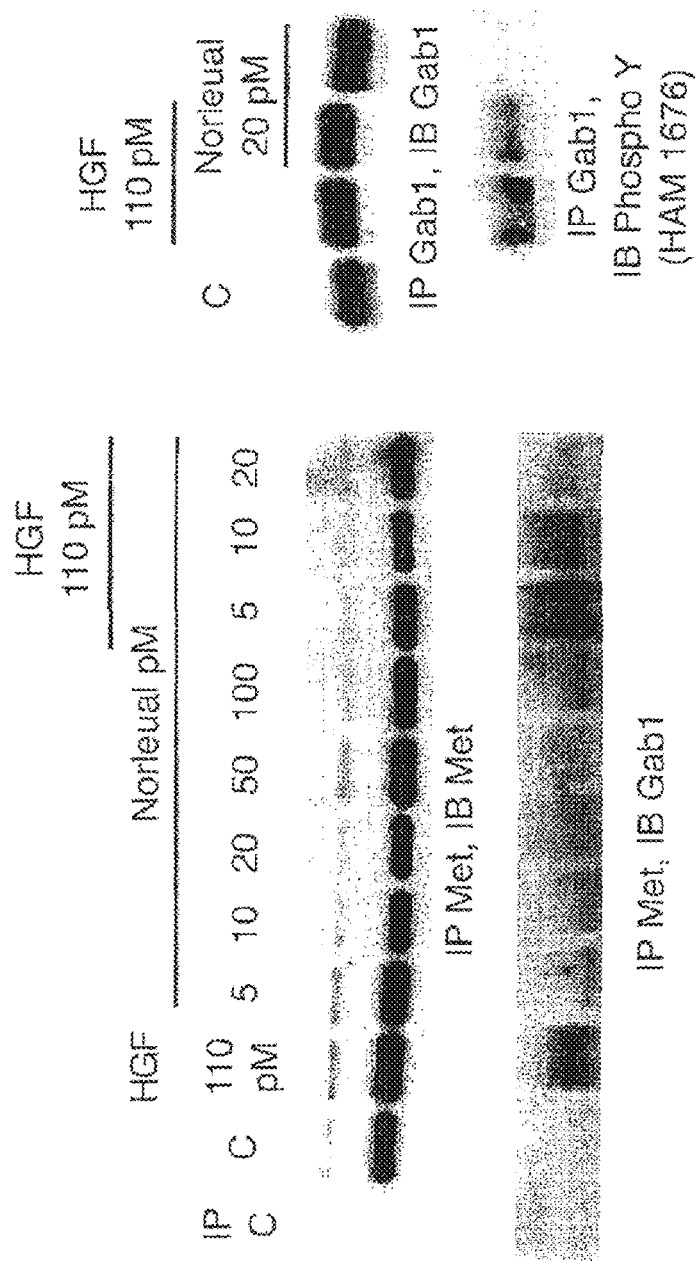

SEQUENCE LISTING

<160> NUMBER OF SEQ ID NOS: 141

<210> SEQ ID NO 1
<211> LENGTH: 7
<212> TYPE: PRT
<213> ORGANISM: Homo sapiens

<400> SEQUENCE: 1

Leu Asp Tyr Ile Arg Asn Cys
 1               5

<210> SEQ ID NO 2
<211> LENGTH: 728
<212> TYPE: PRT
<213> ORGANISM: Homo sapiens

<400> SEQUENCE: 2

Met Trp Val Thr Lys Leu Leu Pro Ala Leu Leu Leu Gln His Val Leu
 1               5                  10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile

```
305                 310                 315                 320
Trp Asn Gly Ile Pro Cys Gln Arg Trp Asp Ser Gln Tyr Pro His Glu
                325                 330                 335
His Asp Met Thr Pro Glu Asn Phe Lys Cys Lys Asp Leu Arg Glu Asn
                340                 345                 350
Tyr Cys Arg Asn Pro Asp Gly Ser Glu Ser Pro Trp Cys Phe Thr Thr
                355                 360                 365
Asp Pro Asn Ile Arg Val Gly Tyr Cys Ser Gln Ile Pro Asn Cys Asp
        370                 375                 380
Met Ser His Gly Gln Asp Cys Tyr Arg Gly Asn Gly Lys Asn Tyr Met
385                 390                 395                 400
Gly Asn Leu Ser Gln Thr Arg Ser Gly Leu Thr Cys Ser Met Trp Asp
                405                 410                 415
Lys Asn Met Glu Asp Leu His Arg His Ile Phe Trp Glu Pro Asp Ala
                420                 425                 430
Ser Lys Leu Asn Glu Asn Tyr Cys Arg Asn Pro Asp Asp Ala His
                435                 440                 445
Gly Pro Trp Cys Tyr Thr Gly Asn Pro Leu Ile Pro Trp Asp Tyr Cys
        450                 455                 460
Pro Ile Ser Arg Cys Glu Gly Asp Thr Thr Pro Thr Ile Val Asn Leu
465                 470                 475                 480
Asp His Pro Val Ile Ser Cys Ala Lys Thr Lys Gln Leu Arg Val Val
                485                 490                 495
Asn Gly Ile Pro Thr Arg Thr Asn Ile Gly Trp Met Val Ser Leu Arg
                500                 505                 510
Tyr Arg Asn Lys His Ile Cys Gly Gly Ser Leu Ile Lys Glu Ser Trp
                515                 520                 525
Val Leu Thr Ala Arg Gln Cys Phe Pro Ser Arg Asp Leu Lys Asp Tyr
        530                 535                 540
Glu Ala Trp Leu Gly Ile His Asp Val His Gly Arg Gly Asp Glu Lys
545                 550                 555                 560
Cys Lys Gln Val Leu Asn Val Ser Gln Leu Val Tyr Gly Pro Glu Gly
                565                 570                 575
Ser Asp Leu Val Leu Met Lys Leu Ala Arg Pro Ala Val Leu Asp Asp
                580                 585                 590
Phe Val Ser Thr Ile Asp Leu Pro Asn Tyr Gly Cys Thr Ile Pro Glu
                595                 600                 605
Lys Thr Ser Cys Ser Val Tyr Gly Trp Gly Tyr Thr Gly Leu Ile Asn
        610                 615                 620
Tyr Asp Gly Leu Leu Arg Val Ala His Leu Tyr Ile Met Gly Asn Glu
625                 630                 635                 640
Lys Cys Ser Gln His His Arg Gly Lys Val Thr Leu Asn Glu Ser Glu
                645                 650                 655
Ile Cys Ala Gly Ala Glu Lys Ile Gly Ser Gly Pro Cys Glu Gly Asp
                660                 665                 670
Tyr Gly Gly Pro Leu Val Cys Glu Gln His Lys Met Arg Met Val Leu
        675                 680                 685
Gly Val Ile Val Pro Gly Arg Gly Cys Ala Ile Pro Asn Arg Pro Gly
        690                 695                 700
Ile Phe Val Arg Val Ala Tyr Tyr Ala Lys Trp Ile His Lys Ile Ile
705                 710                 715                 720
Leu Thr Tyr Lys Val Pro Gln Ser
                725
```

<210> SEQ ID NO 3
<211> LENGTH: 696
<212> TYPE: PRT
<213> ORGANISM: Pan Troglodytes

<400> SEQUENCE: 3

```
Met Trp Val Thr Lys Leu Leu Pro Ala Leu Leu Gln His Val Leu
 1               5                  10                  15

Leu His Leu Leu Leu Pro Ile Ala Ile Pro Tyr Ala Glu Gly Gln
             20                  25                  30

Arg Lys Arg Asn Thr Ile His Glu Phe Lys Lys Ser Ala Lys Thr
             35                  40                  45

Thr Leu Ile Lys Ile Asp Pro Ala Leu Lys Ile Lys Thr Lys Lys Val
 50                  55                  60

Asn Thr Ala Asp Gln Cys Ala Asn Arg Cys Thr Arg Asn Lys Gly Leu
 65                  70                  75                  80

Pro Phe Thr Cys Lys Ala Phe Val Phe Asp Lys Ala Arg Lys Gln Cys
                 85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Gly His Glu Thr Phe Gly
                115                 120                 125

Arg Phe Leu Pro Ser Ser Tyr Arg Gly Lys Asp Leu Gln Glu Asn Tyr
130                 135                 140

Cys Arg Asn Pro Arg Gly Glu Glu Gly Gly Pro Trp Cys Phe Thr Ser
145                 150                 155                 160

Asn Pro Glu Val Arg Tyr Glu Val Cys Asp Ile Pro Gln Cys Ser Glu
                165                 170                 175

Val Glu Cys Met Thr Cys Asn Gly Glu Ser Tyr Arg Gly Leu Met Asp
                180                 185                 190

His Thr Glu Ser Gly Lys Ile Cys Gln Arg Trp Asp His Gln Thr Pro
                195                 200                 205

His Arg His Lys Phe Leu Pro Glu Arg Tyr Pro Asp Lys Gly Phe Asp
210                 215                 220

Asp Asn Tyr Cys Arg Asn Pro Asp Gly Gln Pro Arg Pro Trp Cys Tyr
225                 230                 235                 240

Thr Leu Asp Pro His Thr Arg Trp Glu Tyr Cys Ala Ile Lys Thr Cys
                245                 250                 255

Ala Asp Asn Thr Met Asn Asp Thr Asp Val Pro Leu Glu Thr Thr Glu
                260                 265                 270

Cys Ile Gln Gly Gln Gly Glu Gly Tyr Arg Gly Thr Val Asn Thr Ile
                275                 280                 285

Trp Asn Gly Ile Pro Cys Gln Arg Trp Asp Ser Gln Tyr Pro His Glu
290                 295                 300

His Asp Met Thr Pro Glu Asn Phe Lys Cys Lys Asp Leu Arg Glu Asn
305                 310                 315                 320

Tyr Cys Arg Asn Pro Asp Gly Ser Glu Ser Pro Trp Cys Phe Thr Thr
                325                 330                 335

Asp Pro Asn Ile Arg Val Gly Tyr Cys Ser Gln Ile Pro Asn Cys Asp
                340                 345                 350

Met Ser His Gly Gln Asp Cys Tyr Arg Gly Asn Gly Lys Asn Tyr Met
                355                 360                 365

Gly Asn Leu Ser Gln Thr Arg Ser Gly Leu Thr Cys Ser Met Trp Asp
```

```
                    370                 375                 380
Lys Asn Met Glu Asp Leu His Arg His Ile Phe Trp Glu Pro Asp Ala
385                 390                 395                 400

Ser Lys Leu Asn Glu Asn Tyr Cys Arg Asn Pro Asp Asp Ala His
                405                 410                 415

Gly Pro Trp Cys Tyr Thr Gly Asn Pro Leu Ile Pro Trp Asp Tyr Cys
                420                 425                 430

Pro Ile Ser Arg Cys Glu Gly Asp Thr Thr Pro Thr Ile Val Asn Leu
                435                 440                 445

Asp His Pro Val Ile Ser Cys Ala Lys Thr Lys Gln Leu Arg Val Val
            450                 455                 460

Asn Gly Ile Pro Thr Arg Thr Asn Val Gly Trp Met Val Ser Leu Arg
465                 470                 475                 480

Tyr Arg Asn Lys His Ile Cys Gly Gly Ser Leu Ile Lys Glu Ser Trp
                485                 490                 495

Val Leu Thr Ala Arg Gln Cys Phe Pro Ser Arg Asp Leu Lys Asp Tyr
                500                 505                 510

Glu Ala Trp Leu Gly Ile His Asp Val His Gly Arg Gly Asp Glu Lys
                515                 520                 525

Cys Lys Gln Val Leu Asn Val Ser Gln Leu Val Tyr Gly Pro Glu Gly
                530                 535                 540

Ser Asp Leu Val Leu Met Lys Leu Ala Arg Pro Ala Val Leu Asp Asp
545                 550                 555                 560

Phe Val Ser Thr Ile Asp Leu Pro Asn Tyr Gly Cys Thr Ile Pro Glu
                565                 570                 575

Lys Thr Ser Cys Ser Val Tyr Gly Trp Gly Tyr Thr Gly Leu Ile Asn
                580                 585                 590

Tyr Asp Gly Leu Leu Arg Val Ala His Leu Tyr Ile Met Gly Asn Glu
                595                 600                 605

Lys Cys Ser Gln His His Arg Gly Lys Val Thr Leu Asn Glu Ser Glu
                610                 615                 620

Ile Cys Ala Gly Ala Glu Lys Ile Gly Ser Gly Pro Cys Glu Gly Asp
625                 630                 635                 640

Tyr Gly Gly Pro Leu Val Cys Glu Gln His Lys Met Arg Met Val Leu
                645                 650                 655

Gly Val Ile Val Pro Gly Arg Gly Cys Ala Ile Pro Asn Arg Pro Gly
                660                 665                 670

Ile Phe Val Arg Val Ala Tyr Tyr Ala Lys Trp Ile His Lys Ile Ile
                675                 680                 685

Leu Thr Tyr Lys Val Pro Gln Ser
690                 695

<210> SEQ ID NO 4
<211> LENGTH: 728
<212> TYPE: PRT
<213> ORGANISM: Mus musculus

<400> SEQUENCE: 4

Met Met Trp Gly Thr Lys Leu Leu Pro Val Leu Leu Leu Gln His Val
1               5                   10                  15

Leu Leu His Leu Leu Leu Leu His Val Ala Ile Pro Tyr Ala Glu Gly
                20                  25                  30

Gln Lys Lys Arg Arg Asn Thr Leu His Glu Phe Lys Lys Ser Ala Lys
                35                  40                  45
```

-continued

```
Thr Thr Leu Thr Lys Glu Asp Pro Leu Leu Lys Ile Lys Thr Lys Lys
    50                  55                  60

Val Asn Ser Ala Asp Glu Cys Ala Asn Arg Cys Ile Arg Asn Arg Gly
 65             70                  75                  80

Phe Thr Phe Thr Cys Lys Ala Phe Val Phe Asp Lys Ser Arg Lys Arg
                 85                  90                  95

Cys Tyr Trp Tyr Pro Phe Asn Ser Met Ser Ser Gly Val Lys Lys Gly
                100                 105                 110

Phe Gly His Glu Phe Asp Leu Tyr Glu Asn Lys Asp Tyr Ile Arg Asn
            115                 120                 125

Cys Ile Ile Gly Lys Gly Gly Ser Tyr Lys Gly Thr Val Ser Ile Thr
    130                 135                 140

Lys Ser Gly Ile Lys Cys Gln Pro Trp Asn Ser Met Ile Pro His Glu
145                 150                 155                 160

His Ser Phe Leu Pro Ser Ser Tyr Arg Gly Lys Asp Leu Gln Glu Asn
                165                 170                 175

Tyr Cys Arg Asn Pro Arg Gly Glu Glu Gly Pro Trp Cys Phe Thr
                180                 185                 190

Ser Asn Pro Glu Val Arg Tyr Glu Val Cys Asp Ile Pro Gln Cys Ser
            195                 200                 205

Glu Val Glu Cys Met Thr Cys Asn Gly Glu Ser Tyr Arg Gly Pro Met
    210                 215                 220

Asp His Thr Glu Ser Gly Lys Thr Cys Gln Arg Trp Asp Gln Gln Thr
225                 230                 235                 240

Pro His Arg His Lys Phe Leu Pro Glu Arg Tyr Pro Asp Lys Gly Phe
                245                 250                 255

Asp Asp Asn Tyr Cys Arg Asn Pro Asp Gly Lys Pro Arg Pro Trp Cys
                260                 265                 270

Tyr Thr Leu Asp Pro Asp Thr Thr Trp Glu Tyr Cys Ala Ile Lys Thr
            275                 280                 285

Cys Ala His Ser Ala Val Asn Glu Thr Asp Val Pro Met Glu Thr Thr
    290                 295                 300

Glu Cys Ile Gln Gly Gln Gly Glu Gly Tyr Arg Gly Thr Ser Asn Thr
305                 310                 315                 320

Ile Trp Asn Gly Ile Pro Cys Gln Arg Trp Asp Ser Gln Tyr Pro His
                325                 330                 335

Lys His Asp Ile Thr Pro Glu Asn Phe Lys Cys Lys Asp Leu Arg Glu
            340                 345                 350

Asn Tyr Cys Arg Asn Pro Asp Gly Ala Glu Ser Pro Trp Cys Phe Thr
    355                 360                 365

Thr Asp Pro Asn Ile Arg Val Gly Tyr Cys Ser Gln Ile Pro Lys Cys
370                 375                 380

Asp Val Ser Ser Gly Gln Asp Cys Tyr Arg Gly Asn Gly Lys Asn Tyr
                385                 390                 395                 400

Met Gly Asn Leu Ser Lys Thr Arg Ser Gly Leu Thr Cys Ser Met Trp
                405                 410                 415

Asp Lys Asn Met Glu Asp Leu His Arg His Ile Phe Trp Glu Pro Asp
            420                 425                 430

Ala Ser Lys Leu Asn Lys Asn Tyr Cys Arg Asn Pro Asp Asp Asp Ala
    435                 440                 445

His Gly Pro Trp Cys Tyr Thr Gly Asn Pro Leu Ile Pro Trp Asp Tyr
    450                 455                 460

Cys Pro Ile Ser Arg Cys Glu Gly Asp Thr Thr Pro Thr Ile Val Asn
```

```
            465                 470                 475                 480
Leu Asp His Pro Val Ile Ser Cys Ala Lys Thr Lys Gln Leu Arg Val
                    485                 490                 495
Val Asn Gly Ile Pro Thr Gln Thr Thr Val Gly Trp Met Val Ser Leu
                500                 505                 510
Lys Tyr Arg Asn Lys His Ile Cys Gly Gly Ser Leu Ile Lys Glu Ser
            515                 520                 525
Trp Val Ile Thr Ala Arg Gln Cys Phe Pro Ala Arg Asn Lys Asp Leu
        530                 535                 540
Lys Asp Tyr Glu Ala Trp Leu Gly Ile His Asp Val His Glu Arg Gly
545                 550                 555                 560
Glu Glu Lys Arg Lys Gln Ile Leu Asn Ile Ser Gln Leu Val Tyr Gly
                565                 570                 575
Pro Glu Gly Ser Asp Leu Val Leu Leu Lys Leu Ala Arg Pro Ala Ile
            580                 585                 590
Leu Asp Asn Phe Val Ser Thr Ile Asp Leu Pro Ser Tyr Gly Cys Thr
        595                 600                 605
Ile Pro Glu Lys Thr Thr Cys Ser Ile Tyr Gly Trp Gly Tyr Thr Gly
    610                 615                 620
Leu Ile Asn Ala Asp Gly Leu Leu Arg Val Ala His Leu Tyr Ile Met
625                 630                 635                 640
Gly Asn Glu Lys Cys Ser Gln His His Gln Gly Lys Val Thr Leu Asn
                645                 650                 655
Glu Ser Glu Leu Cys Ala Gly Ala Glu Lys Ile Gly Ser Gly Pro Cys
            660                 665                 670
Glu Gly Asp Tyr Gly Gly Pro Leu Ile Cys Glu Gln His Lys Met Arg
        675                 680                 685
Met Val Leu Gly Val Ile Val Pro Gly Arg Gly Cys Ala Ile Pro Asn
        690                 695                 700
Arg Pro Val Ile Phe Val Arg Val Ala Tyr Tyr Ala Lys Trp Ile His
705                 710                 715                 720
Lys Val Ile Leu Thr Tyr Lys Leu
                725

<210> SEQ ID NO 5
<211> LENGTH: 728
<212> TYPE: PRT
<213> ORGANISM: Rattus norvegicus

<400> SEQUENCE: 5

Met Met Trp Gly Thr Lys Leu Leu Pro Val Leu Leu Leu Gln His Val
1               5                   10                  15
Leu Leu His Leu Leu Leu Leu Pro Val Thr Ile Pro Tyr Ala Glu Gly
                20                  25                  30
Gln Lys Lys Arg Arg Asn Thr Leu His Glu Phe Lys Lys Ser Ala Lys
            35                  40                  45
Thr Thr Leu Thr Lys Glu Asp Pro Leu Val Lys Ile Lys Thr Lys Lys
        50                  55                  60
Val Asn Ser Ala Asp Glu Cys Ala Asn Arg Cys Ile Arg Asn Lys Gly
65                  70                  75                  80
Phe Pro Phe Thr Cys Lys Ala Phe Val Phe Asp Lys Ser Arg Lys Arg
                85                  90                  95
Cys Tyr Trp Tyr Pro Phe Asn Ser Met Ser Ser Gly Val Lys Lys Gly
                100                 105                 110
```

-continued

```
Phe Gly His Glu Phe Asp Leu Tyr Glu Asn Lys Asp Tyr Ile Arg Asn
            115                 120                 125

Cys Ile Ile Gly Lys Gly Ser Tyr Lys Gly Thr Val Ser Ile Thr
130                 135                 140

Lys Ser Gly Ile Lys Cys Gln Pro Trp Asn Ser Met Ile Pro His Glu
145                 150                 155                 160

His Ser Phe Leu Pro Ser Ser Tyr Arg Gly Lys Asp Leu Gln Glu Asn
                165                 170                 175

Tyr Cys Arg Asn Pro Arg Gly Glu Glu Gly Gly Pro Trp Cys Phe Thr
            180                 185                 190

Ser Asn Pro Glu Val Arg Tyr Glu Val Cys Asp Ile Pro Gln Cys Ser
            195                 200                 205

Glu Val Glu Cys Met Thr Cys Asn Gly Glu Ser Tyr Arg Gly Pro Met
210                 215                 220

Asp His Thr Glu Ser Gly Lys Thr Cys Gln Arg Trp Asp Gln Gln Thr
225                 230                 235                 240

Pro His Arg His Lys Phe Leu Pro Glu Arg Tyr Pro Asp Lys Gly Phe
                245                 250                 255

Asp Asp Asn Tyr Cys Arg Asn Pro Asp Gly Lys Pro Arg Pro Trp Cys
            260                 265                 270

Tyr Thr Leu Asp Pro Asp Thr Pro Trp Glu Tyr Cys Ala Ile Lys Met
            275                 280                 285

Cys Ala His Ser Ala Val Asn Glu Thr Asp Val Pro Met Glu Thr Thr
290                 295                 300

Glu Cys Ile Lys Gly Gln Gly Glu Gly Tyr Arg Gly Thr Thr Asn Thr
305                 310                 315                 320

Ile Trp Asn Gly Ile Pro Cys Gln Arg Trp Asp Ser Gln Tyr Pro His
                325                 330                 335

Lys His Asp Ile Thr Pro Glu Asn Phe Lys Cys Lys Asp Leu Arg Glu
            340                 345                 350

Asn Tyr Cys Arg Asn Pro Asp Gly Ala Glu Ser Pro Trp Cys Phe Thr
            355                 360                 365

Thr Asp Pro Asn Ile Arg Val Gly Tyr Cys Ser Gln Ile Pro Lys Cys
370                 375                 380

Asp Val Ser Ser Gly Gln Asp Cys Tyr Arg Gly Asn Gly Lys Asn Tyr
385                 390                 395                 400

Met Gly Asn Leu Ser Lys Thr Arg Ser Gly Leu Thr Cys Ser Met Trp
                405                 410                 415

Asp Lys Asn Met Glu Asp Leu His Arg His Ile Phe Trp Glu Pro Asp
            420                 425                 430

Ala Ser Lys Leu Thr Lys Asn Tyr Cys Arg Asn Pro Asp Asp Asp Ala
            435                 440                 445

His Gly Pro Trp Cys Tyr Thr Gly Asn Pro Leu Val Pro Trp Asp Tyr
450                 455                 460

Cys Pro Ile Ser Arg Cys Glu Gly Asp Thr Thr Pro Thr Ile Val Asn
465                 470                 475                 480

Leu Asp His Pro Val Ile Ser Cys Ala Lys Thr Lys Gln Leu Arg Val
                485                 490                 495

Val Asn Gly Ile Pro Thr Gln Thr Thr Val Gly Trp Met Val Ser Leu
            500                 505                 510

Lys Tyr Arg Asn Lys His Ile Cys Gly Gly Ser Leu Ile Lys Glu Ser
            515                 520                 525

Trp Val Leu Thr Ala Arg Gln Cys Phe Pro Ala Arg Asn Lys Asp Leu
```

```
                530                 535                 540
Lys Asp Tyr Glu Ala Trp Leu Gly Ile His Asp Val His Glu Arg Gly
545                 550                 555                 560

Glu Glu Lys Arg Lys Gln Ile Leu Asn Ile Ser Gln Leu Val Tyr Gly
                565                 570                 575

Pro Glu Gly Ser Asp Leu Val Leu Leu Lys Leu Ala Arg Pro Ala Ile
                580                 585                 590

Leu Asp Asn Phe Val Ser Thr Ile Asp Leu Pro Ser Tyr Gly Cys Thr
                595                 600                 605

Ile Pro Glu Lys Thr Thr Cys Ser Ile Tyr Gly Trp Gly Tyr Thr Gly
                610                 615                 620

Leu Ile Asn Ala Asp Gly Leu Leu Arg Val Ala His Leu Tyr Ile Met
625                 630                 635                 640

Gly Asn Glu Lys Cys Ser Gln His His Gln Gly Lys Val Thr Leu Asn
                645                 650                 655

Glu Ser Glu Leu Cys Ala Gly Ala Glu Lys Ile Gly Ser Gly Pro Cys
                660                 665                 670

Glu Gly Asp Tyr Gly Gly Pro Leu Ile Cys Glu Gln His Lys Met Arg
                675                 680                 685

Met Val Leu Gly Val Ile Val Pro Gly Arg Gly Cys Ala Ile Pro Asn
                690                 695                 700

Arg Pro Gly Ile Phe Val Arg Val Ala Tyr Tyr Ala Lys Trp Ile His
705                 710                 715                 720

Lys Val Ile Leu Thr Tyr Lys Leu
                725

<210> SEQ ID NO 6
<211> LENGTH: 730
<212> TYPE: PRT
<213> ORGANISM: Canis familiaris

<400> SEQUENCE: 6

Met Trp Val Thr Lys Leu Leu Pro Leu Leu Val Leu Gln Gln Leu Leu
1               5                   10                  15

Leu His Leu Leu Leu Pro Val Ala Val Pro Arg Ala Glu Gly Gln
                20                  25                  30

Lys Lys Arg Arg Asn Thr Leu His Glu Phe Lys Lys Ser Ala Lys Thr
                35                  40                  45

Thr Leu Ile Lys Glu Asp Pro Leu Leu Lys Ile Lys Thr Lys Lys Met
50                  55                  60

Asn Thr Ala Asp Gln Cys Ala Asn Arg Cys Ile Arg Asn Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Thr Ser Gly Val Lys Lys Glu Phe
                100                 105                 110

Gly His Glu Phe Asp Leu Tyr Glu Asn Lys Asp Tyr Ile Arg Asn Cys
                115                 120                 125

Ile Ile Gly Lys Gly Gly Ser Tyr Lys Gly Thr Val Ser Ile Thr Lys
                130                 135                 140

Ser Gly Ile Lys Cys Gln Pro Trp Asn Ser Met Ile Pro His Glu His
145                 150                 155                 160

Ser Phe Leu Pro Ser Ser Tyr Arg Gly Lys Asp Leu Gln Glu Asn Tyr
                165                 170                 175
```

```
Cys Arg Asn Pro Arg Gly Glu Glu Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Pro Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Lys Pro Arg Pro Trp Cys Tyr
            260                 265                 270

Thr Leu Asp Pro Asp Thr Pro Trp Glu Tyr Cys Ala Ile Lys Met Cys
        275                 280                 285

Ala His Ser Thr Met Asn Asp Thr Asp Val Pro Met Glu Thr Thr Glu
    290                 295                 300

Cys Ile Gln Gly Gln Gly Glu Gly Tyr Arg Gly Thr Ile Asn Thr Ile
305                 310                 315                 320

Trp Asn Gly Val Pro Cys Gln Arg Trp Asp Ser Gln Tyr Pro His Gln
                325                 330                 335

His Asp Ile Thr Pro Glu Asn Phe Lys Cys Lys Asp Leu Arg Glu Asn
            340                 345                 350

Tyr Cys Arg Asn Pro Asp Gly Ala Glu Ser Pro Trp Cys Phe Thr Thr
        355                 360                 365

Asp Pro Asn Ile Arg Val Gly Tyr Cys Ser Gln Ile Pro Lys Cys Asp
    370                 375                 380

Val Ser Ser Gly Gln Asp Cys Tyr Arg Gly Asn Gly Lys Asn Tyr Met
385                 390                 395                 400

Gly Asn Leu Ser Lys Thr Arg Ser Gly Leu Thr Cys Ser Met Trp Glu
                405                 410                 415

Lys Asn Met Glu Asp Leu His Arg His Ile Phe Trp Glu Pro Asp Ala
            420                 425                 430

Ser Lys Leu Asn Lys Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Phe Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Val Gly Trp Met Val Ser Leu Lys
            500                 505                 510

Tyr Arg Asn Lys His Ile Cys Gly Gly Ser Leu Ile Lys Glu Ser Trp
        515                 520                 525

Ile Leu Thr Ala Arg Gln Cys Phe Pro Ser Arg Asn Arg Asp Leu Lys
    530                 535                 540

Asp Tyr Glu Ala Trp Leu Gly Ile His Asp Val His Gly Lys Gly Asp
545                 550                 555                 560

Glu Lys Arg Lys Gln Val Leu Asn Val Ser Gln Leu Val Tyr Gly Pro
                565                 570                 575

Glu Gly Ser Asp Leu Val Leu Leu Lys Leu Ala Arg Pro Ala Ile Leu
            580                 585                 590

Asp Asp Phe Val Ser Thr Ile Asp Leu Pro Asn Tyr Gly Cys Thr Ile
```

```
                    595                 600                 605
Pro Glu Lys Thr Thr Cys Ser Val Tyr Gly Trp Gly Tyr Thr Gly Ser
610                 615                 620

Ile Asn Phe Asp Gly Leu Leu Arg Val Ala His Leu Tyr Ile Met Gly
625                 630                 635                 640

Asn Glu Lys Cys Ser Gln Tyr His Gln Gly Lys Val Thr Leu Asn Glu
                645                 650                 655

Ser Glu Ile Cys Ala Gly Ala Glu Asn Ile Val Ser Gly Pro Cys Glu
            660                 665                 670

Gly Asp Tyr Gly Gly Pro Leu Val Cys Glu Gln His Lys Met Arg Met
        675                 680                 685

Val Leu Gly Val Ile Val Pro Gly Arg Gly Cys Ala Ile Pro Asn Arg
690                 695                 700

Pro Gly Ile Phe Val Arg Val Ala Tyr Tyr Ala Lys Trp Ile His Lys
705                 710                 715                 720

Ile Ile Leu Thr Tyr Lys Ile Gln Gln Ser
                725                 730

<210> SEQ ID NO 7
<211> LENGTH: 728
<212> TYPE: PRT
<213> ORGANISM: Felis catus

<400> SEQUENCE: 7

Met Trp Val Thr Lys Leu Leu Pro Val Leu Leu Gln His Val Leu
 1               5                  10                  15

Leu His Leu Leu Leu Pro Ile Pro Tyr Ala Glu Gly Gln Lys Lys
                20                  25                  30

Arg Arg Asn Thr Leu His Glu Phe Lys Lys Ser Ala Lys Thr Thr Leu
                35                  40                  45

Ile Lys Glu Asp Pro Leu Leu Lys Ile Lys Thr Lys Lys Met Asn Thr
 50                  55                  60

Ala Asp Gln Cys Ala Asn Arg Cys Ile Arg Asn Lys Gly Leu Pro Phe
65                   70                  75                  80

Thr Cys Lys Ala Phe Val Phe Asp Lys Ala Arg Lys Arg Cys Leu Trp
                85                  90                  95

Phe Pro Phe Asn Ser Met Thr Ser Gly Val Lys Lys Glu Phe Gly His
                100                 105                 110

Glu Phe Asp Leu Tyr Glu Asn Lys Asp Tyr Ile Arg Asn Cys Ile Ile
                115                 120                 125

Gly Lys Gly Gly Ser Tyr Lys Gly Thr Val Ser Ile Thr Lys Ser Gly
            130                 135                 140

Ile Lys Cys Gln Pro Trp Asn Ser Met Ile Pro His Glu His Ser Phe
145                 150                 155                 160

Leu Pro Ser Ser Tyr Arg Gly Lys Asp Leu Gln Glu Asn Tyr Cys Arg
                165                 170                 175

Asn Pro Arg Gly Glu Glu Gly Gly Pro Trp Cys Phe Thr Ser Asn Pro
                180                 185                 190

Glu Val Arg Tyr Glu Val Cys Asp Ile Pro Gln Cys Ser Glu Val Glu
                195                 200                 205

Cys Met Thr Cys Asn Gly Glu Ser Tyr Arg Gly Pro Met Asp His Thr
            210                 215                 220

Glu Ser Gly Lys Ile Cys Gln Arg Trp Asp Arg Gln Thr Pro His Arg
225                 230                 235                 240
```

-continued

```
His Lys Phe Leu Pro Glu Arg Tyr Pro Asp Lys Gly Phe Asp Asn
                245                 250                 255

Tyr Cys Arg Asn Pro Asp Gly Lys Pro Arg Pro Trp Cys Tyr Thr Leu
            260                 265                 270

Asp Pro Asp Thr Pro Trp Glu Tyr Cys Ala Ile Lys Met Cys Ala His
        275                 280                 285

Ser Thr Met Asn Asp Thr Asp Val Pro Met Glu Thr Thr Glu Cys Ile
    290                 295                 300

Gln Gly Gln Gly Glu Gly Tyr Arg Gly Thr Ile Asn Ser Ile Trp Asn
305                 310                 315                 320

Gly Val Pro Cys Gln Arg Trp Asp Ser Gln Tyr Pro His Gln His Asp
                325                 330                 335

Ile Thr Pro Glu Asn Phe Lys Cys Lys Asp Leu Arg Glu Asn Phe Cys
            340                 345                 350

Arg Asn Pro Asp Gly Ala Glu Ser Pro Trp Cys Phe Thr Thr Asp Pro
        355                 360                 365

Asn Ile Arg Val Gly Tyr Cys Ser Gln Ile Pro Lys Cys Asp Val Ser
    370                 375                 380

Ser Gly Gln Asp Cys Tyr Arg Gly Asn Gly Lys Asn Tyr Met Gly Asn
385                 390                 395                 400

Leu Ser Lys Thr Arg Ser Gly Leu Thr Cys Ser Met Trp Glu Lys Asn
                405                 410                 415

Met Glu Asp Leu His Arg His Ile Phe Trp Glu Pro Asp Ala Ser Lys
            420                 425                 430

Leu Asn Lys Asn Tyr Cys Arg Asn Pro Asp Asp Ala His Gly Pro
        435                 440                 445

Trp Cys Tyr Thr Gly Asn Pro Leu Ile Pro Trp Asp Tyr Cys Pro Ile
    450                 455                 460

Ser Arg Cys Glu Gly Asp Thr Thr Pro Thr Ile Val Asn Leu Asp His
465                 470                 475                 480

Pro Val Ile Ser Cys Ala Lys Thr Lys Gln Leu Arg Val Val Asn Gly
                485                 490                 495

Ile Pro Thr Arg Thr Asn Val Gly Trp Met Val Ser Leu Lys Tyr Arg
            500                 505                 510

Asn Lys His Ile Cys Gly Gly Ser Leu Ile Lys Glu Ser Trp Ile Leu
        515                 520                 525

Thr Ala Arg Gln Cys Phe Pro Ser Arg Asn Lys Asp Leu Lys Asp Tyr
    530                 535                 540

Glu Ala Trp Leu Gly Ile His Asp Val His Gly Arg Gly Asp Glu Lys
545                 550                 555                 560

Arg Lys Gln Val Leu Asn Val Ser Gln Leu Val Tyr Gly Pro Glu Gly
                565                 570                 575

Ser Asp Leu Val Leu Leu Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Thr Cys Ser Val Tyr Gly Trp Gly Tyr Thr Gly Ser Ile Asn
    610                 615                 620

Ser Asp Gly Leu Leu Arg Val Ala His Leu Tyr Ile Met Gly Asn Glu
625                 630                 635                 640

Lys Cys Ser Gln Tyr His Gln Gly Lys Val Thr Leu Asn Glu Ser Glu
                645                 650                 655

Ile Cys Ala Gly Ala Glu Asn Ile Val Ser Gly Pro Cys Glu Gly Asp
```

```
                            660                 665                 670
Tyr Gly Gly Pro Leu Val Cys Glu Gln His Lys Met Arg Met Val Leu
            675                 680                 685

Gly Val Ile Val Pro Gly Arg Gly Cys Ala Ile Pro Asn Arg Pro Gly
            690                 695                 700

Ile Phe Val Arg Val Ala Tyr Tyr Ala Lys Trp Ile His Lys Ile Ile
705                 710                 715                 720

Leu Thr Tyr Lys Ile Pro Gln Ser
                725

<210> SEQ ID NO 8
<211> LENGTH: 730
<212> TYPE: PRT
<213> ORGANISM: Bos taurus

<400> SEQUENCE: 8

Met Trp Val Thr Arg Leu Leu Pro Val Leu Leu Gln His Val Leu
 1               5                  10                  15

Leu His Leu Leu Leu Pro Ile Ala Ile Pro Tyr Ala Glu Gly Gln
                20                  25                  30

Lys Lys Arg Arg Asn Thr Leu His Glu Phe Lys Arg Ser Ala Lys Thr
            35                  40                  45

Thr Leu Ile Lys Glu Asp Pro Leu Leu Lys Ile Lys Thr Lys Lys Met
50                  55                  60

Asn Thr Ala Asp Gln Cys Ala Asn Arg Cys Ile Arg Asn Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
            115                 120                 125

Ile Ile Gly Lys Gly Gly Ser Tyr Lys Gly Thr Val Ser Ile Thr Lys
130                 135                 140

Ser Gly Ile Lys Cys Gln Pro Trp Asn Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
                195                 200                 205

Val Glu Cys Met Thr Cys Asn Gly Glu Ser Tyr Arg Gly Pro Met Asp
210                 215                 220

His Thr Glu Thr Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Lys Pro Arg Pro Trp Cys Tyr
            260                 265                 270

Thr Leu Asp Pro Asp Thr Pro Trp Glu Tyr Cys Ala Ile Lys Met Cys
                275                 280                 285

Ala His Ser Thr Met Asn Asp Thr Asp Leu Pro Met Gln Thr Thr Glu
            290                 295                 300
```

```
Cys Ile Gln Gly Gln Gly Glu Gly Tyr Arg Gly Thr Ile Asn Thr Ile
305                 310                 315                 320

Trp Asn Gly Ile Pro Cys Gln Arg Trp Asp Ser Gln Tyr Pro His Gln
            325                 330                 335

His Asp Ile Thr Pro Glu Asn Phe Lys Cys Lys Asp Leu Arg Glu Asn
        340                 345                 350

Tyr Cys Arg Asn Pro Asp Gly Ala Glu Ser Pro Trp Cys Phe Thr Thr
    355                 360                 365

Asp Pro Asn Ile Arg Val Gly Tyr Cys Ser Gln Ile Pro Lys Cys Asp
370                 375                 380

Val Ser Ser Gly Gln Asp Cys Tyr Arg Gly Asn Gly Lys Asn Tyr Met
385             390                 395                 400

Gly Ser Leu Ser Lys Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Thr Lys Leu Asn Lys Asn Tyr Cys Arg Asn Pro Asp Asp Ala His
                435                 440                 445

Gly Pro Trp Cys Tyr Thr Gly Asn Pro Leu Ile Pro Trp Asp Tyr Cys
450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Val Gly Trp Met Val Ser Leu Lys
            500                 505                 510

Tyr Arg Asn Lys His Ile Cys Gly Gly Ser Leu Ile Lys Glu Ser Trp
                515                 520                 525

Ile Leu Thr Ala Arg Gln Cys Phe Pro Ser Arg Asn Lys Asp Leu Lys
530                 535                 540

Asp Tyr Glu Ala Trp Leu Gly Ile His Asp Val His Gly Arg Gly Asp
545                 550                 555                 560

Glu Lys Arg Lys Gln Val Leu Asn Val Thr Gln Leu Val Tyr Gly Pro
                565                 570                 575

Glu Gly Ser Asp Leu Val Leu Leu Lys Leu Ala Arg Pro Ala Ile Leu
            580                 585                 590

Asp Asp Phe Val Ser Thr Ile Asp Leu Pro Asn Tyr Gly Cys Thr Ile
        595                 600                 605

Pro Glu Lys Thr Thr Cys Ser Val Tyr Gly Trp Gly Tyr Thr Gly Leu
610                 615                 620

Ile Asn Ser Asp Gly Leu Leu Arg Val Ala His Leu Tyr Ile Met Gly
625                 630                 635                 640

Asn Glu Lys Cys Ser Gln Tyr His Gln Gly Lys Val Thr Leu Asn Glu
                645                 650                 655

Ser Glu Ile Cys Ala Gly Ala Glu Asn Ile Val Ser Gly Pro Cys Glu
                660                 665                 670

Gly Asp Tyr Gly Gly Pro Leu Val Cys Glu Gln His Lys Met Arg Met
            675                 680                 685

Val Leu Gly Val Ile Val Pro Gly Arg Gly Cys Ala Ile Pro Asn Arg
                690                 695                 700

Pro Gly Ile Phe Val Arg Val Ala Tyr Tyr Ala Lys Trp Ile His Lys
705                 710                 715                 720

Ile Ile Leu Thr Tyr Lys Ala Pro Gln Leu
```

```
                725                 730

<210> SEQ ID NO 9
<211> LENGTH: 10
<212> TYPE: PRT
<213> ORGANISM: Homo sapiens

<400> SEQUENCE: 9

Asp Arg Val Tyr Ile His Pro Phe His Leu
 1               5                  10

<210> SEQ ID NO 10
<211> LENGTH: 10
<212> TYPE: PRT
<213> ORGANISM: Pan troglodytes

<400> SEQUENCE: 10

Asp Arg Val Tyr Ile His Pro Phe His Leu
 1               5                  10

<210> SEQ ID NO 11
<211> LENGTH: 10
<212> TYPE: PRT
<213> ORGANISM: Gorilla gorilla

<400> SEQUENCE: 11

Asp Arg Val Tyr Ile His Pro Phe His Leu
 1               5                  10

<210> SEQ ID NO 12
<211> LENGTH: 10
<212> TYPE: PRT
<213> ORGANISM: Mus musculus

<400> SEQUENCE: 12

Asp Arg Val Tyr Ile His Pro Phe His Leu
 1               5                  10

<210> SEQ ID NO 13
<211> LENGTH: 10
<212> TYPE: PRT
<213> ORGANISM: Rattus norvegicus

<400> SEQUENCE: 13

Asp Arg Val Tyr Ile His Pro Phe His Leu
 1               5                  10

<210> SEQ ID NO 14
<211> LENGTH: 10
<212> TYPE: PRT
<213> ORGANISM: Ovis aries

<400> SEQUENCE: 14

Asp Arg Val Tyr Ile His Pro Phe His Leu
 1               5                  10

<210> SEQ ID NO 15
<211> LENGTH: 10
<212> TYPE: PRT
<213> ORGANISM: Bos taurus

<400> SEQUENCE: 15

Asp Arg Val Tyr Ile His Pro Phe His Leu
 1               5                  10
```

```
<210> SEQ ID NO 16
<211> LENGTH: 10
<212> TYPE: PRT
<213> ORGANISM: Equus caballus

<400> SEQUENCE: 16

Asp Arg Val Tyr Val His Pro Phe His Leu
 1               5                  10

<210> SEQ ID NO 17
<211> LENGTH: 8
<212> TYPE: PRT
<213> ORGANISM: Homo sapiens

<400> SEQUENCE: 17

Asp Arg Val Tyr Ile His Pro Phe
 1               5

<210> SEQ ID NO 18
<211> LENGTH: 8
<212> TYPE: PRT
<213> ORGANISM: Pan troglodytes

<400> SEQUENCE: 18

Asp Arg Val Tyr Ile His Pro Phe
 1               5

<210> SEQ ID NO 19
<211> LENGTH: 8
<212> TYPE: PRT
<213> ORGANISM: Gorilla gorilla

<400> SEQUENCE: 19

Asp Arg Val Tyr Ile His Pro Phe
 1               5

<210> SEQ ID NO 20
<211> LENGTH: 8
<212> TYPE: PRT
<213> ORGANISM: Mus musculus

<400> SEQUENCE: 20

Asp Arg Val Tyr Ile His Pro Phe
 1               5

<210> SEQ ID NO 21
<211> LENGTH: 8
<212> TYPE: PRT
<213> ORGANISM: Rattus norvegicus

<400> SEQUENCE: 21

Asp Arg Val Tyr Ile His Pro Phe
 1               5

<210> SEQ ID NO 22
<211> LENGTH: 8
<212> TYPE: PRT
<213> ORGANISM: Ovis aries

<400> SEQUENCE: 22

Asp Arg Val Tyr Ile His Pro Phe
 1               5

<210> SEQ ID NO 23
```

```
<211> LENGTH: 8
<212> TYPE: PRT
<213> ORGANISM: Bos taurus

<400> SEQUENCE: 23

Asp Arg Val Tyr Ile His Pro Phe
1               5

<210> SEQ ID NO 24
<211> LENGTH: 8
<212> TYPE: PRT
<213> ORGANISM: Equus caballus

<400> SEQUENCE: 24

Asp Arg Val Tyr Val His Pro Phe
1               5

<210> SEQ ID NO 25
<211> LENGTH: 7
<212> TYPE: PRT
<213> ORGANISM: Homo sapiens

<400> SEQUENCE: 25

Arg Val Tyr Ile His Pro Phe
1               5

<210> SEQ ID NO 26
<211> LENGTH: 7
<212> TYPE: PRT
<213> ORGANISM: Pan troglodytes

<400> SEQUENCE: 26

Arg Val Tyr Ile His Pro Phe
1               5

<210> SEQ ID NO 27
<211> LENGTH: 7
<212> TYPE: PRT
<213> ORGANISM: Gorilla gorilla

<400> SEQUENCE: 27

Arg Val Tyr Ile His Pro Phe
1               5

<210> SEQ ID NO 28
<211> LENGTH: 7
<212> TYPE: PRT
<213> ORGANISM: Mus musculus

<400> SEQUENCE: 28

Arg Val Tyr Ile His Pro Phe
1               5

<210> SEQ ID NO 29
<211> LENGTH: 7
<212> TYPE: PRT
<213> ORGANISM: Rattus norvegicus

<400> SEQUENCE: 29

Arg Val Tyr Ile His Pro Phe
1               5

<210> SEQ ID NO 30
<211> LENGTH: 7
<212> TYPE: PRT
```

```
<213> ORGANISM: Ovis aries

<400> SEQUENCE: 30

Arg Val Tyr Ile His Pro Phe
 1               5

<210> SEQ ID NO 31
<211> LENGTH: 7
<212> TYPE: PRT
<213> ORGANISM: Bos taurus

<400> SEQUENCE: 31

Arg Val Tyr Ile His Pro Phe
 1               5

<210> SEQ ID NO 32
<211> LENGTH: 7
<212> TYPE: PRT
<213> ORGANISM: Equus caballus

<400> SEQUENCE: 32

Arg Val Tyr Val His Pro Phe
 1               5

<210> SEQ ID NO 33
<211> LENGTH: 6
<212> TYPE: PRT
<213> ORGANISM: Homo sapiens
<300> PUBLICATION INFORMATION:
<301> AUTHORS: Mustafa, T. et al.
<302> TITLE: Bioactive angiotensin peptides:  focus on angioten
<303> JOURNAL: Journal of the Renin-Angiotensin-Aldosterone Syste
<304> VOLUME: 2
<305> ISSUE: 4
<306> PAGES: 205-210
<307> DATE: 2001-12

<400> SEQUENCE: 33

Val Tyr Ile His Pro Phe
 1               5

<210> SEQ ID NO 34
<211> LENGTH: 6
<212> TYPE: PRT
<213> ORGANISM: Pan troglodytes
<300> PUBLICATION INFORMATION:
<301> AUTHORS: Mustafa, T. et al.
<302> TITLE: Bioactive angiotensin peptides:  focus on angioten
<303> JOURNAL: Journal of the Renin-Angiotensin-Aldosterone Syste
<304> VOLUME: 2
<305> ISSUE: 4
<306> PAGES: 205-210
<307> DATE: 2001-12

<400> SEQUENCE: 34

Val Tyr Ile His Pro Phe
 1               5

<210> SEQ ID NO 35
<211> LENGTH: 6
<212> TYPE: PRT
<213> ORGANISM: Gorilla gorilla
<300> PUBLICATION INFORMATION:
<301> AUTHORS: Mustafa, T. et al.
<302> TITLE: Bioactive angiotensin peptides:  focus on angioten
<303> JOURNAL: Journal of the Renin-Angiotensin-Aldosterone Syste
<304> VOLUME: 2
<305> ISSUE: 4
<306> PAGES: 205-210
```

```
<307> DATE: 2001-12

<400> SEQUENCE: 35

Val Tyr Ile His Pro Phe
1               5

<210> SEQ ID NO 36
<211> LENGTH: 6
<212> TYPE: PRT
<213> ORGANISM: Mus musculus
<300> PUBLICATION INFORMATION:
<301> AUTHORS: Mustafa, T. et al.
<302> TITLE: Bioactive angiotensin peptides: focus on angioten
<303> JOURNAL: Journal of the Renin-Angiotensin-Aldosterone Syste
<304> VOLUME: 2
<305> ISSUE: 4
<306> PAGES: 205-210
<307> DATE: 2001-12

<400> SEQUENCE: 36

Val Tyr Ile His Pro Phe
1               5

<210> SEQ ID NO 37
<211> LENGTH: 6
<212> TYPE: PRT
<213> ORGANISM: Rattus norvegicus
<300> PUBLICATION INFORMATION:
<301> AUTHORS: Mustafa, T. et al.
<302> TITLE: Bioactive angiotensin peptides: focus on angioten
<303> JOURNAL: Journal of the Renin-Angiotensin-Aldosterone Syste
<304> VOLUME: 2
<305> ISSUE: 4
<306> PAGES: 205-210
<307> DATE: 2001-12

<400> SEQUENCE: 37

Val Tyr Ile His Pro Phe
1               5

<210> SEQ ID NO 38
<211> LENGTH: 6
<212> TYPE: PRT
<213> ORGANISM: Ovis aries
<300> PUBLICATION INFORMATION:
<301> AUTHORS: Mustafa, T. et al.
<302> TITLE: Bioactive angiotensin peptides: focus on angioten
<303> JOURNAL: Journal of the Renin-Angiotensin-Aldosterone Syste
<304> VOLUME: 2
<305> ISSUE: 4
<306> PAGES: 205-210
<307> DATE: 2001-12

<400> SEQUENCE: 38

Val Tyr Ile His Pro Phe
1               5

<210> SEQ ID NO 39
<211> LENGTH: 6
<212> TYPE: PRT
<213> ORGANISM: Bos taurus
<300> PUBLICATION INFORMATION:
<301> AUTHORS: Mustafa, T. et al.
<302> TITLE: Bioactive angiotensin peptides: focus on angioten
<303> JOURNAL: Journal of the Renin-Angiotensin-Aldosterone Syste
<304> VOLUME: 2
<305> ISSUE: 4
<306> PAGES: 205-210
<307> DATE: 2001-12

<400> SEQUENCE: 39
```

Val Tyr Ile His Pro Phe
1               5

<210> SEQ ID NO 40
<211> LENGTH: 6
<212> TYPE: PRT
<213> ORGANISM: Equus caballus
<300> PUBLICATION INFORMATION:
<301> AUTHORS: Mustafa, T. et al.
<302> TITLE: Bioactive angiotensin peptides:   focus on angioten
<303> JOURNAL: Journal of the Renin-Angiotensin-Aldosterone Syste
<304> VOLUME: 2
<305> ISSUE: 4
<306> PAGES: 205-210
<307> DATE: 2001-12

<400> SEQUENCE: 40

Val Tyr Val His Pro Phe
1               5

<210> SEQ ID NO 41
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle

<400> SEQUENCE: 41

Xaa Tyr Ile His Pro Phe
1               5

<210> SEQ ID NO 42
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: SITE
<222> LOCATION: (1)...(2)
<223> OTHER INFORMATION: A reduced peptide bond (-CH2-NH2-)
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 42

Val Tyr Leu His Pro Phe
1               5

<210> SEQ ID NO 43
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 43

```
Xaa Tyr Leu His Pro Phe
1               5

<210> SEQ ID NO 44
<211> LENGTH: 5
<212> TYPE: PRT
<213> ORGANISM: Artificial Sequence
<220> FEATURE:
<223> OTHER INFORMATION: Angiotensin ligand

<400> SEQUENCE: 44

Tyr Ile His Pro Phe
1               5

<210> SEQ ID NO 45
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle
<220> FEATURE:
<221> NAME/KEY: SITE
<222> LOCATION: (1)...(2)
<223> OTHER INFORMATION: A reduced peptide bond (-CH2-NH2-)

<400> SEQUENCE: 45

Xaa Tyr Ile His Pro Phe
1               5

<210> SEQ ID NO 46
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: SITE
<222> LOCATION: (1)...(2)
<223> OTHER INFORMATION: A reduced peptide bond (-CH2-NH2-)
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 46

Leu Tyr Leu His Pro Phe
1               5

<210> SEQ ID NO 47
<211> LENGTH: 4
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle

<400> SEQUENCE: 47

Xaa Tyr Ile His
1

<210> SEQ ID NO 48
<211> LENGTH: 4
<212> TYPE: PRT
```

```
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle
<220> FEATURE:
<221> NAME/KEY: SITE
<222> LOCATION: (3)...(4)
<223> OTHER INFORMATION: (CH2)6 linker between residues
<220> FEATURE:
<221> NAME/KEY: AMIDATION
<222> LOCATION: 4

<400> SEQUENCE: 48

Xaa Tyr Ile Phe
 1

<210> SEQ ID NO 49
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle
<220> FEATURE:
<221> NAME/KEY: MOD_RES
<222> LOCATION: (4)...(5)
<223> OTHER INFORMATION: MeGly
<220> FEATURE:
<221> NAME/KEY: MOD_RES
<222> LOCATION: 6
<223> OTHER INFORMATION: Phe is the dPhe variant

<400> SEQUENCE: 49

Xaa Tyr Ile Xaa Xaa Phe
 1               5

<210> SEQ ID NO 50
<211> LENGTH: 13
<212> TYPE: PRT
<213> ORGANISM: Unknown
<220> FEATURE:
<223> OTHER INFORMATION: Angiotensinogen peptide sequence disclosed in
      publication

<400> SEQUENCE: 50

Asp Arg Val Tyr Ile His Pro Phe His Leu Leu Val Tyr
 1               5                  10

<210> SEQ ID NO 51
<211> LENGTH: 14
<212> TYPE: PRT
<213> ORGANISM: Equus caballus

<400> SEQUENCE: 51

Asp Arg Val Tyr Ile His Pro Phe His Leu Leu Val Tyr Ser
 1               5                  10

<210> SEQ ID NO 52
<211> LENGTH: 4
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
```

```
<222> LOCATION: 1
<223> OTHER INFORMATION: Nle
<220> FEATURE:
<221> NAME/KEY: MOD_RES
<222> LOCATION: 4
<223> OTHER INFORMATION: 6-(amino) hexanoic acid amide

<400> SEQUENCE: 52

Xaa Tyr Ile Xaa
 1

<210> SEQ ID NO 53
<211> LENGTH: 5
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle

<400> SEQUENCE: 53

Xaa Tyr Ile His Pro
 1               5

<210> SEQ ID NO 54
<211> LENGTH: 6
<212> TYPE: PRT
<213> ORGANISM: Artificial Sequence
<220> FEATURE:
<223> OTHER INFORMATION: Angiotensin ligand

<400> SEQUENCE: 54

Lys Tyr Ile His Pro Phe
 1               5

<210> SEQ ID NO 55
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Xaa = benzyl-cysteine

<400> SEQUENCE: 55

Xaa Tyr Ile His Pro Phe
 1               5

<210> SEQ ID NO 56
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Xaa = dNle variant

<400> SEQUENCE: 56

Xaa Tyr Ile His Pro Phe
 1               5

<210> SEQ ID NO 57
<211> LENGTH: 6
```

```
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 57

Xaa Tyr Ile His Pro Phe
 1               5

<210> SEQ ID NO 58
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 58

Xaa Tyr Val His Pro Phe
 1               5

<210> SEQ ID NO 59
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1, 3
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 59

Xaa Tyr Xaa His Pro Phe
 1               5

<210> SEQ ID NO 60
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 60

Xaa Phe Leu His Pro Phe
```

1               5

<210> SEQ ID NO 61
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 61

Xaa Phe Ile His Pro Phe
1               5

<210> SEQ ID NO 62
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 62

Xaa Phe Val His Pro Phe
1               5

<210> SEQ ID NO 63
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1, 3
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 63

Xaa Phe Xaa His Pro Phe
1               5

<210> SEQ ID NO 64
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle
<220> FEATURE:
<221> NAME/KEY: SITE
<222> LOCATION: (3)...(4)

```
<223> OTHER INFORMATION: A reduced peptide bond (-CH2-NH2-)

<400> SEQUENCE: 64

Xaa Tyr Leu Arg Pro Phe
 1               5

<210> SEQ ID NO 65
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 65

Xaa Tyr Ile Arg Pro Phe
 1               5

<210> SEQ ID NO 66
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 66

Xaa Tyr Val Arg Pro Phe
 1               5

<210> SEQ ID NO 67
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1, 3
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 67

Xaa Tyr Xaa Arg Pro Phe
 1               5

<210> SEQ ID NO 68
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
```

-continued

```
<222> LOCATION: 1
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 68

Xaa Phe Leu Arg Pro Phe
 1               5

<210> SEQ ID NO 69
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 69

Xaa Phe Ile Arg Pro Phe
 1               5

<210> SEQ ID NO 70
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 70

Xaa Phe Val Arg Pro Phe
 1               5

<210> SEQ ID NO 71
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1, 3
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 71

Xaa Phe Xaa Arg Pro Phe
 1               5

<210> SEQ ID NO 72
<211> LENGTH: 6
<212> TYPE: PRT
```

```
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 72

Xaa Tyr Leu Lys Pro Phe
 1               5

<210> SEQ ID NO 73
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 73

Xaa Tyr Ile Lys Pro Phe
 1               5

<210> SEQ ID NO 74
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 74

Xaa Tyr Val Lys Pro Phe
 1               5

<210> SEQ ID NO 75
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1,3
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 75

Xaa Tyr Xaa Lys Pro Phe
 1               5
```

```
<210> SEQ ID NO 76
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 76

Xaa Phe Leu Lys Pro Phe
 1               5

<210> SEQ ID NO 77
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 77

Xaa Phe Ile Lys Pro Phe
 1               5

<210> SEQ ID NO 78
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 78

Xaa Phe Val Lys Pro Phe
 1               5

<210> SEQ ID NO 79
<211> LENGTH: 6
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1,3
<223> OTHER INFORMATION: Nle
<220> FEATURE:
<221> NAME/KEY: SITE
<222> LOCATION: (3)...(4)
<223> OTHER INFORMATION: A reduced peptide bond (-CH2-NH2-)
```

<400> SEQUENCE: 79

Xaa Phe Xaa Lys Pro Phe
 1               5

<210> SEQ ID NO 80
<211> LENGTH: 3
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: Xaa = gamma-aminobutyric acid

<400> SEQUENCE: 80

Xaa Tyr Ile
 1

<210> SEQ ID NO 81
<211> LENGTH: 3
<212> TYPE: PRT
<213> ORGANISM: Artificial Sequence
<220> FEATURE:
<223> OTHER INFORMATION: Angiotensin ligand
<220> FEATURE:
<221> NAME/KEY: MOD_RES
<222> LOCATION: 1
<223> OTHER INFORMATION: bAla

<400> SEQUENCE: 81

Xaa Tyr Ile
 1

<210> SEQ ID NO 82
<211> LENGTH: 7
<212> TYPE: PRT
<213> ORGANISM: Homo sapiens

<400> SEQUENCE: 82

Lys Asp Tyr Ile Arg Asn Cys
 1               5

<210> SEQ ID NO 83
<211> LENGTH: 728
<212> TYPE: PRT
<213> ORGANISM: Homo sapiens

<400> SEQUENCE: 83

Met Trp Val Thr Lys Leu Leu Pro Ala Leu Leu Leu Gln His Val Leu
 1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
        50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
                100                 105                 110

```
Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
                180                 185                 190

Asn Pro Glu Val Arg Tyr Glu Val Cys Asp Ile Pro Gln Cys Ser Glu
            195                 200                 205

Val Glu Cys Met Thr Cys Asn Gly Glu Ser Tyr Arg Gly Leu Met Asp
        210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525
```

```
Val Leu Thr Ala Arg Gln Cys Phe Pro Ser Arg Asp Leu Lys Asp Tyr
            530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
                595                 600                 605

Lys Thr Ser Cys Ser Val Tyr Gly Trp Gly Tyr Thr Gly Leu Ile Asn
610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
                660                 665                 670

Tyr Gly Gly Pro Leu Val Cys Glu Gln His Lys Met Arg Met Val Leu
            675                 680                 685

Gly Val Ile Val Pro Gly Arg Gly Cys Ala Ile Pro Asn Arg Pro Gly
690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 84
<211> LENGTH: 1408
<212> TYPE: PRT
<213> ORGANISM: Homo sapiens

<400> SEQUENCE: 84

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65              70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175
```

```
Val Ser Ala Leu Gly Ala Lys Val Leu Ser Val Lys Asp Arg Phe
            180                 185                 190

Ile Asn Phe Phe Val Gly Asn Thr Ile Asn Ser Ser Tyr Phe Pro Asp
            195                 200                 205

His Pro Leu His Ser Ile Ser Val Arg Arg Leu Lys Glu Thr Lys Asp
            210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
            275                 280                 285

His Ser Tyr Met Glu Met Pro Leu Glu Cys Ile Leu Thr Glu Lys Arg
            290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
            355                 360                 365

Tyr Val Asn Asp Phe Phe Asn Lys Ile Val Asn Lys Asn Asn Val Arg
            370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
            435                 440                 445

Asp Leu Thr Ile Ala Asn Leu Gly Thr Ser Glu Gly Arg Phe Met Gln
            450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
            530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590
```

```
Asn Asn Lys Phe Asp Leu Lys Lys Thr Arg Val Leu Leu Gly Asn Glu
                595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
                740                 745                 750

Phe Ile Ser Thr Trp Trp Lys Glu Pro Leu Asn Ile Val Ser Phe Leu
    755                 760                 765

Phe Cys Phe Ala Ser Gly Gly Ser Thr Ile Thr Gly Val Gly Lys Asn
    770                 775                 780

Leu Asn Ser Val Ser Val Pro Arg Met Val Ile Asn Val His Glu Ala
785                 790                 795                 800

Gly Arg Asn Phe Thr Val Ala Cys Gln His Arg Ser Asn Ser Glu Ile
                805                 810                 815

Ile Cys Cys Thr Thr Pro Ser Leu Gln Gln Leu Asn Leu Gln Leu Pro
                820                 825                 830

Leu Lys Thr Lys Ala Phe Phe Met Leu Asp Gly Ile Leu Ser Lys Tyr
                835                 840                 845

Phe Asp Leu Ile Tyr Val His Asn Pro Val Phe Lys Pro Phe Glu Lys
850                 855                 860

Pro Val Met Ile Ser Met Gly Asn Glu Asn Val Leu Glu Ile Lys Gly
865                 870                 875                 880

Asn Asp Ile Asp Pro Glu Ala Val Lys Gly Glu Val Leu Lys Val Gly
                885                 890                 895

Asn Lys Ser Cys Glu Asn Ile His Leu His Ser Glu Ala Val Leu Cys
                900                 905                 910

Thr Val Pro Asn Asp Leu Leu Lys Leu Asn Ser Glu Leu Asn Ile Glu
                915                 920                 925

Trp Lys Gln Ala Ile Ser Ser Thr Val Leu Gly Lys Val Ile Val Gln
    930                 935                 940

Pro Asp Gln Asn Phe Thr Gly Leu Ile Ala Gly Val Val Ser Ile Ser
945                 950                 955                 960

Thr Ala Leu Leu Leu Leu Leu Gly Phe Phe Leu Trp Leu Lys Lys Arg
                965                 970                 975

Lys Gln Ile Lys Asp Leu Gly Ser Glu Leu Val Arg Tyr Asp Ala Arg
                980                 985                 990

Val His Thr Pro His Leu Asp Arg Leu Val Ser Ala Arg Ser Val Ser
                995                 1000                1005

Pro Thr Thr Glu Met Val Ser Asn Glu Ser Val Asp Tyr Arg Ala Thr
```

```
                    1010                1015                1020

Phe Pro Glu Asp Gln Phe Pro Asn Ser Ser Gln Asn Gly Ser Cys Arg
1025                1030                1035                1040

Gln Val Gln Tyr Pro Leu Thr Asp Met Ser Pro Ile Leu Thr Ser Gly
                    1045                1050                1055

Asp Ser Asp Ile Ser Ser Pro Leu Leu Gln Asn Thr Val His Ile Asp
                1060                1065                1070

Leu Ser Ala Leu Asn Pro Glu Leu Val Gln Ala Val Gln His Val Val
            1075                1080                1085

Ile Gly Pro Ser Ser Leu Ile Val His Phe Asn Glu Val Ile Gly Arg
        1090                1095                1100

Gly His Phe Gly Cys Val Tyr His Gly Thr Leu Leu Asp Asn Asp Gly
1105                1110                1115                1120

Lys Lys Ile His Cys Ala Val Lys Ser Leu Asn Arg Ile Thr Asp Ile
                    1125                1130                1135

Gly Glu Val Ser Gln Phe Leu Thr Glu Gly Ile Ile Met Lys Asp Phe
                1140                1145                1150

Ser His Pro Asn Val Leu Ser Leu Leu Gly Ile Cys Leu Arg Ser Glu
            1155                1160                1165

Gly Ser Pro Leu Val Val Leu Pro Tyr Met Lys His Gly Asp Leu Arg
        1170                1175                1180

Asn Phe Ile Arg Asn Glu Thr His Asn Pro Thr Val Lys Asp Leu Ile
1185                1190                1195                1200

Gly Phe Gly Leu Gln Val Ala Lys Ala Met Lys Tyr Leu Ala Ser Lys
                    1205                1210                1215

Lys Phe Val His Arg Asp Leu Ala Ala Arg Asn Cys Met Leu Asp Glu
                1220                1225                1230

Lys Phe Thr Val Lys Val Ala Asp Phe Gly Leu Ala Arg Asp Met Tyr
            1235                1240                1245

Asp Lys Glu Tyr Tyr Ser Val His Asn Lys Thr Gly Ala Lys Leu Pro
        1250                1255                1260

Val Lys Trp Met Ala Leu Glu Ser Leu Gln Thr Gln Lys Phe Thr Thr
1265                1270                1275                1280

Lys Ser Asp Val Trp Ser Phe Gly Val Val Leu Trp Glu Leu Met Thr
                    1285                1290                1295

Arg Gly Ala Pro Pro Tyr Pro Asp Val Asn Thr Phe Asp Ile Thr Val
                1300                1305                1310

Tyr Leu Leu Gln Gly Arg Arg Leu Leu Gln Pro Glu Tyr Cys Pro Asp
            1315                1320                1325

Pro Leu Tyr Glu Val Met Leu Lys Cys Trp His Pro Lys Ala Glu Met
        1330                1335                1340

Arg Pro Ser Phe Ser Glu Leu Val Ser Arg Ile Ser Ala Ile Phe Ser
1345                1350                1355                1360

Thr Phe Ile Gly Glu His Tyr Val His Val Asn Ala Thr Tyr Val Asn
                    1365                1370                1375

Val Lys Cys Val Ala Pro Tyr Pro Ser Leu Leu Ser Ser Glu Asp Asn
                1380                1385                1390

Ala Asp Asp Glu Val Asp Thr Arg Pro Ala Ser Phe Trp Glu Thr Ser
            1395                1400                1405

<210> SEQ ID NO 85
<211> LENGTH: 6
<212> TYPE: PRT
<213> ORGANISM: Artificial Sequence
```

```
<220> FEATURE:
<223> OTHER INFORMATION: Angiotensin ligand
<220> FEATURE:
<221> NAME/KEY: SITE
<222> LOCATION: (1)...(2)
<223> OTHER INFORMATION: A reduced peptide bond (-CH2-NH2-)
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 85

Val Tyr Val His Pro Phe
 1               5

<210> SEQ ID NO 86
<211> LENGTH: 4
<212> TYPE: PRT
<213> ORGANISM: Artificial Sequence
<220> FEATURE:
<223> OTHER INFORMATION: Angiotensin ligand

<400> SEQUENCE: 86

Lys Asp Tyr Ile
 1

<210> SEQ ID NO 87
<211> LENGTH: 4
<212> TYPE: PRT
<213> ORGANISM: Artificial Sequence
<220> FEATURE:
<223> OTHER INFORMATION: Angiotensin ligand

<400> SEQUENCE: 87

Asp Tyr Ile Arg
 1

<210> SEQ ID NO 88
<211> LENGTH: 4
<212> TYPE: PRT
<213> ORGANISM: Artificial Sequence
<220> FEATURE:
<223> OTHER INFORMATION: Angiotensin ligand

<400> SEQUENCE: 88

Tyr Ile Arg Asn
 1

<210> SEQ ID NO 89
<211> LENGTH: 4
<212> TYPE: PRT
<213> ORGANISM: Artificial Sequence
<220> FEATURE:
<223> OTHER INFORMATION: Angiotensin ligand

<400> SEQUENCE: 89

Ile Arg Asn Cys
 1

<210> SEQ ID NO 90
<211> LENGTH: 5
<212> TYPE: PRT
<213> ORGANISM: Artificial Sequence
<220> FEATURE:
<223> OTHER INFORMATION: Angiotensin ligand

<400> SEQUENCE: 90

Lys Asp Tyr Ile Arg
```

<210> SEQ ID NO 91
<211> LENGTH: 5
<212> TYPE: PRT
<213> ORGANISM: Artificial Sequence
<220> FEATURE:
<223> OTHER INFORMATION: Angiotensin ligand

<400> SEQUENCE: 91

Asp Tyr Ile Arg Asn
1               5

<210> SEQ ID NO 92
<211> LENGTH: 5
<212> TYPE: PRT
<213> ORGANISM: Artificial Sequence
<220> FEATURE:
<223> OTHER INFORMATION: Angiotensin ligand

<400> SEQUENCE: 92

Tyr Ile Arg Asn Cys
1               5

<210> SEQ ID NO 93
<211> LENGTH: 6
<212> TYPE: PRT
<213> ORGANISM: Artificial Sequence
<220> FEATURE:
<223> OTHER INFORMATION: Angiotensin ligand

<400> SEQUENCE: 93

Lys Asp Tyr Ile Arg Asn
1               5

<210> SEQ ID NO 94
<211> LENGTH: 6
<212> TYPE: PRT
<213> ORGANISM: Artificial Sequence
<220> FEATURE:
<223> OTHER INFORMATION: Angiotensin ligand

<400> SEQUENCE: 94

Asp Tyr Ile Arg Asn Cys
1               5

<210> SEQ ID NO 95
<211> LENGTH: 7
<212> TYPE: PRT
<213> ORGANISM: Artificial Sequence
<220> FEATURE:
<223> OTHER INFORMATION: Angiotensin ligand

<400> SEQUENCE: 95

Gly Asp Tyr Ile Arg Asn Cys
1               5

<210> SEQ ID NO 96
<211> LENGTH: 7
<212> TYPE: PRT
<213> ORGANISM: Artificial Sequence
<220> FEATURE:
<223> OTHER INFORMATION: Angiotensin ligand

<400> SEQUENCE: 96

Lys Gly Tyr Ile Arg Asn Cys
1               5

<210> SEQ ID NO 97
<211> LENGTH: 7
<212> TYPE: PRT
<213> ORGANISM: Artificial Sequence
<220> FEATURE:
<223> OTHER INFORMATION: Angiotensin ligand

<400> SEQUENCE: 97

Lys Asp Gly Ile Arg Asn Cys
 1               5

<210> SEQ ID NO 98
<211> LENGTH: 7
<212> TYPE: PRT
<213> ORGANISM: Artificial Sequence
<220> FEATURE:
<223> OTHER INFORMATION: Angiotensin ligand

<400> SEQUENCE: 98

Lys Asp Tyr Gly Arg Asn Cys
 1               5

<210> SEQ ID NO 99
<211> LENGTH: 7
<212> TYPE: PRT
<213> ORGANISM: Artificial Sequence
<220> FEATURE:
<223> OTHER INFORMATION: Angiotensin ligand

<400> SEQUENCE: 99

Lys Asp Tyr Ile Gly Asn Cys
 1               5

<210> SEQ ID NO 100
<211> LENGTH: 7
<212> TYPE: PRT
<213> ORGANISM: Artificial Sequence
<220> FEATURE:
<223> OTHER INFORMATION: Angiotensin ligand

<400> SEQUENCE: 100

Lys Asp Tyr Ile Arg Gly Cys
 1               5

<210> SEQ ID NO 101
<211> LENGTH: 7
<212> TYPE: PRT
<213> ORGANISM: Artificial Sequence
<220> FEATURE:
<223> OTHER INFORMATION: Angiotensin ligand

<400> SEQUENCE: 101

Lys Asp Tyr Ile Arg Asn Gly
 1               5

<210> SEQ ID NO 102
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: MOD_RES
<222> LOCATION: 1
<223> OTHER INFORMATION: D-Lysine is used

```
<400> SEQUENCE: 102

Lys Asp Tyr Ile Arg Asn Cys
1               5

<210> SEQ ID NO 103
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: MOD_RES
<222> LOCATION: 2
<223> OTHER INFORMATION: D-Aspartic Acid

<400> SEQUENCE: 103

Lys Asp Tyr Ile Arg Asn Cys
1               5

<210> SEQ ID NO 104
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: MOD_RES
<222> LOCATION: 3
<223> OTHER INFORMATION: D-Tyrosine

<400> SEQUENCE: 104

Lys Asp Tyr Ile Arg Asn Cys
1               5

<210> SEQ ID NO 105
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: MOD_RES
<222> LOCATION: 4
<223> OTHER INFORMATION: D-Isoleucine

<400> SEQUENCE: 105

Lys Asp Tyr Ile Arg Asn Cys
1               5

<210> SEQ ID NO 106
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: MOD_RES
<222> LOCATION: 5
<223> OTHER INFORMATION: D-Arginine

<400> SEQUENCE: 106

Lys Asp Tyr Ile Arg Asn Cys
1               5

<210> SEQ ID NO 107
```

```
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: MOD_RES
<222> LOCATION: 6
<223> OTHER INFORMATION: D-Asparigine

<400> SEQUENCE: 107

Lys Asp Tyr Ile Arg Asn Cys
 1               5

<210> SEQ ID NO 108
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: MOD_RES
<222> LOCATION: 7
<223> OTHER INFORMATION: D-Cysteine

<400> SEQUENCE: 108

Lys Asp Tyr Ile Arg Asn Cys
 1               5

<210> SEQ ID NO 109
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: SITE
<222> LOCATION: (1)...(2)
<223> OTHER INFORMATION: A reduced peptide bond (-CH2-NH2-)

<400> SEQUENCE: 109

Lys Asp Tyr Ile Arg Asn Cys
 1               5

<210> SEQ ID NO 110
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: SITE
<222> LOCATION: (2)...(3)
<223> OTHER INFORMATION: A reduced peptide bond (-CH2-NH2-)

<400> SEQUENCE: 110

Lys Asp Tyr Ile Arg Asn Cys
 1               5

<210> SEQ ID NO 111
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
```

```
<221> NAME/KEY: SITE
<222> LOCATION: (3)...(4)
<223> OTHER INFORMATION: A reduced peptide bond (-CH2-NH2-)

<400> SEQUENCE: 111

Lys Asp Tyr Ile Arg Asn Cys
 1               5

<210> SEQ ID NO 112
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: SITE
<222> LOCATION: (4)...(5)
<223> OTHER INFORMATION: A reduced peptide bond (-CH2-NH2-)

<400> SEQUENCE: 112

Lys Asp Tyr Ile Arg Asn Cys
 1               5

<210> SEQ ID NO 113
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: SITE
<222> LOCATION: (5)...(6)
<223> OTHER INFORMATION: A reduced peptide bond (-CH2-NH2-)

<400> SEQUENCE: 113

Lys Asp Tyr Ile Arg Asn Cys
 1               5

<210> SEQ ID NO 114
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: SITE
<222> LOCATION: (6)...(7)
<223> OTHER INFORMATION: A reduced peptide bond (-CH2-NH2-)

<400> SEQUENCE: 114

Lys Asp Tyr Ile Arg Asn Cys
 1               5

<210> SEQ ID NO 115
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: SITE
<222> LOCATION: (1)...(2)
<223> OTHER INFORMATION: A reduced peptide bond (-CH2-NH2-)
<220> FEATURE:
<221> NAME/KEY: SITE
<222> LOCATION: (2)...(3)
<223> OTHER INFORMATION: A reduced peptide bond (-CH2-NH2-)
```

```
<400> SEQUENCE: 115

Lys Asp Tyr Ile Arg Asn Cys
  1               5

<210> SEQ ID NO 116
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: SITE
<222> LOCATION: (1)...(2)
<223> OTHER INFORMATION: A reduced peptide bond (-CH2-NH2-)
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 116

Lys Asp Tyr Ile Arg Asn Cys
  1               5

<210> SEQ ID NO 117
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: SITE
<222> LOCATION: (1)...(2)
<223> OTHER INFORMATION: A reduced peptide bond (-CH2-NH2-)
<220> FEATURE:
<221> NAME/KEY: SITE
<222> LOCATION: (4)...(5)
<223> OTHER INFORMATION: A reduced peptide bond (-CH2-NH2-)

<400> SEQUENCE: 117

Lys Asp Tyr Ile Arg Asn Cys
  1               5

<210> SEQ ID NO 118
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: SITE
<222> LOCATION: (1)...(2)
<223> OTHER INFORMATION: A reduced peptide bond (-CH2-NH2-)
<220> FEATURE:
<221> NAME/KEY: SITE
<222> LOCATION: (5)...(6)
<223> OTHER INFORMATION: A reduced peptide bond (-CH2-NH2-)

<400> SEQUENCE: 118

Lys Asp Tyr Ile Arg Asn Cys
  1               5

<210> SEQ ID NO 119
<211> LENGTH: 7
<212> TYPE: PRT
<213> ORGANISM: Artificial Sequence
<220> FEATURE:
<223> OTHER INFORMATION: Angiotensin ligand - Modified variation of SEQ
```

```
            ID NO:82
<220> FEATURE:
<221> NAME/KEY: SITE
<222> LOCATION: (1)...(2)
<223> OTHER INFORMATION: A reduced peptide bond (-CH2-NH2-)
<220> FEATURE:
<221> NAME/KEY: SITE
<222> LOCATION: (6)...(7)
<223> OTHER INFORMATION: A reduced peptide bond (-CH2-NH2-)

<400> SEQUENCE: 119

Lys Asp Tyr Ile Arg Asn Cys
 1               5

<210> SEQ ID NO 120
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: SITE
<222> LOCATION: (2)...(3)
<223> OTHER INFORMATION: A reduced peptide bond (-CH2-NH2-)
<220> FEATURE:
<221> NAME/KEY: SITE
<222> LOCATION: (3)...(4)
<223> OTHER INFORMATION: A reduced peptide bond (-CH2-NH2-)

<400> SEQUENCE: 120

Lys Asp Tyr Ile Arg Asn Cys
 1               5

<210> SEQ ID NO 121
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: SITE
<222> LOCATION: (2)...(3)
<223> OTHER INFORMATION: A reduced peptide bond (-CH2-NH2-)
<220> FEATURE:
<221> NAME/KEY: SITE
<222> LOCATION: (4)...(5)
<223> OTHER INFORMATION: A reduced peptide bond (-CH2-NH2-)

<400> SEQUENCE: 121

Lys Asp Tyr Ile Arg Asn Cys
 1               5

<210> SEQ ID NO 122
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: SITE
<222> LOCATION: (2)...(3)
<223> OTHER INFORMATION: A reduced peptide bond (-CH2-NH2-)
<220> FEATURE:
<221> NAME/KEY: SITE
<222> LOCATION: (5)...(6)
<223> OTHER INFORMATION: A reduced peptide bond (-CH2-NH2-)

<400> SEQUENCE: 122

Lys Asp Tyr Ile Arg Asn Cys
```

```
1               5
```

<210> SEQ ID NO 123
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: SITE
<222> LOCATION: (2)...(3)
<223> OTHER INFORMATION: A reduced peptide bond (-CH2-NH2-)
<220> FEATURE:
<221> NAME/KEY: SITE
<222> LOCATION: (6)...(7)
<223> OTHER INFORMATION: A reduced peptide bond (-CH2-NH2-)

<400> SEQUENCE: 123

```
Lys Asp Tyr Ile Arg Asn Cys
1               5
```

<210> SEQ ID NO 124
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: SITE
<222> LOCATION: (3)...(4)
<223> OTHER INFORMATION: A reduced peptide bond (-CH2-NH2-)
<220> FEATURE:
<221> NAME/KEY: SITE
<222> LOCATION: (4)...(5)
<223> OTHER INFORMATION: A reduced peptide bond (-CH2-NH2-)

<400> SEQUENCE: 124

```
Lys Asp Tyr Ile Arg Asn Cys
1               5
```

<210> SEQ ID NO 125
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: SITE
<222> LOCATION: (3)...(4)
<223> OTHER INFORMATION: A reduced peptide bond (-CH2-NH2-)
<220> FEATURE:
<221> NAME/KEY: SITE
<222> LOCATION: (5)...(6)
<223> OTHER INFORMATION: A reduced peptide bond (-CH2-NH2-)

<400> SEQUENCE: 125

```
Lys Asp Tyr Ile Arg Asn Cys
1               5
```

<210> SEQ ID NO 126
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: SITE
<222> LOCATION: (3)...(4)

```
<223> OTHER INFORMATION: A reduced peptide bond (-CH2-NH2-)
<220> FEATURE:
<221> NAME/KEY: SITE
<222> LOCATION: (6)...(7)
<223> OTHER INFORMATION: A reduced peptide bond (-CH2-NH2-)

<400> SEQUENCE: 126

Lys Asp Tyr Ile Arg Asn Cys
 1               5

<210> SEQ ID NO 127
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: SITE
<222> LOCATION: (4)...(5)
<223> OTHER INFORMATION: A reduced peptide bond (-CH2-NH2-)
<220> FEATURE:
<221> NAME/KEY: SITE
<222> LOCATION: (5)...(6)
<223> OTHER INFORMATION: A reduced peptide bond (-CH2-NH2-)

<400> SEQUENCE: 127

Lys Asp Tyr Ile Arg Asn Cys
 1               5

<210> SEQ ID NO 128
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: SITE
<222> LOCATION: (4)...(5)
<223> OTHER INFORMATION: A reduced peptide bond (-CH2-NH2-)
<220> FEATURE:
<221> NAME/KEY: SITE
<222> LOCATION: (6)...(7)
<223> OTHER INFORMATION: A reduced peptide bond (-CH2-NH2-)

<400> SEQUENCE: 128

Lys Asp Tyr Ile Arg Asn Cys
 1               5

<210> SEQ ID NO 129
<211> LENGTH: 7
<212> TYPE: PRT
<213> ORGANISM: Artificial Sequence
<220> FEATURE:
<223> OTHER INFORMATION: Angiotensin ligand - Modified variation of SEQ
      ID NO:82
<220> FEATURE:
<221> NAME/KEY: SITE
<222> LOCATION: (5)...(6)
<223> OTHER INFORMATION: A reduced peptide bond (-CH2-NH2-)
<220> FEATURE:
<221> NAME/KEY: SITE
<222> LOCATION: (6)...(7)
<223> OTHER INFORMATION: A reduced peptide bond (-CH2-NH2-)

<400> SEQUENCE: 129

Lys Asp Tyr Ile Arg Asn Cys
 1               5

<210> SEQ ID NO 130
```

```
<211> LENGTH: 7
<212> TYPE: PRT
<213> ORGANISM: Artificial Sequence
<220> FEATURE:
<223> OTHER INFORMATION: General formula for an angiotensin ligand
<220> FEATURE:
<221> NAME/KEY: VARIANT
<222> LOCATION: 1
<223> OTHER INFORMATION: Xaa = Nothing, Lys, Arg, His, Nle or Hexanoic
      acid
<220> FEATURE:
<221> NAME/KEY: VARIANT
<222> LOCATION: 2
<223> OTHER INFORMATION: Xaa = Nothing, Asp or Glu
<220> FEATURE:
<221> NAME/KEY: VARIANT
<222> LOCATION: 3
<223> OTHER INFORMATION: Xaa = Nothing, Tyr, Phe or Homophenylalanine
<220> FEATURE:
<221> NAME/KEY: VARIANT
<222> LOCATION: 4
<223> OTHER INFORMATION: Xaa = Nothing, Ile, Leu, Val, Phe, Met or Nle
<220> FEATURE:
<221> NAME/KEY: VARIANT
<222> LOCATION: 5
<223> OTHER INFORMATION: Xaa = Nothing, Arg, Lys or His
<220> FEATURE:
<221> NAME/KEY: VARIANT
<222> LOCATION: (6)...(6)
<223> OTHER INFORMATION: Xaa = Nothing, Asn or Gln
<220> FEATURE:
<221> NAME/KEY: VARIANT
<222> LOCATION: (7)...(7)
<223> OTHER INFORMATION: Xaa = Nothing, Cys or Cys-amide

<400> SEQUENCE: 130

Xaa Xaa Xaa Xaa Xaa Xaa Xaa
 1               5

<210> SEQ ID NO 131
<211> LENGTH: 6
<212> TYPE: PRT
<213> ORGANISM: Artificial Sequence
<220> FEATURE:
<223> OTHER INFORMATION: Synthetic peptide based on HGF precursor

<400> SEQUENCE: 131

Asp Tyr Ile Arg Asn Cys
 1               5

<210> SEQ ID NO 132
<211> LENGTH: 6
<212> TYPE: PRT
<213> ORGANISM: Artificial Sequence
<220> FEATURE:
<223> OTHER INFORMATION: Synthetic peptide based on plasminogen
      precursor

<400> SEQUENCE: 132

Val Tyr Leu Ser Glu Cys
 1               5

<210> SEQ ID NO 133
<211> LENGTH: 6
<212> TYPE: PRT
<213> ORGANISM: Artificial Sequence
<220> FEATURE:
<223> OTHER INFORMATION: Synthetic peptide based on angiotensin
      precursor

<400> SEQUENCE: 133

Val Tyr Ile His Pro Phe
```

```
                1               5

<210> SEQ ID NO 134
<211> LENGTH: 15
<212> TYPE: PRT
<213> ORGANISM: Homo sapiens

<400> SEQUENCE: 134

Asp Arg Val Tyr Ile His Pro Phe His Leu Val Ile His Thr Glu
1               5                   10                  15

<210> SEQ ID NO 135
<211> LENGTH: 10
<212> TYPE: PRT
<213> ORGANISM: Homo sapiens

<400> SEQUENCE: 135

Asp Arg Val Tyr Ile His Pro Phe His Leu
1               5                   10

<210> SEQ ID NO 136
<211> LENGTH: 8
<212> TYPE: PRT
<213> ORGANISM: Homo sapiens

<400> SEQUENCE: 136

Asp Arg Val Tyr Ile His Pro Phe
1               5

<210> SEQ ID NO 137
<211> LENGTH: 7
<212> TYPE: PRT
<213> ORGANISM: Homo sapiens

<400> SEQUENCE: 137

Arg Val Tyr Ile His Pro Phe
1               5

<210> SEQ ID NO 138
<211> LENGTH: 6
<212> TYPE: PRT
<213> ORGANISM: Homo sapiens

<400> SEQUENCE: 138

Val Tyr Ile His Pro Phe
1               5

<210> SEQ ID NO 139
<211> LENGTH: 6
<212> TYPE: PRT
<213> ORGANISM: Artificial Sequence
<220> FEATURE:
<223> OTHER INFORMATION: Synthetic peptide based on angiotensin
      precursor

<400> SEQUENCE: 139

Val Tyr Ile His Pro Phe
1               5

<210> SEQ ID NO 140
<211> LENGTH: 6
<212> TYPE: PRT
<213> ORGANISM: Artificial Sequence
<220> FEATURE:
<223> OTHER INFORMATION: Synthetic peptide based on angiotensin
      precursor
```

```
<400> SEQUENCE: 140

Val Tyr Ile His Pro Phe
1               5

<210> SEQ ID NO 141
<211> LENGTH: 6
<212> TYPE: PRT
<213> ORGANISM: Artificial Sequence
<220> FEATURE:
<223> OTHER INFORMATION: Synthetic peptide based on angiotensin
      precursor

<400> SEQUENCE: 141

Val Tyr Ile His Pro Phe
1               5
```

C-MET RECEPTOR REGULATION BY ANGIOTENSIN IV (AT4) RECEPTOR LIGANDS

CROSS-REFERENCE TO RELATED APPLICATIONS

This application is a Continuation-in-Part (CIP), allowed U.S. patent application Ser. No. 11/972,487, filed Jan. 8, 2008, the complete contents of which is hereby incorporated by reference in entirety. Ser. No. 11/972,487 is a CIP of U.S. application Ser. No. 11/774,517, filed Jul. 6, 2007, and of PCT/US2007/15572, filed Jul. 6, 2007, each of which claims the benefit under 35 U.S.C. §119(e) of U.S. Provisional Patent Application No. 60/819,201 filed Jul. 7, 2006, the complete contents of each of which is hereby incorporated by reference in entirety.

BACKGROUND OF THE INVENTION

1. Field of the Invention

Embodiments of the invention disclosed herein relate generally to compositions and methods for altering hepatocyte growth factor activity or c-Met receptor activity. Certain aspects relate to the diagnosis, prevention or treatment of, as well as to general therapy of subjects having, suspected of having, or susceptible to, a condition associated with c-Met receptor dysregulation. C-Met receptor dysregulation may be a condition in which underactivity, overactivity or improper activity of a c-Met cellular or molecular event is present, including obesity or a condition associated with obesity, a hyperproliferative disorder, a condition characterized by abnormal angiogenesis, or alternatively, a condition characterized by vascular insufficiency such as may benefit from increased angiogenesis. Embodiments disclosed herein further relate to methods for identifying or modifying compounds useful for the diagnosis, prevention or treatment of such conditions associated with c-Met receptor dysregulation.

2. Background of the Invention

The classic renin-angiotensin system regulates cardiovascular function including blood pressure, electrolyte balance, reproduction, and may play a role in other physiological processes, including atherosclerosis. These angiotensin-mediated effects are believed primarily to operate through angiotensin (AT) receptors identified as $AT_1$ and $AT_2$ receptors. Renin, through its proteolytic activity, first cleaves the angiotensinogen precursor polypeptide to form angiotensin I. Next, angiotensin converting enzyme (ACE) enzymatically converts angiotensin I to angiotensin II; ACE has been detected in a variety of tissues including brain, kidney, adrenal glands, vasculature, heart and ovaries. ACE-generated angiotensin II (AT2 or $AT_2$) is subsequently cleaved (by aminopeptidase A) to form angiotensin III, which is cleaved by aminopeptidases N, M and/or B to form angiotensin IV (Val-Tyr-Ile-His-Pro-Phe, [SEQ ID NO:33]), (Mustafa et al., J. Renin Angiotens, Aldoster. Syst. 2(4):205-210, (2001), Thomas et al., Int. J. Biochem. & Cell Biol. 35: 774-779 (2003): McKinley et al., Int. J. Biochem. & Cell Biol. 35: 901-918 (2003).)

Angiotensin IV ($AT_4$ or AT4) has been shown to play a role in regulating disparate biological activities including blood flow, cognitive function, neuronal development, inflammation and behavior (Wright et al., Prog. Neurobiol. 72: 263-293 (2004); Kamar et al., Regul. Pept. 68: 131-138 (1997).) AT4 is believed to exert its biological effects through interaction with a cell surface receptor identified as the $AT_4$ receptor (AT(4)R), which is also known as the insulin-regulated membrane aminopeptidase (IRAP) (e.g., Chai et al., 2004 Cell. Mol. Life. Sci. 61:2728; Esteban et al., 2005 Circ. Res. 96:965; Albiston et al., 2001 J. Biol. Chem. 276:48623). AT(4)R/IRAP is a type II (see, e.g., Parks, 1996 J. Biol. Chem. 271:7187) integral membrane-spanning protein having aminopeptidase activity.

Many of the observed biological characteristics of the $AT_4$ system (e.g., the existence of both agonist and antagonist AT4 ligands), however, have been difficult to reconcile with the TRAP model for the $AT_4$ receptor. This discrepancy suggested that another unidentified protein(s) might be responsible for the action of $AT_4$ receptor ligands (Harding et al., 1994 Kidney Int. 46:1510; Wright et al., 2004 Prog. Neurobiol. 72:263). The molecular identity of the target $AT_4$ receptor that mediates a number of AT4 biological activities has, however, remained elusive.

Hepatocyte growth factor (HGF, e.g., 1991 Proc. Nat. Acad. Sci. USA 88:7001; Donate et al., 1994 Prot. Sci. 3:2378; GenBank Accession No. AAA64239 [SEQ ID NO:83], M73239.1 (728 amino acids)), also known as scatter factor (SF), is a noncovalent homodimeric polypeptide growth factor, assembled from naturally occurring monomeric HGF polypeptide subunits, that induces cell motility and cell proliferation, which may lead to normal processes of angiogenesis, or abnormal processes of tumor development or metastasis. HGF functions by binding to its cell surface receptor, c-Met, which is a receptor protein tyrosine kinase and a protooncogene product.

The c-Met receptor is a heterodimer composed of an alpha and beta chain (Maggiora et al., J. Cell Physiol. 173:183-186, (1997), Christensen et al., Can. Lett. 225: 1-26, (2005)). The c-Met receptor is enriched on vascular endothelial cells where it mediates the regulation of angiogenesis (Rosen et al., 1997 EXS 79:193). For instance, NK4, a large molecule c-Met inhibitor, has been shown previously to inhibit angiogenesis (Kuba et al., 2000 Cancer Res. 60:6737).

Upon activation, as may result from ligand engagement, the c-Met polypeptide (e.g., hepatocyte growth factor-receptor, HGF-R, also known as scatter factor receptor, SF-R, GenBank Acc. No. AAA59591, [SEQ ID NO:84]) induces mitogenic, motogenic and morphogenic responses by recruiting a number of signaling and docking molecules, and has been implicated in the phosphorylation of cell junction proteins (e.g., Zhang et al., 2003 J. Cell Biochem. 88:408; Miao et al., 2003 J. Cell Biol. 162:1281; Berdichevsky et al., 1994 J. Cell Sci. 107:3557). Ligand induced activation of c-Met by HGF/SF leads to the autophosphorylation of specific tyrosine residues within the c-Met receptor protein tyrosine kinase (PTK) domain (Furge et al. (2000) Oncogene 19, 5582-5589; Weidner et al. (1995) Proc Natl Acad Sci USA 92, 2597-2601) and to the association of various signaling proteins (e.g., Naldini et al., 1991 Mol. Cell. Biol. 1250:1085). A significant event in c-Met signaling is the association with the c-Met receptor of growth factor receptor bound protein 2, Grb2 associated binder (Gab1), a multi-functional scaffolding adapter (Birchmeier et al., 2003 Nat. Rev. Mol. Cell. Biol. 4:915). Gab1 association provides c-Met with multiple docking sites for a variety of intracellular signal transducers (Trusolino et al., 2002 Nat. Rev. Cancer 2:289).

Following activation by HGF/SF, c-Met is able to exert a variety of effects by recruiting docking and signaling molecules. Phosphorylation of the tyrosine residues in the activation loop of the PTK domain potentiates the intrinsic kinase activity of Met, whereas phosphorylation of the two docking site tyrosine residues ($Tyr^{1349}$, $Tyr^{1356}$) allows for the recruitment of adaptor molecules including Grb2, SHC and Gab1 and signaling enzymes including phosphotidylinositol 3-kinase (PI3K), phospholipase C.gamma. (PLC-.gamma.), the PTK src, the protein tyrosine phosphatase SHP2, as well as the transcription factor STAT3 (reviewed in Furge et al. (2000) Oncogene 19, 5582-5589).

The binding of HGF to the cell surface c-Met receptor thus results in multiple cell-signaling events that promote cell survival, cell proliferation, cell motility, disruption of the extracellular matrix (ECM), cell morphogenesis, angiogenesis and/or cell extravasation and colonization, for instance, as observed in tumor metastasis. (Jeffers et al., J. Mol. Med., 74: 505-513 (1996); Amicone et al., EMBO J. 16: 495-503 (1997); Matsumoto and Nakamura, Biochem. Biophys. Res. Comm 239: 639-644 (1997); Kirchhofer et al., J. Biol. Chem., 279: 39915-39924 (2004)). Disruption of normal signaling through c-Met has been implicated in certain cancers (e.g., Zhang et al., 2004 Cancer Cell 6:5; Christensen et al., 2005 Cancer Lett. 225:1-26; Ferraro et al., 2006 Oncogene 25:3689). For example, overexpression of HGF and/or of c-Met has been implicated in a number of cancers, including carcinomas, gliomas, and mesotheliomas. Particular organs affected include breast, pancreas, liver, lung, ovary, stomach, bile duct, kidney, and others, in part because of increased angiogenesis (Zbar et al., J. Urol., 151: 561-566 (1994); Date et al., FEBS Letters, 420:1-6 (1997)). In addition, several studies have indicated that cancer cells can be a significant source of HGF within a subject (e.g., Jiang et al., One. Hemat. 53: 35-69 (2005)).

Alterations (e.g., statistically significant increases or decreases) in the activity states of a number of intracellular signaling cascades thus characterize cellular responses to HGF binding by the cell surface c-Met receptor, including biological signal transduction pathways that comprise one or more of Grb2, cortactin, Arp2/3, WASP/Wave, Rho/rac, Rock, LIMK, PI1P5-K, ERM proteins, Dia-1, MLC phosphatase, cofilin, Ptdins(4,5)P2, cadherins (including E-cadherin), MMPs, fl-catenin, $p27^{kip1}$, SOS, Ras, Raf, MAPK, PI3K, NK B, src, JNK1, Bid/Bax, caspases, C-Myc, Bax, Mcl1, Bcl-w, Akt, FLICE, STATs (including STAT3), COX, ERK/paxillin, as well as others (see, e.g., Jiang et al., One. Hemat. 53: 35-69 (2005); Alberts et al., Molecular Biology of the Cell, 4th Ed., 2002, Garland Science, N.Y.). Activation of these intracellular messenger systems can lead to changes in a cell's cytoskeleton, adhesion state and adherens junctions, cell cycle, and directional cell movement, and may also contribute to altered activity in one or more of a number of other biochemical pathways that affect cellular metabolic, catabolic, biosynthetic, respiratory, gene expression, membrane dynamic or other functions or phenotypes. Thus, such HGF-c-Met binding events may lead to or contribute to cancer development, tumor cell growth or metastasis, altered angiogenesis, or other physiologically significant outcomes.

Angiogenesis, the process of blood vessel formation, is necessary for proper wound healing and repair, as well as playing an important role during embryonic, fetal and young animal development, and continuing on to adulthood. Dysfunction in the course of angiogenic processes at any of these stages may result in certain detrimental health conditions, including, for instance, ischemic heart disease, preeclampsia, neurodegeneration, and/or respiratory distress (e.g., as the result of an inadequate or insufficient level of angiogenesis relative to the levels seen in unafflicted individuals), and also including, for example, malignant metastasis, arthritis, macular degeneration, diabetic retinopathy, ocular and inflammatory disorders, obesity, asthma, diabetes, cirrhosis, multiple sclerosis, endometriosis, AIDS, bacterial infections, and/or autoimmune diseases (e.g., as the result of an excessive or overabundant level of angiogenesis relative to the levels seen in unafflicted individuals). See, e.g., Carmeliet, Nature 438: 932-936 (2005). Intervention to alter (e.g., increase or decrease in a statistically significant manner) angiogenesis in these and other conditions remains a useful but incompletely fulfilled goal.

Of the conditions relating to dysfunction in angiogenesis as described above, obesity is one in which adipose tissue formation, or adiposity, is increased to a point where it is associated with certain clinically defined health conditions or increased mortality. Although obesity is an individual clinical condition, it is increasingly viewed as a serious and growing public health problem, as excess adipose tissue is accompanied by a dramatically increased risk for the development of numerous recognized health problems, including insulin resistance and type 2 diabetes mellitus, impaired glucose tolerance, non-alcoholic fatty liver disease, dyslipidemia (characterized by elevated levels of nonesterified fatty acids (NEFAs), triglycerides, and small dense LDL particles, along with reduced levels of HDL), hypertension, coronary heart disease, increased inflammatory activity, and thrombosis (Bray J. Clin. Endocrinol. Metab. 89:2583-89 (2004); Glass and Witstum, Cell 104:503-516 (2001)). These diseases are associated primarily with an increased number of fat cells.

Other conditions associated with excess adipose tissue formation, and which may therefore be associated with obesity, relate in particular to increased fat mass, including immobility, osteoarthritis, respiratory conditions such as dyspnea and obstructive sleep apnea, and psychological problems such as depression and social stigmatization. A relationship has also been identified between obesity and the incidence of certain cancer types, such as breast cancer (Calle and Kaaks, Nat. Rev. Cancer 4:579-591 (2004); and lyengar et al., Oncogene 22:6408-6423 (2003)), in addition to endometrial, colorectal, kidney, prostate, gallbladder, pancreatic and esophageal cancers (See Vainio and Bianchini, IARC handbooks of cancer prevention. Volume 6: Weight control and physical activity. Lyon, France: IARC Press, 2002); Abu-Abid et al., J Med 33:73-86 (2002); and Giovannucci, Gastroenterology 132: 2208-25 (2007)).

Angiogenesis regulates the growth and maintenance of adipose tissue, which is a highly vascularized tissue. Neovascularization is a feature of adipose tissue expansion (e.g., adipogenesis) as well as of adipose tissue maintenance, suggesting that adipose tissue viability is sustained by a constant vascular remodeling process (Dallabrida et al., Biochem. Biphys. Res. Commun. 311:563-571 (2003)). As one particular example of this phenomenon, vascular endothelial growth factor (VEGF) expression and resulting angiogenesis may augment or precipitate adipogenesis in white and brown adipose tissues (Hausman and Richardson, J. Anim. Sci. 82:925-34 (2004)).

Angiogenesis regulatory proteins may provide relevant, therapeutic targets for controlling adipose tissue formation, and in particular, angiogenesis inhibitors may be useful in reducing obesity and its associated health problems (Liu and Meydani, Nutrition Reviews 61:384-387 (2003)). For example, systemic treatment of obese mammals with anti-angiogenic agents has been shown to induce a loss of white adipose tissue (Rupnick et al. PNAS USA 99:10730-35 (2002). In particular, TNP-470, a selective inhibitor of endothelial growth and angiogenesis, and other angiogenesis inhibitors such as endostatin, angiostatin, thalomide, and leptin, have all been shown to reduce obesity in mice (Id.; and Brakenhielm et al., Circulation Research 94:1579-1588 (2004)).

While intervention strategies that target angiogenic regulatory factors would therefore appear useful for controlling adiposity, and thus obesity, systemically delivered anti-angiogenic agents do not exhibit sufficient specificity for adipose tissue to provide a practical therapeutic modality. Accordingly, there is a need in the art to identify molecular targets in angiogenic pathways that would provide increased specificity for adipose tissues.

HGF, in particular, regulates angiogenesis in adipose tissue, and thus regulates adiposity. In fact, obesity is associated with elevated levels of circulating HGF (Rehman et al., Journal of the American College of Cardiology 41:1408-13 (2003), and adipose tissue has been shown to produce HGF, thereby contributing specifically to such elevated HGF levels (Bell et al., Am J Physiol Endocrinol Metab 291:E843-E848 (2006). In addition, in vivo silencing of HGF expression in preadipocytes decreases the ability of these cells to recruit endothelial cells for angiogenesis, whereas elevated HGF expression in preadipocytes enhances endothelial cell migration into fat tissue (Bell et al., Am J Physiol Endocrinol Metab (in press, 2007). HGF is thus a potent mitogenic and angiogenic factor that is produced in human adipose tissue, and that plays a central role in adipose tissue angiogenesis.

Highlighting the relationship between obesity and cancer, as noted above, aberrant HGF expression is also implicated in many types of cancer. By way of example, a number of tumors, including melanomas, hepatomas, and carcinomas of the breast, exhibit inappropriate expression of HGF, and HGF overexpression in transgenic mice results in neoplasms of the liver, mammary gland, skeletal muscle, and melanocytes (Jabubczak et al., Mol Cell Biol 18:1275-83 (1998). Targeting of the HGF pathway, alone or in combination with standard therapies, is being considered as a means of improving current therapies in certain types of malignancies (Sattler and Salgia, Curr Oncol Rep 9:102-8 (2007)). The presence of elevated HGF expression in both obesity and certain types of cancer represents a potential therapeutic nexus between these two significant public health problems.

HGF appears to be a critical regulator of neural stem cell expansion and differentiation (Nicoleau et al., 2009) suggesting that neural as well as many types of peripheral stem cells are under the control of the HGF/c-Met system. HGF has been shown to be a potent neurotrophic factor (Ieraci et al., 2002; Kato et al., 2009) in many brain regions and to be particularly effective as a pro-survival/regenerative factor for motoneurons (Kitamura et al., 2011), hippocampal neurons (Lin and Walikonis, 2008), cerebellar granular cells (Ieraci et al., 2002), and sympathetic neurons (Maim and Klein, 1999). The neuroprotective effect of the HGF on the nigrostriatal pathway may be credited to its role in stem cell regulation (review, Nakamura et al., 2011), its effect on the development of tubular structures (Santos et al., 1993) and its general proliferative, anti-apoptotic, motogenic, and morphogenic actions on many cell types including hepatocytes and cells of epithelial origin (Bai et al. (2012). The use of HGF may thus also be applicable to a variety of neurological diseases and conditions, several of which are described in the following paragraphs.

Dementia

There are approximately 10 million diagnosed dementia patients in the United States alone and that number continues to grow every year as the population ages. The costs of treatment and care of these patients are in excess of $70 billion annually and are increasing rapidly. Unfortunately, the current treatment options for the management of dementia are severely limited and largely ineffective. The lack of treatment options for a burgeoning health problem of this magnitude necessitates that new and innovative therapeutic approaches be developed as quickly as possible.

At its core dementia results from a combination of diminished synaptic connectivity among neurons and neuronal death in the entorhinal cortex, hippocampus and neocortex. Therefore, an effective treatment would be expected to augment synaptic connectivity, protect neurons from underlying death inducers, and stimulate the replacement of lost neurons from preexisting pools of neural stem cells. These clinical endpoints advocate for the therapeutic use of neurotrophic factors, which mediate neural development, neurogenesis, neuroprotection, and synaptogenesis. Not unexpectedly neurotrophic factors have been considered as treatment options for many neurodegenerative diseases including Alzheimer's disease (Fafalios et al., 2011); Kitamura et al., 2011).

Amyotrophic Lateral Sclerosis (ALS)

ALS is a fatal rapid-onset neurodegenerative disease that is characterized by degeneration of motoneurons in the spinal cord and efferent neurons in the motor cortex and brainstem. The impact of this degeneration results in a progressive loss of muscle function culminating in total paralysis. Approximately 90% of the cases of ALS are classified as sporadic with no known etiology, while the remaining 10% appear to be familial, resulting in part from defects in copper/zinc superoxide dismutase 1 (SOD1), which leads to exaggerated oxidative stress and an unfolded protein response. The one thing that both forms of ALS have in common is that there is currently is no effective treatment.

Despite the paucity of effective treatment options, several studies have highlighted the potential benefits of using hepatocyte growth factor (HGF) as a therapeutic agent. These investigations have demonstrated that application of hepatocyte growth factor (HGF) in a murine or rat model of familial ALS significantly slows motoneuron degeneration (Fafalios et al., 2011); reduces gliosis (Kitamura et al. 2011), which contributes to the degeneration process; delays the onset of paralysis (4); and increases lifespan (Fafalios et al. 2011).

Parkinson's Disease

A treatment option long considered for many neurodegenerative diseases including Parkinson's disease (PD) has been the application of growth factors with the intention of halting disease progression, restoring lost function, or hopefully both (Rangasamy et al., 2010). However, this objective has gone largely unfulfilled at the level of clinical medicine because of limitations related to brain delivery and costs. Growth factors are universally large proteins that are both metabolically labile and too large to pass the blood-brain barrier (BBB). As such, most approaches to delivery have utilized gene therapy methods with the hope that the growth factor will be expressed in the correct location at a high enough concentration and for a long enough period to provide clinical relief. Although a number of creative and successful approaches in animal models have been employed to deliver growth factors like GDNF (Wang et al., 2011) to the brain, these methodologies are technically complex and prohibitively difficult to bring to practice with large numbers of patients.

The potential utility of HGF as a PD treatment has been highlighted in a study by Koike et al. (2006) in which an HGF plasmid injected directly into the substantia nigra (SN) resulted in localized over-expression of HGF, and acted dramatically to prevent neuronal cell death and preserve normal motor function in the 6-hydroxydopamine (6-OHDA) PD rat model. This observed neuroprotective effect of HGF on dopaminergic (DA) neurons meshes with its ability to augment the proliferation and migration of dopaminergic progenitor cells (Lan et al., 2008).

Traumatic Brain Injury (TBI)/Spinal Cord Injury

TBI often negatively impacts cognitive function and can elicit effects that range from mild, with temporary decrements in mental abilities, to severe, with prolonged and debilitating cognitive dysfunction (Kane et al., 2011). Cognitive difficulties along with other neurological deficits including: anxiety, aggressiveness, and depression result in a significantly reduced quality of life (Masel and DeWitt, 2010). With military operations concluded in Iraq and continuing in Afghanistan TBI has become the major combat injury at 28% of all combat casualties (Okie, 2005; U.S. Medicine, May 2006, Vol 42). Total estimates of military service members suffering TBIs between 2001 and 2010 range from 180,000 to 320,000 (U.S. Defense and Veterans Brain Injury Center).

Underlying TBI is physical injury to the brain resulting in decreased synaptic connectivity among neurons, loss and death of neurons, damage to cerebral blood vessels resulting in ischemic/hypoxic-induced damage, and secondary glial scaring. This loss of neurons and diminished synaptic connectivity is particularly apparent in the hippocampus (Gao et al., 2011; Zhang et al., 2011a; Zhang et al., 2011b) resulting in defective long-term potentiation (Schwarzbach et al., 2006) and cognitive deficits (e.g. Dikmen et al., 2009). The prevalence of TBI associated injuries that result in neuronal loss and decreased synaptic connectivity denote the need for therapies which support neuronal repair and/or replacement. These clinical endpoints advocate for the therapeutic use of neurotrophic factors such as HGF which mediate neural development, neurogenesis, neuroprotection, and synaptogenesis, for treating TBI. Neurotrophic factors have been considered as treatment options for TBI (Kaplan et al., 2010; Richardson et al., 2010; Qi et al., 2011). Further, recent studies have demonstrated that HGF given intrathecially reduces tissue damage and promotes functional recovery in a non-human primate spinal cord injury model when it is delivered after injury (Kitamura et al., 2011). HGF prevented glial scarring, an impediment to axon regrow, while at the same time stimulating the regrowth process.

Multiple Sclerosis

HGF derived from mesenchymal stem cells (MSCs) has recently been shown to reduce functional deficits in mouse MOG(35-55)-induced experimental autoimmune encephalomyelitis (EAE) and promote the development of oligodendrocytes and neurons resulting in enhanced neural cell development and remyelination (Bai et al., 2012). These data strongly indicate that HGF mediates functional recovery in a standard multiple sclerosis model and thus suggest that augmented HGF function may have significant therapeutic benefits in MSC multiple sclerosis patients.

Unfortunately, the direct use of HGF or any other protein neurotrophic factor as a therapeutic agent has serious limitations. For example, HGF is manufactured by recombinant methods at a very high cost, severely limiting its widespread use. With respect to neurological disorders in particular, the large size and hydrophilic character of HGF preclude blood-brain barrier permeability (BBB). Accordingly, there is a need in the art for low cost, readily administrable and yet effective compounds and compositions that are capable of specifically and selectively regulating HGF activity in vivo.

SUMMARY OF THE INVENTION

By advancing the understanding of biological signal transduction mechanisms that operate through the HGF/c-Met receptor pathway, the present invention provides compositions and methods of use of therapeutic molecules based on HGF which do not suffer from the limitations exhibited by HGF, and which can be used in vivo for the treatment of the various diseases and conditions associated with HGF.

The invention provides a method for treating or preventing a neurological disease or disorder in a subject in need thereof, comprising administering to a subject a pharmaceutical composition that comprises an isolated angiotensin-like factor, wherein the angiotensin-like factor is capable of specifically binding to the cell surface c-Met receptor, and thereby treating or preventing said neurological disease or disorder, said angiotensin-like factor being selected from: (a) a polypeptide of no more than 20, 19, 18, 17, 16, 15, 14, 13, 12, 11, 10, 9, 8, 7, 6, 5, 4 or 3 amino acids, or a peptidomimetic thereof, of general formula I: N-$X_1$-$X_2$-$X_3$-C [I] wherein: N is an amino terminus of the peptide or peptidomimetic and consists of 0, 1, 2, 3, 4, 5, 6, 7, 8, 9, 10, 11, 12, 13, 14, 15, 16 or 17 amino acids that are independently selected from natural and non-natural amino acids, C is a carboxy terminus of the peptide or peptidomimetic and consists of 0, 1, 2, 3, 4, 5, 6, 7, 8, 9, 10, 11, 12, 13, 14, 15, 16 or 17 amino acids that are independently selected from natural and non-natural amino acids, $X_1$ is phenylalanine, tryptophan or tyrosine, $X_2$ is isoleucine, leucine, alanine, valine, phenylalanine, proline, methionine or tryptophan, and $X_3$ is lysine, arginine or histidine; (b) a polypeptide of no more than 20, 19, 18, 17, 16, 15, 14, 13, 12, 11, 10, 9, 8, 7, 6, 5, 4 or 3 amino acids, or a peptidomimetic thereof, of general formula I: N-$X_1$-$X_2$-$X_3$-C [I] wherein: N is an amino terminus of the peptide or peptidomimetic and consists of 0, 1, 2, 3, 4, 5, 6, 7, 8, 9, 10, 11, 12, 13, 14, 15, 16 or 17 amino acids that are independently selected from natural and non-natural amino acids, C is a carboxy terminus of the peptide or peptidomimetic and consists of 0, 1, 2, 3, 4, 5, 6, 7, 8, 9, 10, 11, 12, 13, 14, 15, 16 or 17 amino acids that are independently selected from natural and non-natural amino acids, $X_1$ is a natural or non-natural amino acid having an aromatic side chain, $X_2$ is a natural or non-natural amino acid having a hydrophobic side chain, and $X_3$ is a natural or non-natural amino acid having a basic side chain; (c) a polypeptide of no more than 20, 19, 18, 17, 16, 15, 14, 13, 12, 11, 10, 9, 8, 7, 6, 5, 4 or 3 amino acids, or a peptidomimetic thereof, said polypeptide comprising (i) a tripeptide having an amino acid sequence that is selected from: Lys-Asp-Tyr, Leu-Asp-Tyr, Asp-Tyr-Ile, Tyr-Ile-Arg, Ile-Arg-Asn, and Arg-Asn-Cys, and (ii) at least one of an amino terminus and a carboxy terminus, each of said amino terminus and said carboxy terminus consisting of 0, 1, 2, 3, 4, 5, 6, 7, 8, 9, 10, 11, 12, 13, 14, 15, 16 or 17 amino acids that are independently selected from natural and non-natural amino acids; (d) the polypeptide or peptidomimetic of (a) which comprises the amino acid sequence Nle-Tyr-Leu-Ψ-His-Pro-Phe as set forth in SEQ ID NO:43, wherein Ψ consists of a reduced peptide bond of formula II: —$CH_2$—$NH_2$— [III]; and (e) the polypeptide or peptidomimetic of (b) which comprises at least one amino acid sequence selected from SEQ ID NOS: 9, 25, 33, 41, 42, 45-50, 52-80 and 81.

In some embodiments, the angiotensin-like factor inhibits (and in certain embodiments competitively inhibits) binding of a native HGF hinge region polypeptide to a cell surface c-Met receptor, said native HGF hinge region polypeptide comprising the amino acid sequence Lys-Asp-Tyr-Ile-Arg-Asn-Cys [SEQ ID NO:82], wherein the angiotensin-like factor is capable of specifically binding to at least one of the HGF polypeptide and the cell surface c-Met receptor in the subject, and thereby treating or preventing said neurological disease or disorder.

The invention also provides a method for treating or preventing a neurological disease or disorder in a subject in need thereof, comprising administering to the subject a therapeutically effective amount of a pharmaceutical composition that comprises an isolated angiotensin-like factor, said angiotensin-like factor being selected from: (a) a polypeptide of 15, 14, 13, 12, 11, 10, 9, 8, 7, 6, 5, 4, 3 or 2 amino acids, or a peptidomimetic thereof, said polypeptide comprising a peptide having at least one amino acid sequence that is selected from: Lys-Asp, Asp-Tyr, Tyr-Ile, Ile-Arg, Arg-Asn, Asn-Cys, Lys-Asp-Tyr, Asp-Tyr-Ile, Tyr-Ile-Arg, Ile-Arg-Asn, Arg-Asn-Cys, Lys-Asp-Tyr-Ile [SEQ ID NO: 86], Asp-Tyr-Ile-Arg [SEQ ID NO: 87], Tyr-Ile-Arg-Asn [SEQ ID NO: 88], Ile-Arg-Asn-Cys [SEQ ID NO: 89], Lys-Asp-Tyr-Ile-Arg [SEQ ID NO: 90], Asp-Tyr-Ile-Arg-Asn [SEQ ID NO: 91], Tyr-Ile-Arg-Asn-Cys [SEQ ID NO: 92], Lys-Asp-Tyr-Ile-Arg-Asn [SEQ ID NO: 93], Asp-Tyr-Ile-Arg-Asn-Cys [SEQ ID NO: 94], Lys-Asp-Tyr-Ile-Arg-Asn-Cys [SEQ ID NO:82], Gly-Asp-Tyr-Ile-Arg-Asn-Cys [SEQ ID NO: 95], Lys-Gly-Tyr-Ile-Arg-Asn-Cys [SEQ ID NO: 96], Lys-Asp-Gly-Ile-Arg-Asn-Cys [SEQ ID NO: 97], Lys-Asp-Tyr-Gly-Arg-Asn-Cys [SEQ ID NO: 98], Lys-Asp-Tyr-Ile-Gly-Asn-Cys [SEQ ID NO: 99], Lys-Asp-Tyr-Ile-Arg-Gly-Cys [SEQ ID NO: 100] Lys-Asp-Tyr-Ile-Arg-Asn-Gly [SEQ ID NO: 101], (D)-Lys-Asp-Tyr-Ile-Arg-Asn-Cys [SEQ ID NO: 102], Lys-(D)-Asp-Tyr-Ile-Arg-Asn-Cys [SEQ ID NO: 103], Lys-Asp-(D)-Tyr-Ile-Arg-Asn-Cys [SEQ ID NO: 104], Lys-Asp-Tyr-(D)-Ile-Arg-Asn-Cys [SEQ ID NO: 105], Lys-Asp-Tyr-Ile-(D)-Arg-Asn-Cys [SEQ ID NO: 106], Lys-Asp-Tyr-Ile-Arg-(D)-Asn-Cys [SEQ ID NO: 107], and Lys-Asp-Tyr-Ile-Arg-Asn-(D)-Cys [SEQ ID NO: 108], (b) the polypeptide or peptidomimetic thereof of (a) wherein the peptidomimetic of said polypeptide comprises 1, 2, 3, 4, 5 or 6 reduced peptide bonds, each of said peptide bonds having the formula $CH_2$—$NH_2+$, (c) the polypeptide or peptidomimetic thereof of (b) wherein the peptidomimetic is selected from: Lys-Ψ-Asp-Tyr-Ile-Arg-Asn-Cys [SEQ ID NO: 109], Lys-Asp-Ψ-Tyr-Ile-Arg-Asn-Cys [SEQ ID NO: 110], Lys-Asp-Tyr-Ψ-Ile-Arg-Asn-Cys [SEQ ID NO: 111], Lys-Asp-Tyr-Ile-Ψ-Arg-Asn-Cys [SEQ ID NO: 112], Lys-Asp-Tyr-Ile-Arg-Ψ-Asn-Cys [SEQ ID NO: 113], Lys-Asp-Tyr-Ile-Arg-Asn-Ψ-Cys [SEQ ID NO: 114], Lys-Ψ-Asp-Ψ-Tyr-Ile-Arg-Asn-Cys [SEQ ID NO: 115], Lys-Ψ-Asp-Tyr-Ψ-Ile-Arg-Asn-Cys [SEQ ID NO: 116], Lys-Ψ-Asp-Tyr-Ile-Ψ-Arg-Asn-Cys [SEQ ID NO: 117], Lys-Ψ-Asp-Tyr-Ile-Arg-Ψ-Asn-Cys [SEQ ID NO: 118], Lys-Ψ-Asp-Tyr-Ile-Arg-Asn-Ψ-Cys [SEQ ID NO: 119], Lys-Asp-Ψ-Tyr-Ψ-Ile-Arg-Asn-Cys [SEQ ID NO: 120], Lys-Asp-Ψ-Tyr-Ile-Ψ-Arg-Asn-Cys [SEQ ID NO: 121], Lys-Asp-Ψ-Tyr-Ile-Arg-Ψ-Asn-Cys [SEQ ID NO: 122], Lys-Asp-Ψ-Tyr-Ile-Arg-Asn-Ψ-Cys [SEQ ID NO: 123], Lys-Asp-Tyr-Ψ-Ile-Ψ-Arg-Asn-Cys [SEQ ID NO: 124], Lys-Asp-Tyr-Ψ-Ile-Arg-Ψ-Asn-Cys [SEQ ID NO: 125], Lys-Asp-Tyr-Ψ-Ile-Arg-Asn-Ψ-Cys [SEQ ID NO: 126], Lys-Asp-Tyr-Ile-Ψ-Arg-Ψ-Asn-Cys [SEQ ID NO: 127], Lys-Asp-Tyr-Ile-Ψ-Arg-Asn-Ψ-Cys [SEQ ID NO: 128], and Lys-Asp-Tyr-Ile-Arg-Ψ-Asn-Ψ-Cys [SEQ ID NO: 129], wherein Ψ is a peptide bond having the formula $CH_2$—$NH_2+$, and (d) a polypeptide of 15, 14, 13, 12, 11, 10, 9, 8, 7, 6, 5, 4, 3 or 2 amino acids, or a peptidomimetic thereof, of general formula III: N-$X_1$-$X_2$-$X_3$-$X_4$-$X_5$-$X_6$-$X_7$-C [SEQ ID NO: 130] [III] wherein: N is an amino terminus of the peptide or peptidomimetic and consists of 0, 1, 2, 3, 4, 5, 6, 7, 8, 9, 10, 11, 12, or 13 amino acids that are independently selected from natural and non-natural amino acids, C is a carboxy terminus of the peptide or peptidomimetic and consists of 0, 1, 2, 3, 4, 5, 6, 7, 8, 9, 10, 11, 12, or 13 amino acids that are independently selected from natural and non-natural amino acids, $X_1$ is nothing, Lys, Arg, His, Norleucine or hexanoic acid, $X_2$ is nothing, Asp or Glu, $X_3$ is nothing, Tyr, Phe or homo-Phe, $X_4$ is nothing, Ile, Leu, Val, Phe, Met or Norleucine, $X_5$ is nothing, Arg, Lys or His, $X_6$ is nothing, Asn or Gln, and $X_7$ is nothing, Cys or Cys-amide.

In some embodiments, the angiotensin-like factor inhibits (and in certain embodiments competitively inhibits) binding of a native HGF hinge region polypeptide to a cell surface c-Met receptor, said native HGF hinge region polypeptide comprising the amino acid sequence Lys-Asp-Tyr-Ile-Arg-Asn-Cys [SEQ ID NO:82], wherein the angiotensin-like factor is capable of specifically binding to at least one of the HGF polypeptide and the cell surface c-Met receptor in the subject, and thereby treating or preventing said neurological disease or disorder.

These and other aspects of the invention will be evident upon reference to the following detailed description and attached drawings. All of the U.S. patents, U.S. patent application publications, U.S. patent applications including U.S. Ser. No. 60/819,201 (filed Jul. 7, 2006), U.S. Ser. No. 11/774,517 (filed Jul. 6, 2007), PCT/US2007/15572 (filed Jul. 6, 2007), foreign patents, foreign patent applications and non-patent publications referred to in this specification and/or listed in the Application Data Sheet, are incorporated herein by reference in their entirety, as if each was incorporated individually. Aspects of the invention can be modified, if necessary, to employ concepts of the various patents, applications and publications to provide yet further embodiments of the invention.

Figures 5A, 5B:
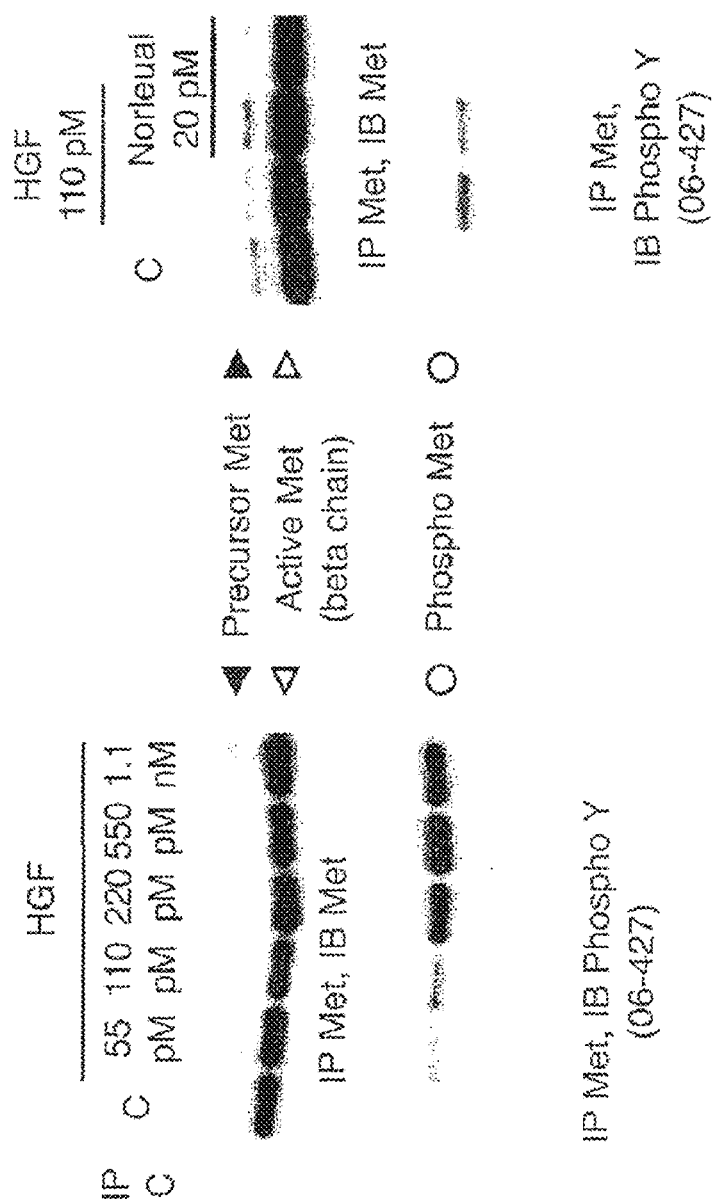
Figures 5E, 5F, 5G:
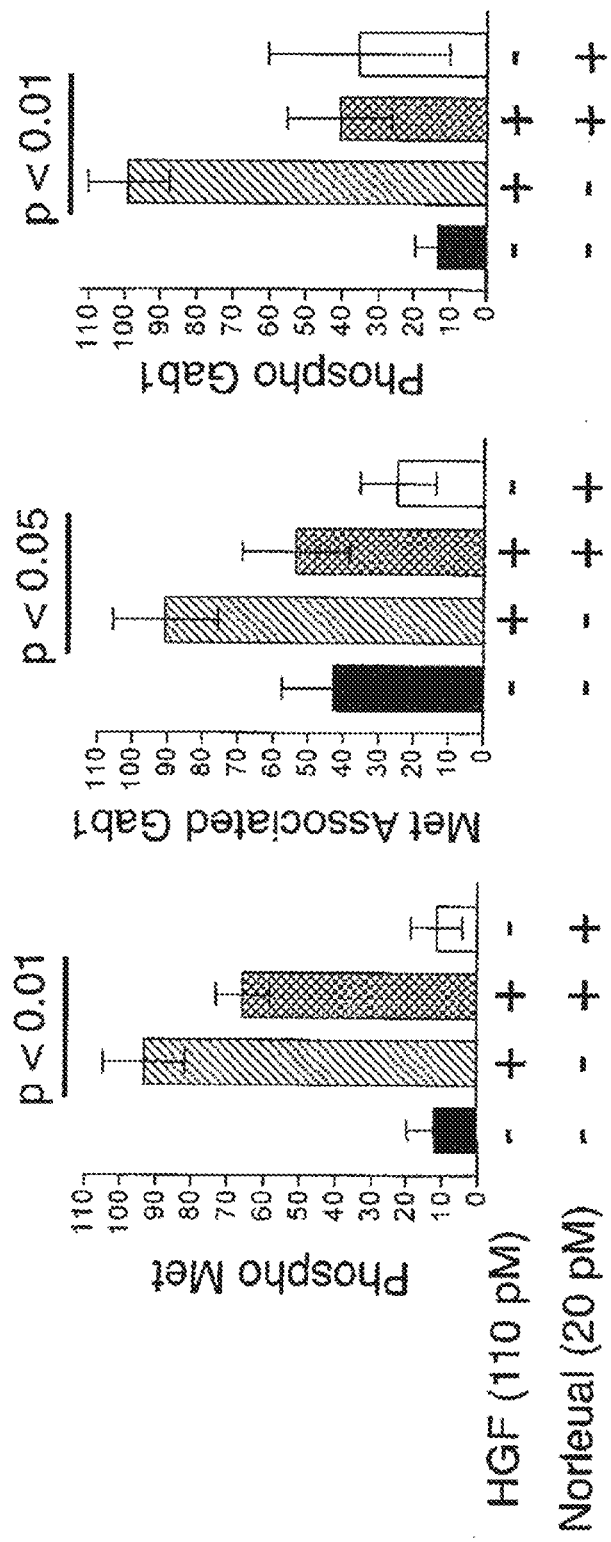

FIG. 5 shows that Norleual (Compound 2, SEQ ID NO:43) inhibited HGF-dependent c-Met phosphorylation and Gab1 association and phosphorylation in vitro. (FIG. 5A) HEK293 cells were treated for 10 minutes with HGF at indicated concentrations. Lysates were immunoprecipitated (IP) with anti-c-Met antibody (DO-24) and immunoblotted (IB) with anti-c-Met or anti-phospho-tyrosine (06-427) antibody. (FIG. 5B) HEK293 cells were treated for 10 minutes with HGF and/or Norleual. Lysates were IP with anti-c-Met (DO-24) and IB with anti-c-Met (DQ-13) or anti-phospho-tyrosine (HAM 1676). (FIG. 5C) HEK293 lysates were IP with anti-c-Met (DO-24) and IB with anti-Gab1. (FIG. 5D) HEK 293 lysates were IP with anti-Gab1 and IB with anti-Gab1 or anti-phospho-tyrosine (HAM 1676). (FIGS. 5E, 5F, 5G) Relative amounts (normalized to % total c-Met in IP) of quantified IP/IB band intensities for control, 110 pM HGF-, 110 pM HGF and 20 pM Norleual-, and 20 pM Norleual-treated HEK293 cells for phospho-c-Met (FIG. 5E, n=4), phospho-Gab1 (FIG. 5F, n=4), and c-Met associated Gab1 (FIG. 5G, n=3). Error bars indicate +/−SD.

Figure 6:
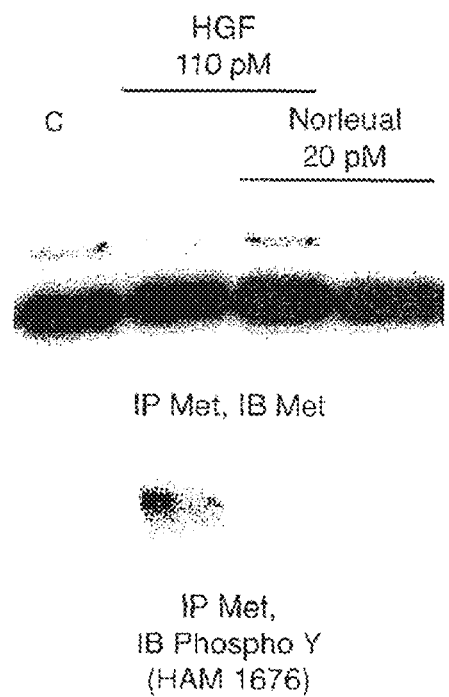

FIG. 6 shows Norleual (Compound 2, SEQ ID NO:43) inhibition of HGF-dependent Gab1 phosphorylation in vitro. HEK293 cells were treated for 10 minutes with HGF and/or Norleual at the indicated concentrations. Lysates were IP with anti-c-Met (DO-24, Millipore/Upstate, Billerica, Mass.) and IB with anti-c-Met (DQ-13, Millipore/Upstate) or anti-phosphotyrosine (HAM1676, lot JLB03, R&D Systems, Inc., Minneapolis, Minn.). Longer film exposures revealed bands with at approximate molecular weight of 100 kDa, the molecular weight of Gab1.

Figure 7:
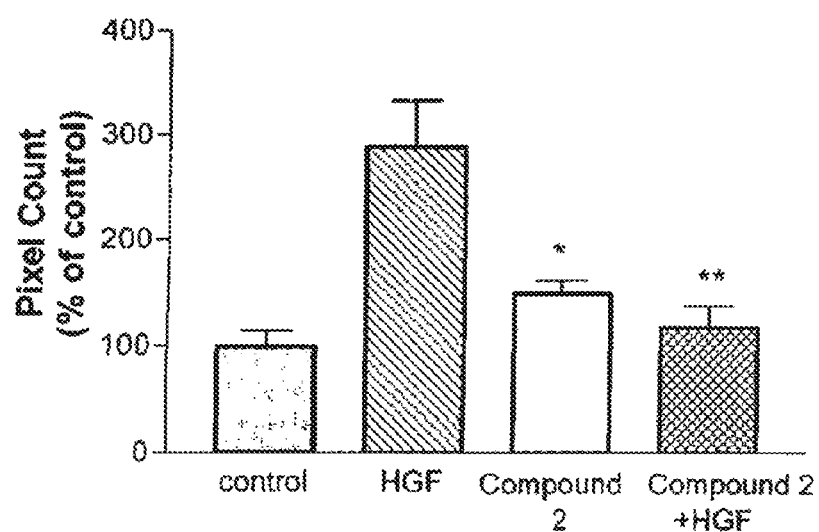

FIG. 7 illustrates the ability of Compound 2 (SEQ ID NO:43) to inhibit HGF-dependent cell scattering in MDCK cells.

Figure 8A:
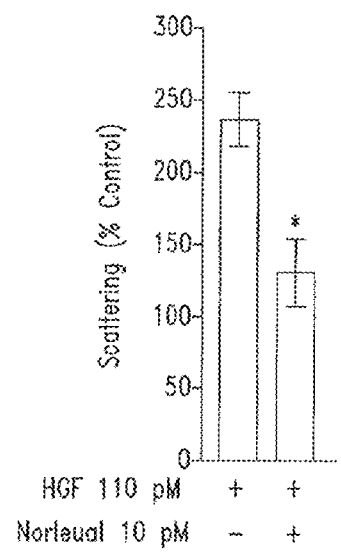
Figure 8B:
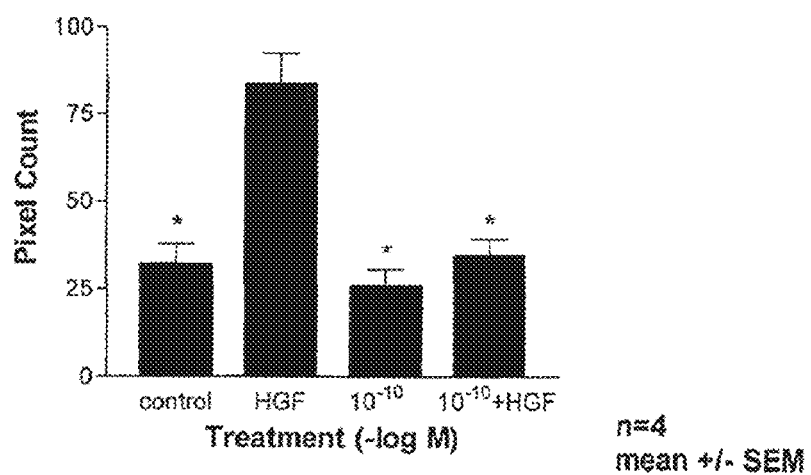

FIG. 8 shows inhibition by Norleual (Compound 2, SEQ ID NO:43) of HGF-induced cell scattering in MDCK cells. FIG. 8A: Confluent MDCK cells on coverslips were treated with HGF (110 pM), or HGF (110 pM)+Norleual (100 pM) for 48 hours. Digital images of top, bottom, left, and right sectors were acquired and the scattering of cells In each digital image was scored in blinded fashion and normalized to control scores. The difference between HGF and HGF+Norleual groups was significant (*p=0.0245, n=3). Error bars indicate +/−SEM. FIG. 8B: MDCK cells were plated on 6 mm diameter coverslips in DMEM 10% FBS and grown to 100% confluency. The coverslips were then transferred to fresh 6 well plates and the cells were serum-deprived for 24 hours to synchronize the cells in the same growth state. Thereafter, the 20 ng/ml of HGF alone and in the presence of $10^{-10}$ M Norleual in a 1% FBS DMEM was added to the cells. The cells were allowed scatter off of the coverslip for 24 hours before being fixed with 100% methanol for 15 minutes followed by staining with Diff-Quik (Dade-Behring). The coverslip was then removed to reveal the ring of cells that had scattered off of the coverslip and onto the plate. This ring was photographed and loaded on to NIH image J. Using NIH image J, the pixel count was determined for each ring. One-way ANOVA with tukey's post-hoc analysis was used to determine differences between the treatments (Prism® software, GraphPad, San Diego, Calif.). * indicates p<0.001 vs. HGF treatment. N=4, mean+/−SEM.

Figure 9A:
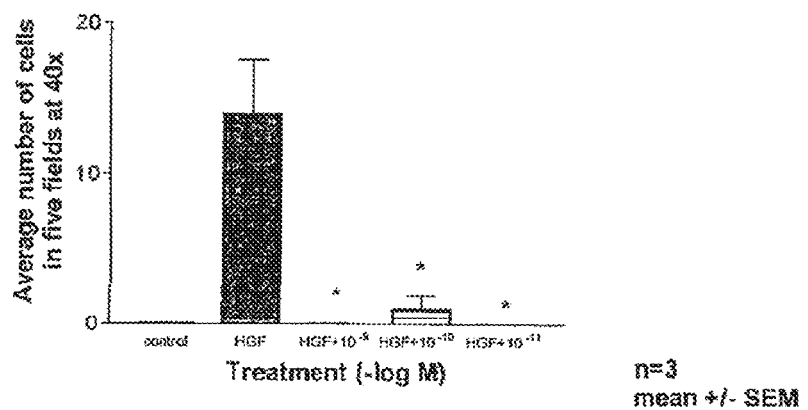
Figure 9B:
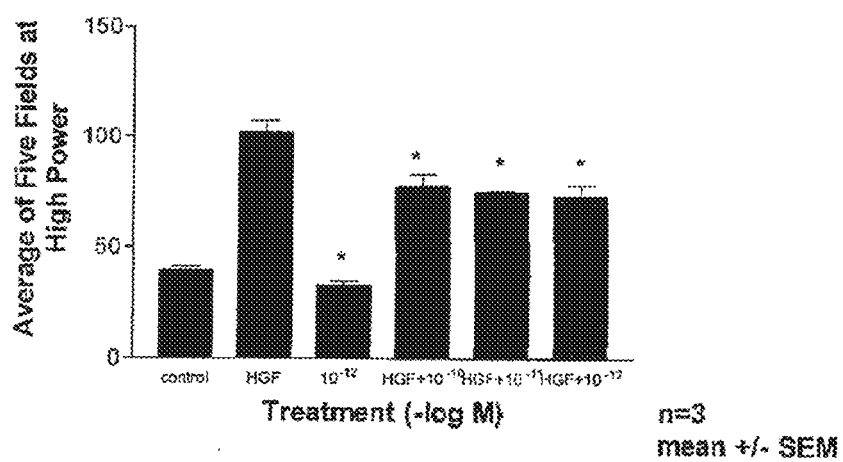

FIG. 9 shows inhibition by Norleual of HGF-induced c-Met-mediated MDCK Cell Collagen Invasion. FIG. 9A: Modulation of HGF stimulated MDCK cell collagen I invasion in the COSTAR® TRANSWELL® (permeable support device) chamber invasion assay. 50 µl of collagen I was added to the top chamber of the TRANSWELL® (permeable support device) chamber (BD Biosciences) and gelled by adjusting it to a physiological pH with a 1:1:1 mixture of 10.times. Modified Eagle's Medium, 1 M sodium bicarbonate, and 0.1 M sodium hydroxide for 30 minutes at 37° c. 50,000 MDCK cells in 1% FBS DMEM were seeded into the inside of the top chamber over the gelled collagen I solution and allowed to attach for two hours at 37° C. After the cells had attached to the collagen 1, the indicated concentrations of Notional were added to the top chamber. Additionally, 300 µl of 20 ng/ml HGF alone and with $10^{-9}$ M, $10^{-10}$ M, and $10^{-11}$ M Norleual was added to the bottom chamber to stimulate invasion through the collagen 1. The cells were allowed to invade the collagen for twelve hours before they were fixed and stained with Diff-Quik (Dade-Behring). The cells that had invaded the collagen and migrated to the underside of the membrane were counted in five random fields at 40× on as light microscope. The effect of treatment was determined using the one-way ANOVA with tukey's post-hoc analysis (PRISM® statistical analysis software). * indicates p<0.01 vs. HGF alone treatment. N=3 per treatment, mean+/−SEM, FIG. 9B: 50,000 MDCK cells in 1% FBS DMEM were seeded into the inside of the top chamber and allowed to attach for two hours at 37° C. After the cells had attached, the indicated concentrations of Norleual were added to the top chamber. Additionally, 300 µl of 20 ng/ml HGF alone and with $10^{-9}$ M, $10^{-10}$ M, and $10^{-11}$ M Norleual was added to the bottom chamber to stimulate migration through the membrane. The cells were allowed to migrate for six hours before they were fixed and stained with Diff-Quik (Dade-Behring). The cells that had invaded the collagen and migrated to the underside of the membrane were counted in five random fields at 40× on a light microscope. The effect of treatment was determined using the one-way ANOVA with tukey's post-hoc analysis (PRISM® statistical analysis software). * indicates p<0.05 vs. HGF treatment. N=3 per treatment, mean+/−SEM.

Figure 10A:
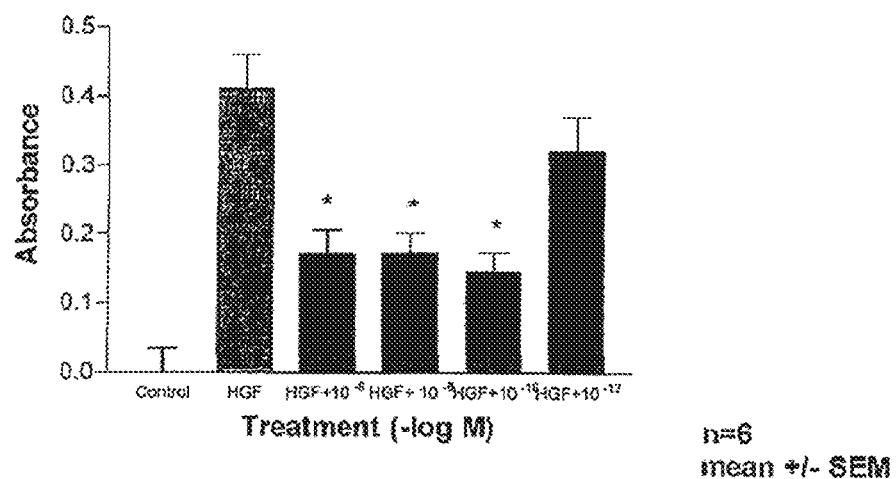
Figure 10B:
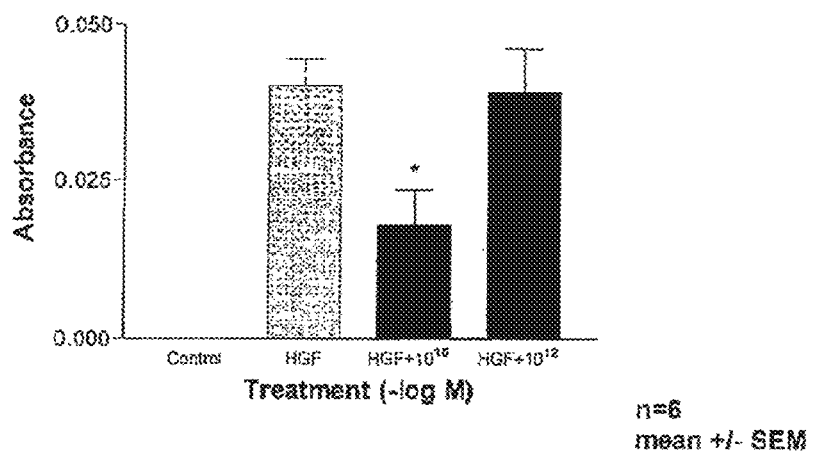

FIG. 10 show Norleual effect on c-Met/HGF stimulated Madin-Darby Canine Kidney (MDCK) cell proliferation and on MDCK uPA induction. FIG. 10A shows attenuation by Norleual of c-Met/HGF stimulated Madin-Darby Canine Kidney (MDCK) cell proliferation: 50,000 MDCK cells were plated in each well of a 96 well plate serum deprived for 24 hours to induce quiescence. Thereafter, 10 ng/ml of HGF alone and with the indicated concentrations of Norleual in a 1% FBS DMEM were added to the cells. The cells were cultured under these conditions for four days. On the fourth day, the treatment media was aspirated and replaced with 5 mg/ml of MTT reagent in 0.1 M glycine buffer (Invitrogen). The MTT reagent was incubated with the cells for four hours at 37° C. before adding DMSO to solubilize the cells and record the MTT absorbance on a plate reader. The controls were treated as background and subtracted from all of the treatments to determine the increase in proliferation due solely to HGF treatment. Differences between the treatments were determined using one-way ANOVA with Bonferroni's post-hoc analysis (PRISM® statistical analysis software). * indicate p<0.05 vs. HGF treatment. N=6, mean+/−SEM. FIG. 10B shows attenuation by the c-Met antagonist Norleual of c-Met/HGF urokinase plasminogen activator (uPA) induction. 50,000 Madin-Darby Canine Kidney (MDCK) cells were plated in the wells of a 96 well plate in 100 µl of complete Dulbecco's Modified Eagle's Medium (DMEM). The cells were serum starved for 24 hours to induce quiescence. Following serum deprivation, 10 ng/ml of Hepatocyte Growth Factor (HGF) alone and with a $10^{-10}$ M and $10^{-12}$ M Norleual prepared in a 1% FBS DMEM were added to the cells and the cells were incubated at 37° C. for 48 hours under these treatment conditions. After the 48 hour treatment, 10 μl of the chromophore labeled tripeptide uPA substrate (Boehringer-Mannheim, Indianapolis, Ind.) was added to the cells and incubated for four hours at 37° C. Absorbance of the cleaved substrate was quantitated on a Biotek SYNERGY™ 2 plate reader according to the manufacturer's instructions. Controls were considered background and were subtracted from all treatments. The data was analyzed with PRISM® (GraphPad, San Diego, Calif.) statistical analysis software. * indicates p<0.01 vs. HGF treatment by Tukey's post-hoc analysis. N=6 per treatment, mean+/−SEM.

Figure 11A:
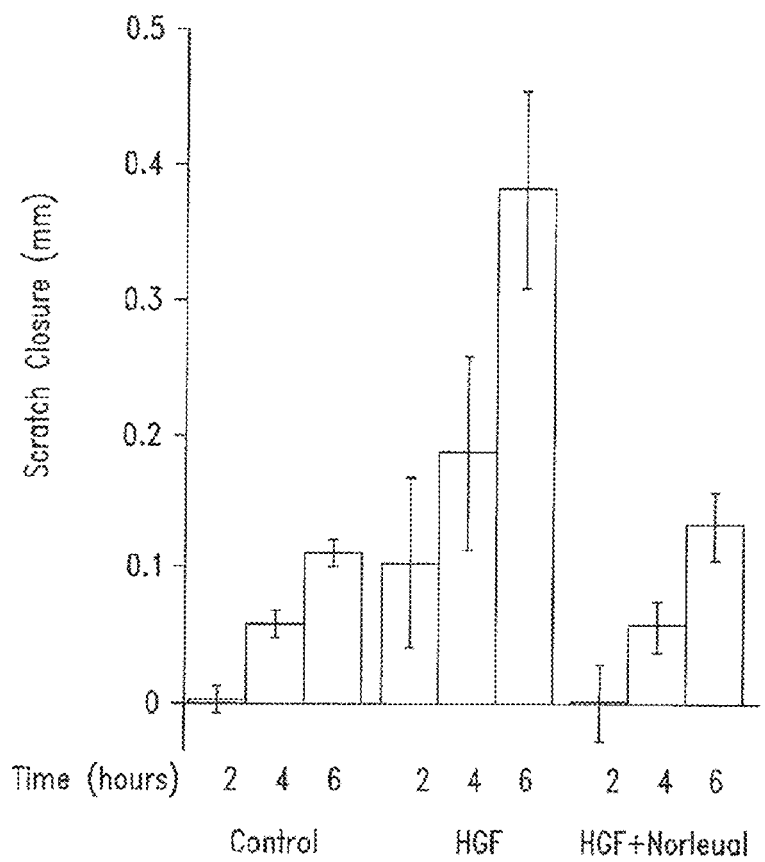
Figure 11B:
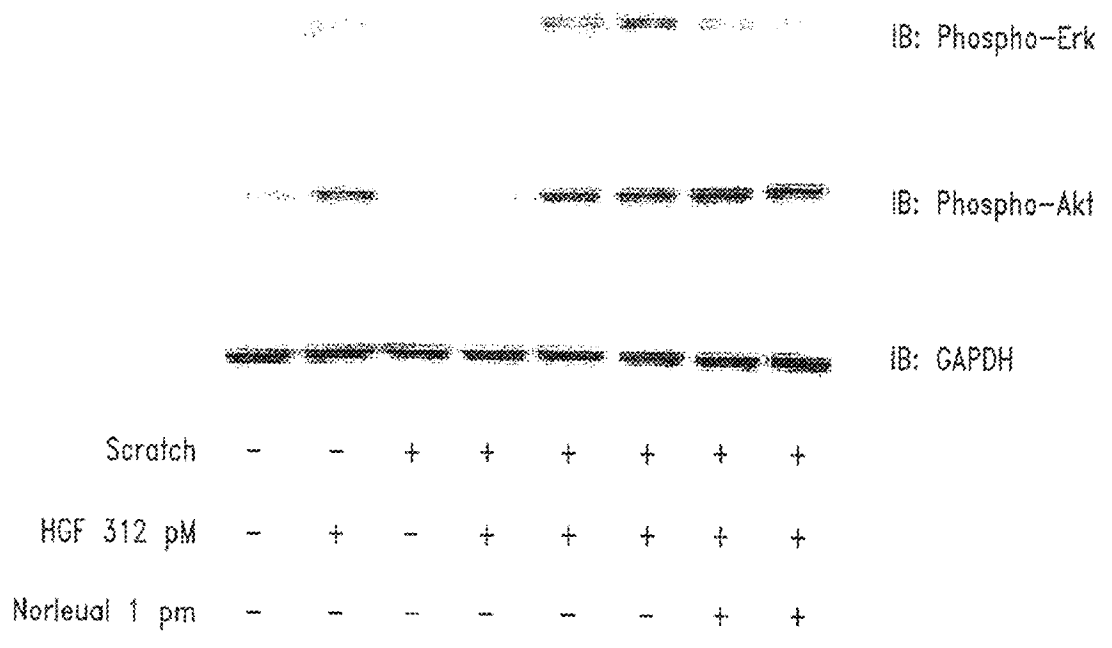

FIG. 11 shows Norleual effects in a B16-F10 murine melanoma cells scratch wound closure assay. FIG. 11A shows Norleual attenuation of HGF-potentiated scratch closure at 2, 4 and 6 hour timepoints. FIG. 11B shows relative Norleual effects on Erk1/2 and Akt phosphorylation in the HGF-potentiated B16-F10 murine melanoma cells scratch wound closure assay.

Figure 12:
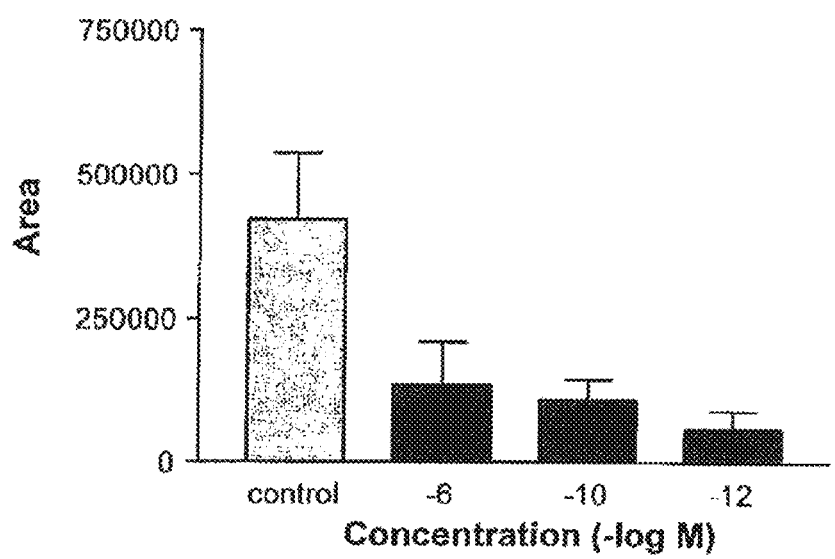

FIG. 12 shows effects of Norleual on murine SA-WAZ-2T breast carcinoma cell migration in vitro.

Figure 13A:
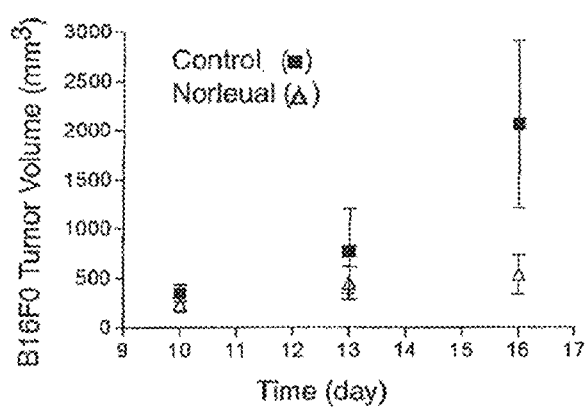
Figure 13B:
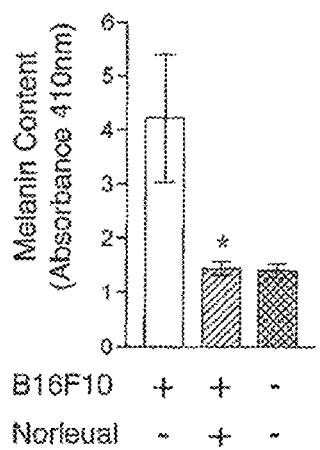
Figure 13C:
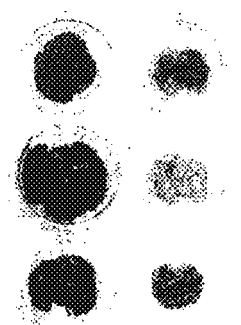

FIG. 13 shows Norleual inhibition of melanoma growth and metastasis in vivo. (FIG. 13A) C57BL/6 mice were inoculated subcutaneously with B16-F10 cells. Control or Norleual-containing slow release ELVAX® pellets were implanted inter-muscularly. Tumors were measured with digital calipers and tumor volumes were calculated (n=6), error bars indicate +/−SD. (FIG. 13B) 400,000 B16-F10 cells, treated in suspension with either Norleual at $10^{-11}$ M or PBS as a vehicle control, were injected into the tail vein of C57BL/6 mice. Mice received IP injections of Norleual (50 μg/kg/day) or PBS vehicle control. After fourteen days, lungs were removed and the absorbance of melanin was used to quantify metastasis; bars show (left to right) graft recipients treated with vehicle only, Norleual treated graft recipients, and ungrafted age-matched control. Error bars indicate +/−SEM, with n=5 and *p<0.05. (FIG. 13C) Photo of representative lungs from vehicle-only treated (controls, "Norleual−") and Notional treated ("Norleual+") grafted mice.

Figure 14:
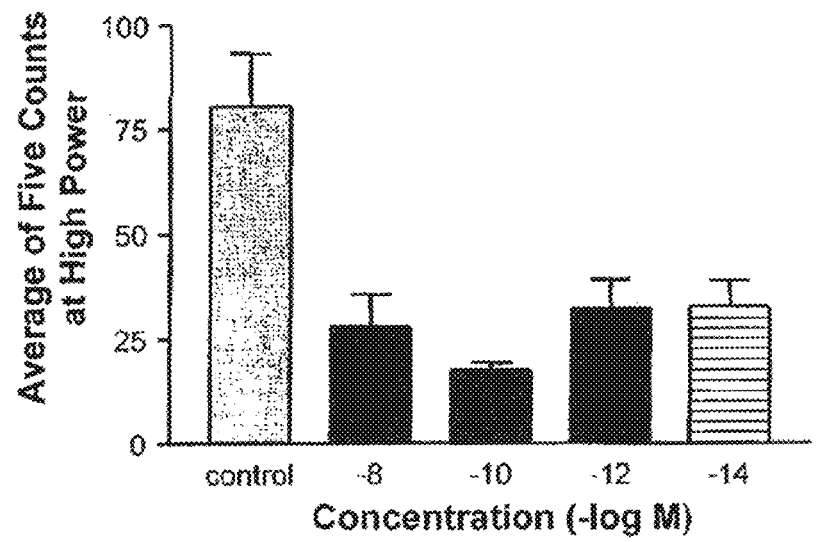

FIG. 14 shows Norleual effects on endothelial cell migration in vitro.

Figure 15:
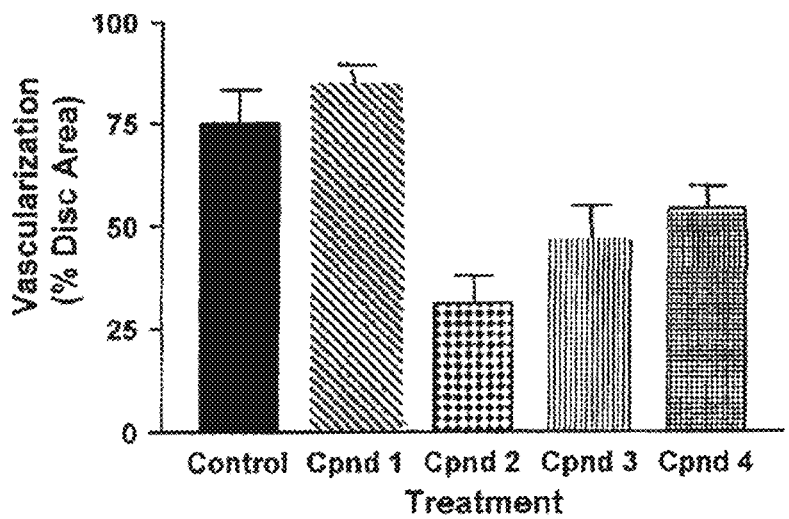

FIG. 15 shows the effect of several compounds comprising different single angiotensin-like factors on in vivo angiogenesis as determined by vascularization in a disc assay. Briefly, each compound comprising a single angiotensin-like factor was placed within a surgical sponge and the sponge was "sandwiched" in between two impermeable membranes, thereby forming the disc. Next, each disc containing the angiotensin-like factor was implanted subcutaneously in a rat animal model and neovascularization was measured after 10 days for each compound: Compound 1, (SEQ ID NO:41); Compound 2 (Norleual, SEQ ID NO:43); Compound 3, (SEQ ID NO:47); Compound 4, SEQ ID NO:52 [Nle-Tyr-Ile-6 (amino) hexanoic acid amide].

Figure 16A:
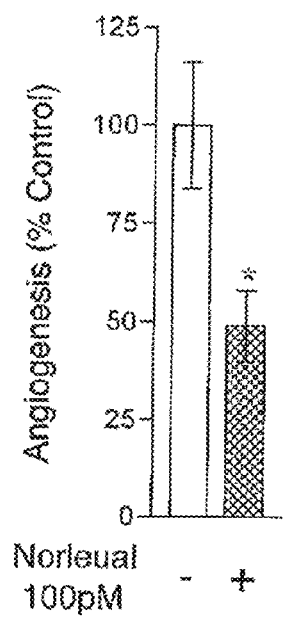
Figure 16B:
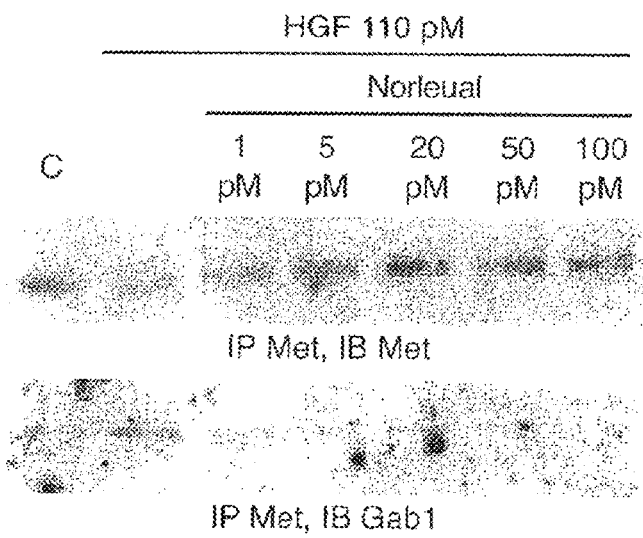

FIG. 16 depicts inhibition of angiogenesis by Norleual (Compound 2, SEQ ID NO:43) in the mouse aortic ring assay. Rings were incubated in EGM-2 media (Cambrex) with (n=8) or without (n=6) 100 pM Norleual for four days. Digital photos of the rings were taken on day four. FIG. 16A: Quantification of aortic ring angiogenesis. Areas covered by angiogenic sprouts were quantified from day four ring photos, control (−) and Norelual treated (+) (p-value=0.012* and error bars indicate +/−SEM). FIG. 16B: HUVECs were treated for 5 minutes with HGF and/or Norleual at indicated concentrations. Lysates were IP with anti-c-Met and IB with anti-c-Met or Gab1.

Figure 17:
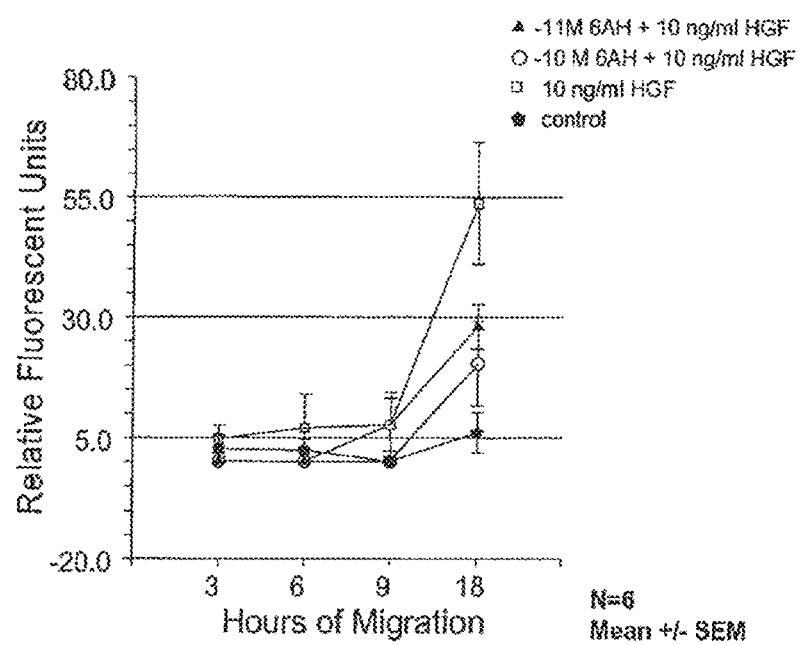

FIG. 17 shows effects on Madin-Darby Canine Kidney (MDCK) Cell Migration of isolated angiotensin-like factors. Compound 4, SEQ ID NO:52 [Nle-Tyr-Ile-6 (amino) hexanoic acid amide] was tested for its effect on MOCK cell migration toward an increasing gradient of Hepatocyte Growth Factor (HGF) in the FLUOROBLOCK™ transwell migration assay (BD) Biosciences). MDCK cells were grown to 100% confluency in 100 mm plates and serum deprived for 24 induce to induce quiescence. After 24 hours of serum deprivation, the cells were fluorescently labeled with 5 μg/ml of VYBRANT® Dil (Molecular Probes, Eugene, Oreg.) for 30 minutes at 37° C. The cells were washed three time with serum free medium to remove any residual dye from the media. The fluorescing cells were detached from the plate by adding 3 mls of 0.25% trypsin and incubating for five minutes at 37° C. The cells were resuspended in 10 mls of 1% serum media to neutralize the trypsin and the cells were centrifuged at 1000.times.g for 10 minutes to pellet the cells. The supernatant was aspirated from the cell pellet and the cells were resuspended in 8 mls of fresh 1% FBS DMEM. The cell suspension was triturated to obtain an even cell suspension. 50,000 cells were seeded in the top chamber of the FLUOROBLOCK® transwell chamber (BD Biosciences, San Jose, Calif.) and were allowed to attach for two hours at 37° C. The cells were pre-incubated with the peptide (Compound 4) for 15 minutes prior to adding 300 μl of 5-10 HGF with or without the peptide to the lower chamber to stimulate migration. Compound 4 was used at $10^{-10}$ and $10^{-11}$ molar. The data were analyzed with one-way ANOVA followed by Student Newman Keuls post-hoc analysis using NCSS statistical software. P<0.05 for Compound 4 vs. HGF as determined by Student Newman Keuls post-hoc analysis.

Figure 18:
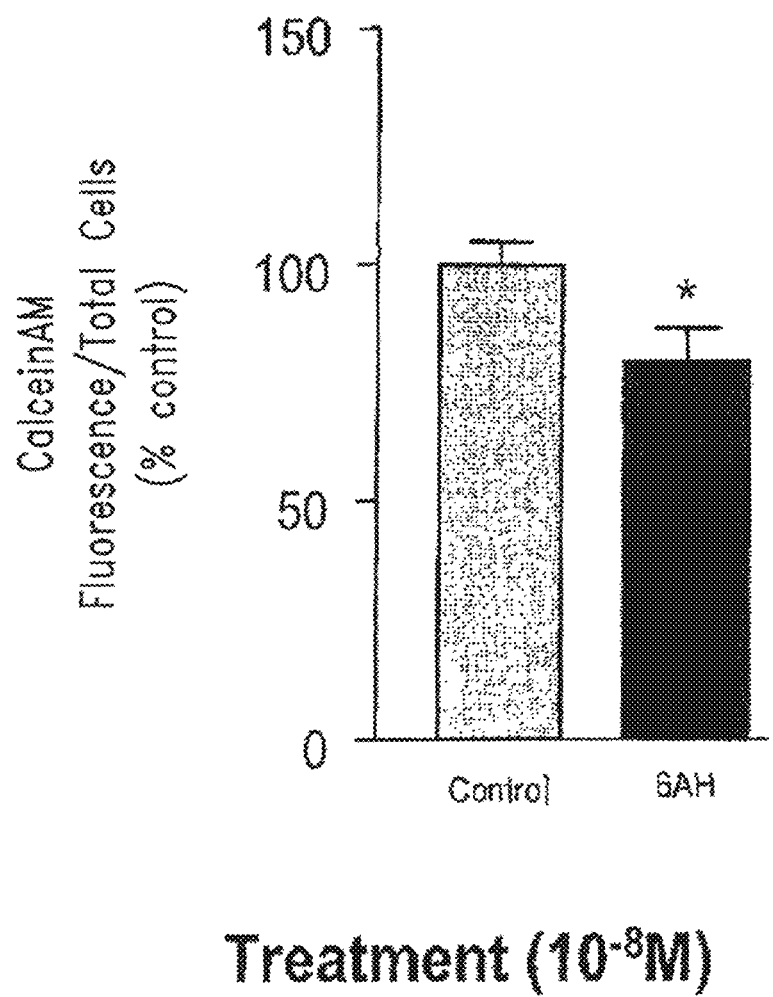

FIG. 18 shows effects of 6AH derivatives on U87 cell viability. 50,000 U87 cells were seeded into each well of a 96 well plate in 10% FBS Eagle's Modified Essential Medium (EMEM). After seeding the cells into the wells, the medium was replaced with a 1% FBS EMEM with or without the indicated peptides. All peptides were tested at $10^{-8}$M. The cells were grown for seven days under these treatment conditions. On the seventh day, cell viability was determined by adding 0.2 μM of Calcein AM (Molecular Probes) to the wells and quantitating the amount of Calcein fluorescence for each well on a fluorescent plate reader. The total number of cells was determined by killing the cells with 100% methanol for 30 minutes and staining the cells with ethidium-1 homodimer. Calcein fluorescence is divided by ethidium-1 homodimer fluorescence to determine the live to total cell ratio. 6AH is the parent molecule with Tyrosine in the #2 position. 6AH Asp #2=Aspartic Acid in the #2 position, 6AH Trp #2=Tryptophan in the #2 position, and 6AH Gly #2=Glycine in the #2 position, 6AH Ser #2=Serine in the #2 position, 6AH His=Histidine in the #2 position. The 6AH #1 derivatives include Butaric acid, Hexanoic acid, Propionic acid, and Valerie acid. The asterisks indicate p<0.05 versus control by Student Newman Keuls post-hoc analysis.

Figure 19:
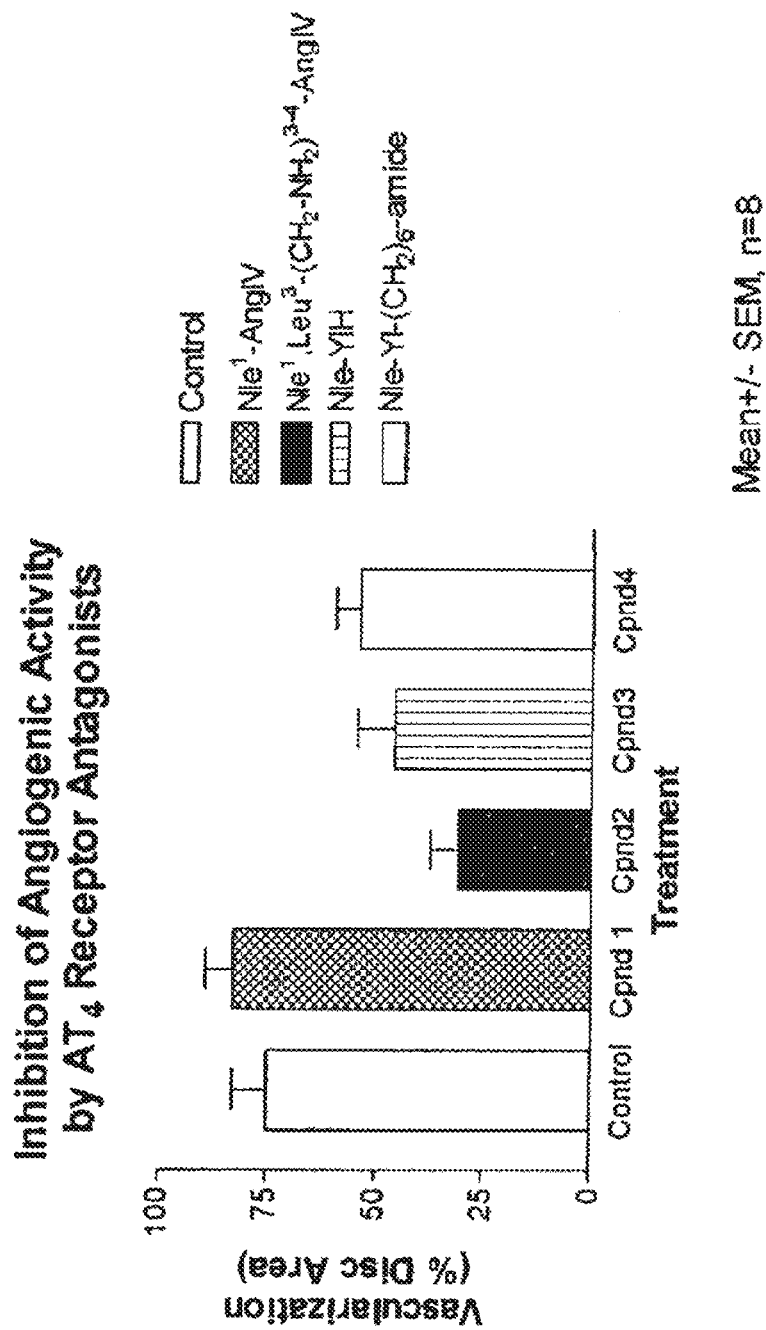

FIG. 19 depicts effects on angiogenesis of angiotensin-like factors in a rat in vivo disc angiogenesis assay. Vascularization was quantified by digital image analysis of fixed and stained discs recovered from animals 14 days after subcutaneous implantation of sponge discs containing the indicated compounds.

Figure 20:
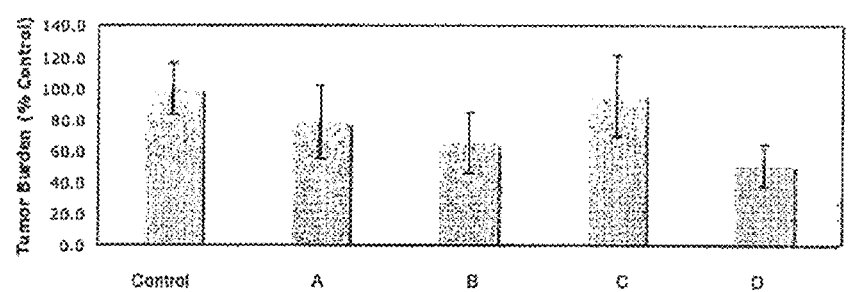

FIG. 20 shows anti-cancer activity of several angiotensin-like factors in the C57BL/6 murine model of in vivo metastasis using B16-F10 melanoma cells.

Figure 21:
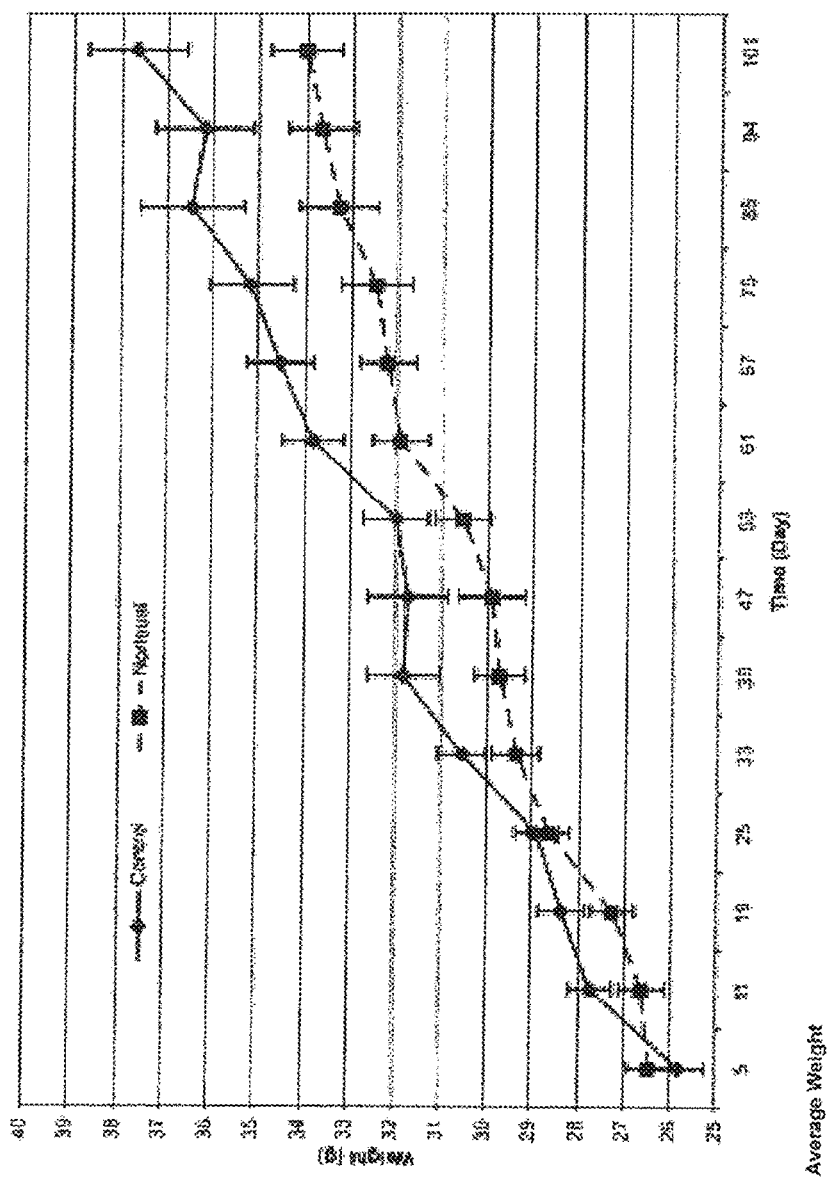

FIG. 21 shows the effect of in vivo treatment with an angiotensin-like factor on murine body weight.

Figure 22:
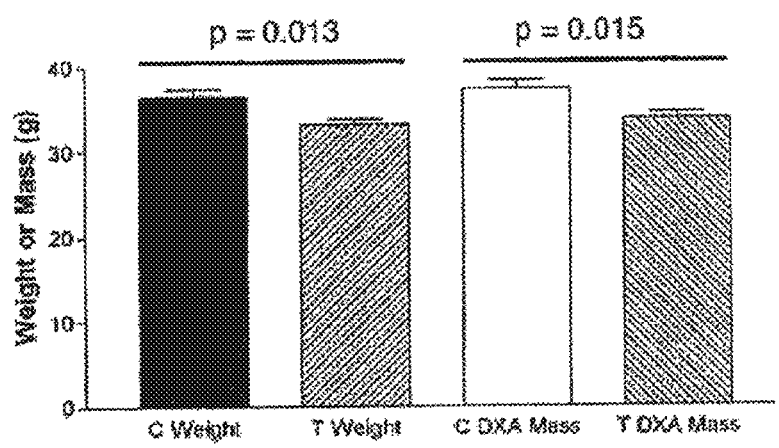
Figure 22:
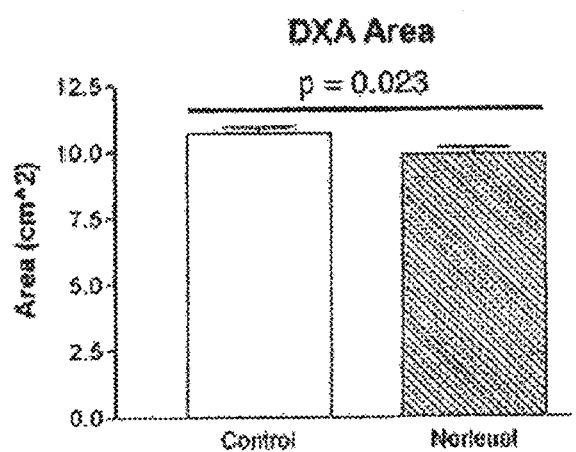
Figure 22:
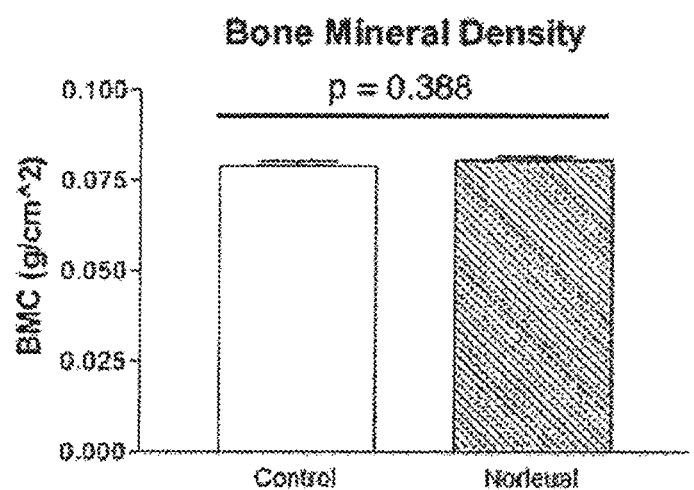
Figure 22:
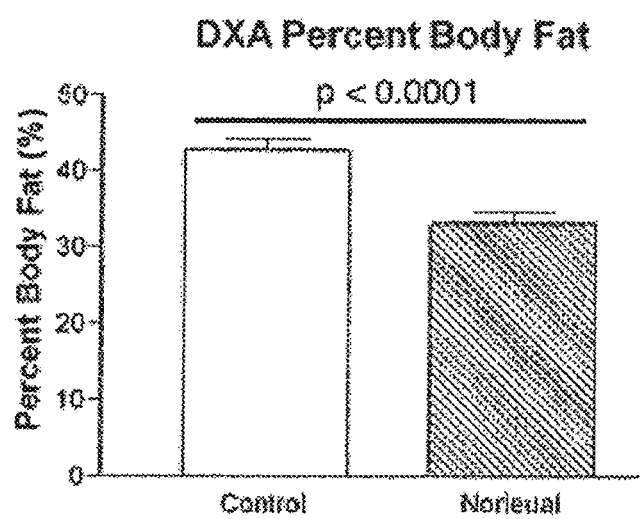
Figure 22:
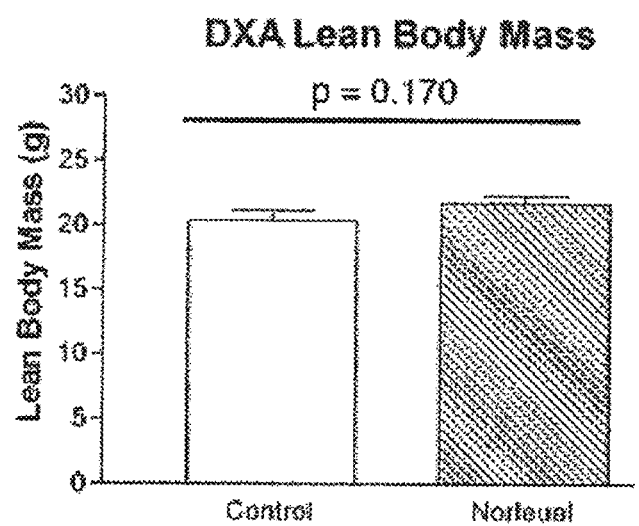

FIG. 22 shows digital X-ray analysis of murine body weight, bone mineral density, percent body fat and lean body mass following in vivo treatment with an angiotensin-like factor.

FIG. 23 shows the effect of angiotensin-like factors on viability of HGF-induced human umbilical vein endothelial cells.

DETAILED DESCRIPTION

Certain embodiments of the invention disclosed herein are based on the surprising discovery that angiotensin-like factors may act as agonists or antagonists of the c-Met receptor. In particular, and as disclosed herein, it has been discovered that natural and/or synthetic angiotensin peptides (including angiotensinogen precursor peptides) and other structurally related angiotensin-like factors as described herein, including in certain embodiments natural and/or synthetic polypeptides containing a consensus amino acid sequence of the general formula N-aromatic amino acid-hydrophobic amino acid—basic amino acid—C, or having another structure as disclosed herein, are capable of altering (i.e. increasing or decreasing in a statistically significant manner, e.g. relative to an appropriate control) a hepatocyte growth factor (HGF) activity or a c-Met receptor activity, for example and according to certain non-limiting embodiments, by altering HGF binding to the c-Met receptor.

The presently disclosed compositions and methods will find use in any context where it may be desired to alter a hepatocyte growth factor activity or a c-Met receptor activity, such as in situations where intervention is sought to alter cell proliferation, migration, adhesion, differentiation or other cellular functions, in processes that may include, for example, one or more of cardiovascular regulation, angiogenesis, inflammation, neuronal growth or regeneration, cognitive dysfunction, adipose tissue deposition, bone regeneration or other tissue repair, or other physiological processes. Embodiments described herein may thus find therapeutic uses, but the present disclosure is not intended to be so limited and also contemplates diagnostics, screening assays for identification of therapeutic compounds and/or for identification of signal transduction pathway components, including such components that may provide additional or alternative useful therapeutic targets, and other useful applications of the discoveries as presently disclosed.

Hepatocyte growth factor (HGF) activities or c-Met receptor activities may in certain preferred embodiments relate to any biological process or event that results from, contributes to or otherwise involves a specific binding interaction between (i) HGF (e.g., GenBank Accession No. AAA64239, SEQ ID NO:83) or an angiotensin-like factor that is capable of specifically binding to the cell surface c-Met receptor as provided herein, and (ii) the c-Met receptor (e.g., GenBank Accession No. AAA59591, SEQ ID NO:84), that effects a detectable (e.g., with statistical significance) change (e.g., phosphorylation state or other structural and/or functional indicia of an activity state change) in the c-Met receptor and/or in a component of the c-Met receptor signal transduction pathway.

Hepatocyte growth factor activities or c-Met receptor activities may include induction of cell proliferation, induction of cell scattering, induction of cell migration, induction of specific gene expression patterns (which may include both up- and down-regulation of the expression of one or more particular genes or a coordinated sequence of differential gene expression) or up-regulation or down-regulation of downstream intracellular signaling molecules (e.g., changes in phosphorylation states of molecules, such as Gab1). As described herein, induction is intended to refer to either or both of initiating the event, as well as up-regulating the event (i.e. increasing the event by a statistically significant amount).

One of skill in the art is readily able to measure such activities by, for example, in vitro or in vivo assays including radiometric determination of cells or cellular components derived therefrom following radiolabeling with isotopic molecular precursors (e.g., analysis of radiolabeled phosphoproteins and/or protein tyrosine phosphate following $^{32}$P labeling; quantification of cellular proliferation by determining incorporated $^3$H-thymidine; determination of protein biosynthesis by incorporation of a radiolabeled amino acid into cellular protein; determination of extracellular matrix (ECM) degradation or biosynthesis by detection of a radiolabeled ECM precursor that is liberated or incorporated by cells into surrounding ECM, assays of transcription or transcription factor activity such as transcriptional run-off assays or the like, etc.) and subsequently monitoring radioactivity or activity of another detectable indicator; fluorescence microscopy or flow cytometry (e.g., immunocytofluorimetry) of cell populations; qualitative and/or quantitative immunofluorescence of cells; and using micro-carrier beads to assay cell migration or scattering. (See, for example, Arbab et al., Blood 15: 104 (10) 3410-2 (2004); Rosen et al., Exp. Cell Res., 186(1) 22-31 (1990).)

Other hepatocyte growth factor activities or c-Met receptor activities may include cellular extravasation, disruption of extracellular matrix, tumor metastasis, increased angiogenesis, increased adipogenesis, increased tumor size or burden, or other related activities (detectable by, for example, changes in cell adhesion molecule expression and/or by in vivo or in vitro methodologies with which those skilled in the art will be familiar, such as by histochemistry, immunohistology, emission spectrum scanning multiphoton microscopy of quantum dot-labeled cells, in vivo optical imaging, in vivo NMR, functional magnetic resonance imaging, etc.).

Certain hepatocyte growth factor activities or c-Met activities may relate to metabolic conditions characterized by aberrant adiposity, such as obesity and conditions associated with obesity. Conditions associated with obesity or aberrant adiposity may include, by way of example, pre-diabetic or diabetic conditions, non-alcoholic fatty liver disease, dyslipidemia, hypercholesterolemia, cardiovascular diseases or conditions, increased inflammatory activity, thrombosis, immobility, gout, osteoarthritis, respiratory conditions, psychological conditions, and various types of cancer.

Other examples of well known methodologies available for quantifying cellular proliferation include incorporation of tritiated thymidine into cellular DNA, monitoring of detectable (e.g., fluorimetric or colorimetric) indicators of cellular respiratory activity, (e.g., MTT assay) or cell counting, or the like. Similarly, in the cell biology arts there are known multiple techniques for assessing cell survival (e.g., vital dyes, metabolic indicators, etc.) and for determining apoptosis (e.g., annexin V binding, DNA fragmentation assays, caspase activation, PARP cleavage, etc.). Other signaling pathways will be associated with particular cellular phenotypes, for example specific induction of gene expression (e.g., detectable as transcription or translation products, or by bioassays of such products, or as nuclear localization of cytoplasmic factors), altered (e.g., statistically significant increases or decreases) levels of intracellular mediators (e.g., activated kinases or phosphatases, altered levels of cyclic nucleotides or of physiologically active ionic species, etc.), altered cell cycle profiles, or altered cellular morphology, and the like, such that cellular responsiveness to a particular stimulus as provided herein can be readily identified to determine whether a particular cell comprises an inducible signaling pathway.

Certain embodiments described herein relate to a biological signaling pathway or signal transduction pathway that comprises a c-Met receptor pathway, which may be induced in subject or biological source cells by contacting such cells with an appropriate stimulus, which may vary depending upon the signaling pathway under investigation, whether known or unknown. For example, a signaling pathway that, when induced, results in c-Met receptor protein tyrosine phosphorylation and/or c-Met or other phosphoprotein tyrosine dephosphorylation may be stimulated in subject or biological source cells using any one or more of a variety of well known methods and compositions known in the art to stimulate protein tyrosine kinase and/or protein tyrosine phosphatase (PTP) activity. These stimuli may include, without limitation, exposure of cells to cytokines, growth factors, hormones, peptides, small molecule mediators, cell stressors (e.g., ultraviolet light; temperature shifts; osmotic shock; ROS or a source thereof, such as hydrogen peroxide, superoxide, ozone, etc. or any agent that induces or promotes ROS production (see, e.g., Halliwell and Gutteridge, Free Radicals in Biology and Medicine (3rd Ed.) 1999 Oxford University Press, Oxford, UK); heavy metals; alcohol) or other agents that induce c-Met receptor protein tyrosine phosphorylation and/or PTP-mediated phosphoprotein tyrosine dephosphorylation.

As known in the art, for example, HGF under appropriate conditions can induce a c-Met receptor pathway, such as by altering the phosphorylation state of the c-Met receptor and/or of a downstream molecular component (e.g., Grb1) of the c-Met receptor pathway. As described herein for the first time, isolated AT4 and/or other isolated angiotensin-like factors, according to certain embodiments as provided herein, are capable of specifically binding to the cell surface c-Met receptor and by so doing may induce one or more alterations in the phosphorylation state of one or more c-Met receptor signal transduction pathway components.

Other agents that may be capable of inducing a signal transduction pathway may include, for example, interleukins (e.g., IL-1, IL-3), interferons (e.g., IFN-γ.), human growth hormone, insulin, epidermal growth factor (EGF), platelet derived growth factor (PDGF), granulocyte colony stimulating factor (G-CSF), granulocyte-megakaryocyte colony stimulating factor (GM-CSF), transforming growth factor (e.g., TGF-β1), tumor necrosis factor (e.g., TNFα) and fibroblast growth factor (FGF; e.g., basic FGF (bFGF)), any agent or combination of agents capable of triggering T lymphocyte activation via the T cell receptor for antigen (TCR; TCR-inducing agents may include superantigens, specifically recognized antigens and/or MHC-derived peptides, MHC peptide tetramers (e.g., Altman et al., 1996 Science 274:94-96) TCR-specific antibodies or fragments or derivatives thereof), lectins (e.g., PHA, PWM, ConA, etc.), mitogens, G-protein coupled receptor agonists such as angiostatin, thrombin, thyrotropin, parathyroid hormone, lysophosphatidic acid (LPA), sphingosine-1-phosphate, serotonin, endothelin, acetylcholine, platelet activating factor (PAF) or bradykinin, as well as other agents with which those having ordinary skill in the art will be familiar (see, e.g., Rhee et al., 10 Oct. 2000 Science and references cited therein; see also Gross et al., 1999 J. Biol. Chem. 274:26378-86; Prenzel et al., 1999 Nature 402:884-88; Ushio-Fukai et al., 1999 J. Biol. Chem. 274:22699-704; Holland et al., 1998 Endothelium 6:113-21; Daub et al., 1997 EMBO J. 16:7032-44; Krypianou et al., 1997 Prostate 32:266-71; Marumo et al., 1997 Circulation 96:2361-67).

As noted above, regulated tyrosine phosphorylation contributes to specific pathways for biological signal transduction, including those associated with cell division, cell survival, apoptosis, proliferation and differentiation, and "inducible signaling pathways" in the context of the presently disclosed embodiments include transient or stable associations or interactions among molecular components involved in the control of these and similar processes in cells. Depending on the particular pathway of interest, an appropriate parameter for determining induction of such pathway may be selected. For example, for signaling pathways associated with cell proliferation, there is available a variety of well known methodologies for quantifying proliferation, including, for example, incorporation of tritiated thymidine into cellular DNA, monitoring of detectable (e.g., fluorimetric or colorimetric) indicators of cellular respiratory activity, or cell counting, or the like. Similarly, in the cell biology arts there are known multiple techniques for assessing cell survival (e.g., vital dyes, metabolic indicators, etc.) and for determining apoptosis (e.g., annexin V binding, DNA fragmentation assays, caspase activation, etc.). Other signaling pathways will be associated with particular cellular phenotypes, for example specific induction of gene expression (e.g., detectable as transcription or translation products, or by bioassays of such products, or as nuclear localization of cytoplasmic factors), altered (e.g., statistically significant increases or decreases) levels of intracellular mediators (e.g., activated kinases or phosphatases, altered levels of cyclic nucleotides or of physiologically active ionic species, etc.), or altered cellular morphology, and the like, such that cellular responsiveness to a particular stimulus as provided herein can be readily identified to determine whether a particular cell comprises an inducible signaling pathway.

A number of methods are described herein and known in the art for detection of one or more particular signal transduction pathway component polypeptides such as c-Met receptor pathway components, and for determination of whether such polypeptides may be tyrosine-phosphorylated in cells following stimulation as described herein. Also described herein are methods for detecting such polypeptides, including determination of altered (i.e., increased or decreased with statistical significance) tyrosine phosphorylation that may further include determination of the phosphorylation state of particular tyrosine residues at specified positions within a polypeptide sequence, which altered tyrosine phosphorylation may in certain embodiments be accompanied by the presence or absence of induction of one or more HGF activities or c-Met receptor activities in the cells from which such polypeptides are obtained (e.g., as a result of exposure to a stimulus, such as HGF and/or an angiotensin-like factor as provided herein).

Non-limiting examples of such detection methods include the use of reagents that specifically bind to c-Met receptor signaling pathway components, for example, by immunological methods (e.g., immunoprecipitation, immunoblotting, ELISA, radioimmunoprecipitation, and the like) that employ antibodies as provided herein that are capable of specifically binding a particular signaling pathway component polypeptide or a particular tyrosine-phosphorylated polypeptide.

Additionally and as described in greater detail herein, in certain embodiments induction of one or more HGF activities or c-Met receptor activities induced by a stimulus may be partially or completely impaired, abrogated, inhibited or otherwise counteracted by inclusion of an angiotensin-like factor that is capable of specifically binding to a cell surface c-Met receptor, for instance, by virtue of being able to inhibit competitively the binding to the cell surface c-Met receptor of a native HGF hinge region polypeptide having the amino acid sequence Lys-Asp-Tyr-Ile-Arg-Asn-Cys [SEQ ID NO:82].

In certain distinct but related embodiments, induction of one or more HGF activities or c-Met receptor activities induced by a stimulus may be partially or completely impaired, abrogated, inhibited or otherwise counteracted by inclusion of an angiotensin-like factor that is capable of interfering with assembly of full-length naturally occurring HGF monomeric subunit polypeptides into the functional, biologically active native HGF homodimer, thereby preventing effective signal transduction through c-Met receptor binding. Biochemical or biophysical criteria for differentiating between the presence of HGF monomers and homodimers are well within the methodologies with which those skilled in the art will be familiar, for example, through the use of comparative molecular separation techniques under native and denaturing conditions, such as gel electrophoresis or gel filtration chromatography, or other suitable techniques. According to non-limiting theory, for example, based on the disclosure herein that c-Met receptor activity may result from specific binding interaction between the native HGF hinge region polypeptide having the amino acid sequence Lys-Asp-Tyr-Ile-Arg-Asn-Cys [SEQ ID NO:82] and the c-Met receptor, certain herein described angiotensin-like factors, which comprise a polypeptide having SEQ ID NO:82 or a peptide fragment thereof or a peptidomimetic thereof, are believed specifically to interact with structurally homologous regions of a full-length naturally occurring HGF polypeptide monomer in a manner that disrupts full length native HGF homodimer formation, thereby partially or completely inhibiting HGF activity or c-Met receptor activity.

The surprising discovery disclosed herein, that the c-Met receptor acts as a functional biological receptor for AT(4) and other AT(4) receptor ligands, including angiotensin-like factors as provided herein, permits advantageously contacting a cell or plurality of cells with such an isolated angiotensin-like factor that is capable of specifically binding to a cell surface c-Met receptor and/or that disrupts native HGF homodimer formation by binding to the hinge region comprising SEQ ID NO:82 in the HGF polypeptide, under conditions and for a time sufficient for the angiotensin-like factor to interact with the cell surface c-Met receptor and/or with a HGF polypeptide, to provide a method for altering a hepatocyte growth factor activity or a c-Met receptor activity.

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acid could be part of a vector and/or such nucleic acid or polypeptide could be part of a composition (e.g., a cell lysate), and still be isolated in that such vector or composition is not part of the natural environment for the nucleic acid or polypeptide. The term "gene" means the segment of DNA involved in producing a polypeptide chain; it includes regions preceding and following the coding region "leader and trailer" as well as intervening sequences (introns) between individual coding segments (exons).

In particular, according to certain preferred embodiments angiotensin-like factors may comprise peptides, polypeptides or peptidomimetics that include, or that share close sequence identity to or structural features with, amino acids 122-128 of the hepatocyte growth factor precursor polypeptide having the amino acid sequence set forth in SEQ ID NO:2 (in which the amino acids at sequence positions 122-128 are Lys-Asp-Tyr-Ile-Arg-Asn-Cys [SEQ ID NO:82], also referred to as the HGF "hinge region") or the closely related sequence set forth in SEQ ID NO:1 (Leu-Asp-Tyr-Ile-Arg-Asn-Cys). Polypeptides of 2, 3, 4, 5, 6, 7, 8, 9, 10, 11, 12, 13, 14, 15, 16, 17, 18 or 19 amino acids having such a HGF hinge region polypeptide structure, including polypeptides having at least 75%, 80%, 85%, 90% or 95% sequence identity or sequence homology thereto, or peptidomimetics thereof, which in certain preferred embodiments may be polypeptides of no more than 15, 14, 13, 12, 11, 10, 9, 8, 7, 6, 5, 4, 3 or 2 amino acids or peptidomimetics thereof, and in certain particularly preferred embodiments may be polypeptides of 2, 3, 4, 5, 6 or 7 amino acids or peptidomimetics thereof, have been found to be especially effective in out-competing the native hepatocyte growth factor for binding to the c-Met receptor and/or in otherwise inhibiting (e.g., by disrupting assembly of the functional HGF non-covalent homodimer) effective biological signal transduction by HGF via the c-Met receptor.

Thus, for example and according to certain non-limiting embodiments, there is presently provided an isolated angiotensin-like factor comprising a polypeptide, or a peptidomimetic thereof, that inhibits (and in certain embodiments that competitively inhibits) binding of a native HGF hinge region polypeptide to a cell surface c-Met receptor, the native HGF hinge region polypeptide comprising the amino acid sequence Lys-Asp-Tyr-Ile-Arg-Asn-Cys [SEQ ID NO:82], wherein the angiotensin-like factor is selected from (a) a polypeptide of 15, 14, 13, 12, 11, 10, 9, 8, 7, 6, 5, 4, 3 or 2 amino acids, or a peptidomimetic thereof, said polypeptide comprising a peptide having at least one amino acid sequence that is selected from: Lys-Asp, Asp-Tyr, Tyr-Ile, Ile-Arg, Arg-Asn, Asn-Cys, Lys-Asp-Tyr, Asp-Tyr-Ile, Tyr-Ile-Arg, Ile-Arg-Asn, Arg-Asn-Cys, Lys-Asp-Tyr-Ile [SEQ ID NO: 86], Asp-Tyr-Ile-Arg [SEQ ID NO: 87], Tyr-Ile-Arg-Asn [SEQ ID NO: 88], Ile-Arg-Asn-Cys [SEQ ID NO: 89], Lys-Asp-Tyr-Ile-Arg [SEQ ID NO: 90], Asp-Tyr-Ile-Arg-Asn [SEQ ID NO: 91], Tyr-Ile-Arg-Asn-Cys [SEQ ID NO: 92], Lys-Asp-Tyr-Ile-Arg-Asn [SEQ ID NO: 93], Asp-Tyr-Ile-Arg-Asn-Cys [SEQ ID NO: 94], Lys-Asp-Tyr-Ile-Arg-Asn-Cys [SEQ ID NO:82], Gly-Asp-Tyr-Ile-Arg-Asn-Cys [SEQ ID NO: 95], Lys-Gly-Tyr-Ile-Arg-Asn-Cys [SEQ ID NO: 96], Lys-Asp-Gly-Ile-Arg-Asn-Cys [SEQ ID NO: 97], Lys-Asp-Tyr-Gly-Arg-Asn-Cys [SEQ ID NO: 98], Lys-Asp-Tyr-Ile-Gly-Asn-Cys [SEQ ID NO: 99], Lys-Asp-Tyr-Ile-Arg-Gly-Cys [SEQ ID NO: 100] Lys-Asp-Tyr-Ile-Arg-Asn-Gly [SEQ ID NO: 101], (D)-Lys-Asp-Tyr-Ile-Arg-Asn-Cys [SEQ ID NO: 102], Lys-(D)-Asp-Tyr-Ile-Arg-Asn-Cys [SEQ ID NO: 103], Lys-Asp-(D)-Tyr-Ile-Arg-Asn-Cys [SEQ ID NO: 104], Lys-Asp-Tyr-(D)-Ile-Arg-Asn-Cys [SEQ ID NO: 105], Lys-Asp-Tyr-Ile-(D)-Arg-Asn-Cys [SEQ ID NO: 106], Lys-Asp-Tyr-Ile-Arg-(D)-Asn-Cys [SEQ ID NO: 107], and Lys-Asp-Tyr-Ile-Arg-Asn-(D)-Cys [SEQ ID NO: 108], (b) the polypeptide or peptidomimetic thereof of (a) wherein the peptidomimetic of said polypeptide comprises 1, 2, 3, 4, 5 or 6 reduced peptide bonds, each of said peptide bonds having the formula $CH_2-NH_2^+$, (c) the polypeptide or peptidomimetic thereof of (b) wherein the peptidomimetic is selected from: Lys-Ψ-Asp-Tyr-Ile-Arg-Asn-Cys [SEQ ID NO: 109], Lys-Asp-Ψ-Tyr-Ile-Arg-Asn-Cys [SEQ ID NO: 110], Lys-Asp-Tyr-Ψ-Ile-Arg-Asn-Cys [SEQ ID NO: 111], Lys-Asp-Tyr-Ile-Ψ-Arg-Asn-Cys [SEQ ID NO: 112], Lys-Asp-Tyr-Ile-Arg-Ψ-Asn-Cys [SEQ ID NO: 113], Lys-Asp-Tyr-Ile-Arg-Asn-Ψ-Cys [SEQ ID NO: 114], Lys-Ψ-Asp-Ψ-Tyr-Ile-Arg-Asn-Cys [SEQ ID NO: 115], Lys-Ψ-Asp-Tyr-Ψ-Ile-Arg-Asn-Cys [SEQ ID NO: 116], Lys-Ψ-Asp-Tyr-Ile-Ψ-Arg-Asn-Cys [SEQ ID NO: 117], Lys-Ψ-Asp-Tyr-Ile-Arg-Ψ-Asn-Cys

[SEQ ID NO: 118], Lys-Ψ-Asp-Tyr-Ile-Arg-Asn-Ψ-Cys [SEQ ID NO: 119], Lys-Asp-Ψ-Tyr-Ψ-Ile-Arg-Asn-Cys [SEQ ID NO: 120], Lys-Asp-Ψ-Tyr-Ile-Ψ-Arg-Asn-Cys [SEQ ID NO: 121], Lys-Asp-Ψ-Tyr-Ile-Arg-Ψ-Asn-Cys [SEQ ID NO: 122], Lys-Asp-Ψ-Tyr-Ile-Arg-Asn-Ψ-Cys [SEQ ID NO: 123], Lys-Asp-Tyr-Ψ-Ile-Ψ-Arg-Asn-Cys [SEQ ID NO: 124], Lys-Asp-Tyr-Ψ-Ile-Arg-Ψ-Asn-Cys [SEQ ID NO: 125], Lys-Asp-Tyr-Ψ-Ile-Arg-Asn-Ψ-Cys [SEQ ID NO: 126], Lys-Asp-Tyr-Ile-Ψ-Arg-Ψ-Asn-Cys [SEQ ID NO: 127], Lys-Asp-Tyr-Ile-Ψ-Arg-Asn-Ψ-Cys [SEQ ID NO: 128], and Lys-Asp-Tyr-Ile-Arg-Ψ-Asn-Ψ-Cys [SEQ ID NO: 129], wherein Ψ is a peptide bond having the formula $CH_2$—$NH_2^+$, and (d) a polypeptide of 15, 14, 13, 12, 11, 10, 9, 8, 7, 6, 5, 4, 3 or 2 amino acids, or a peptidomimetic thereof, of general formula III:

[SEQ ID NO: 130]

$$N\text{--}X_1\text{-}X_2\text{-}X_3\text{-}X_4\text{-}X_5\text{-}X_6\text{-}X_7\text{--}C \quad [III]$$

wherein:

N is an amino terminus of the peptide or peptidomimetic and consists of 0, 1, 2, 3, 4, 5, 6, 7, 8, 9, 10, 11, 12, or 13 amino acids that are independently selected from natural and non-natural amino acids, C is a carboxy terminus of the peptide or peptidomimetic and consists of 0, 1, 2, 3, 4, 5, 6, 7, 8, 9, 10, 11, 12, or 13 amino acids that are independently selected from natural and non-natural amino acids, $X_1$ is nothing, Lys, Arg, His, Norleucine or hexanoic acid, $X_2$ is nothing, Asp or Glu, $X_3$ is nothing, Tyr, Phe or homo-Phe, $X_4$ is nothing, Ile, Leu, Val, Phe, Met or Norleucine, $X_5$ is nothing, Arg, Lys or His, $X_6$ is nothing, Asn or Gln, and $X_7$ is nothing, Cys or Cys-amide.

According to certain other particular embodiments, it is contemplated that any one or more specific angiotensin-like factors as set forth in (a)-(d) immediately above may be expressly excluded independently of any and all other angiotensin-like factors disclosed herein.

As generally referred to in the art, and as used herein, sequence identity and sequence homology may be used interchangeably and generally refer to the percentage of nucleotides or amino acid residues in a candidate sequence that are identical with, respectively, the nucleotides or amino acid residues in a native polynucleotide or polypeptide sequence, after aligning the sequences and introducing gaps, if necessary, to achieve the maximum percent sequence identity, and not considering any conservative substitutions as part of the sequence identity. Preferably, an angiotensin-like factor polypeptide or encoding polynucleotide of the embodiments disclosed herein shares at least about 75%, at least about 80%, at least about 85%, at least about 90%, at least about 95%, 96%, 97%, 98%, or 99% of the amino acid residues (or of the nucleotides in a polynucleotide encoding such an antiotensin-like factor polypeptide) with the HGF hinge region target sequence. Such sequence identity may be determined according to well known sequence analysis algorithms, including those available from the University of Wisonsin Genetics Computer Group (Madison, Wis.), such as FASTA, Gap, Bestfit, BLAST, or others.

It has also been determined according to certain embodiments of the present invention that N-terminus extensions of the angiotensin-like factors can alter the affinity of the angiotensin-like factor binding to the c-Met receptor, while C-terminus extensions can enhance binding and/or activity of the angiotensin-like factor. Another advantage of the compositions of certain herein disclosed embodiments is that most are effective at very low doses (for example, in the nanomolar to picomolar range). Furthermore, among the herein described angiotensin-like factors may be found c-Met receptor antagonists that are generally capable of functioning as anti-angiogenic as well as anti-tumor agents.

According to certain presently disclosed embodiments, an angiotensin-like factor comprises a polypeptide of no more than 20, 19, 18, 17, 16, 15, 14, 13, 12, 11, 10, 9, 8, 7, 6, 5, 4 or 3 amino acids, or a peptidomimetic thereof, of general formula I:

$$N\text{-}X_1\text{-}X_2\text{-}X_3\text{-}C \quad [I]$$

wherein N is an amino terminus of the peptide or peptidomimetic and consists of 0, 1, 2, 3, 4, 5, 6, 7, 8, 9, 10, 11, 12, 13, 14, 15, 16 or 17 amino acids that are independently selected from natural and non-natural amino acids, C is a carboxy terminus of the peptide or peptidomimetic and consists of 0, 1, 2, 3, 4, 5, 6, 7, 8, 9, 10, 11, 12, 13, 14, 15, 16 or 17 amino acids that are independently selected from natural and non-natural amino acids, $X_1$ is phenylalanine, tryptophan or tyrosine, $X_2$ is isoleucine, leucine, alanine, valine, phenylalanine, proline, methionine or tryptophan, and $X_3$ is lysine, arginine or histidine.

"Natural or non-natural amino acid" includes any of the common naturally occurring amino acids which serve as building blocks for the biosynthesis of peptides, polypeptides and proteins (e.g., alanine, cysteine, aspartic acid, glutamic acid, phenylalanine, glycine, histidine, isoleucine, lysine, leucine, methionine, asparagine, proline, glutamine, arginine, serine, threonine, valine, tryptophan, tyrosine) and also includes modified, derivatized, enantiomeric, rare and/or unusual amino acids, whether naturally occurring or synthetic, for instance, hydroxyproline, hydroxylysine, desmosine, ϵ-isodesmosine, ϵ-N-methyllysine, ϵ-N-trimethyllysine, methylhistidine, dehydrobutyrine, dehydroalanine, α-aminobutyric acid, β-alanine, γ-aminobutyric acid, homocysteine, homoserine, citrulline, ornithine and other amino acids that may be isolated from a natural source and/or that may be chemically synthesized, for instance, as may be found in Proteins, Peptides and Amino Acids Sourcebook (White, J. S, and White, D. C., 2002 Humana Press, Totowa, N.J.) or in Amino Acid and Peptide Synthesis (Jones, J., 2002 Oxford Univ. Press USA, N.Y.) or in Unnatural Amino Acids, ChemFiles Vol. 1, No. 5 (2001 Fluka Chemie GmbH; Sigma-Aldrich, St. Louis, Mo.) or in Unnatural Amino Acids II, ChemFiles Vol. 2, No. 4 (2002 Fluka Chemie GmbH; Sigma-Aldrich, St. Louis, Mo.). Additional descriptions of natural and/or non-natural amino acids may be found, for example, in Kotha, 2003 Acc. Chem. Res. 36:342; Maruoka et al., 2004 Proc. Nat. Acad. Sci. USA 101:5824; Lundquist et al., 2001 Org. Lett. 3:781; Tang et al., 2002 J. Org. Chem. 67:7819; Rothman et al., 2003 J. Org. Chem. 68:6795; Krebs et al., 2004 Chemistry 10:544; Goodman et al., 2001 Biopolymers 60:229; Sabat et al., 2000 Org. Lett. 2:1089; Fu et al., 2001 J. Org. Chem. 66:7118; and Hruby et al., 1994 Meths. Mol. Biol. 35:249. The standard three-letter abbreviations and 1-letter symbols are used herein to designate natural and non-natural amino acids.

Other non-natural amino acids or amino acid analogues are known in the art and include, but are not limited to, non-natural L or D derivatives (such as D-amino acids present in peptides and/or peptidomimetics such as those presented above and elsewhere herein), fluorescent labeled amino acids, as well as specific examples including O-methyl-L-tyrosine, an L-3-(2-naphthyl)alanine, a 3-methyl-phenylalanine, 3-idio-tyrosine, O-propargyl-tyrosine, homoglutamine, an O-4-allyl-L-tyrosine, a 4-propyl-L-tyrosine, a 3-nitro-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-acetyl-L-phenylalanine, an m-acetyl-L-phenylalanine, selenomethionine, telluromethionine, selenocysteine, an alkyne phenylalanine, an O-allyl-L-tyrosine, an O-(2-propynyl)-L-tyrosine, a p-ethylthiocarbonyl-L-phenylalanine, a p-(3-oxobutanoyl)-L-phenylalanine, a p-benzoyl-L-phenylalanine, an L-phosphoserine, a phosphonoserine, a phosphonotyrosine, homopropargyglycine, azidohomoalanine, a p-iodo-phenylalanine, a p-bromo-L-phenylalanine, dihydroxy-phenylalanine, dihydroxyl-L-phenylalanine, a p-nitro-L-phenylalanine, an m-methoxy-L-phenylalanine, a p-iodo-phenylalanine, a p-bromophenylalanine, a p-amino-L-phenylalanine, and an isopropyl-L-phenylalanine, trifluoroleucine, norleucine ("Nle"), D-norleucine ("dNle" or "D-Nle"), 5-fluoro-tryptophan, para-halo-phenylalanine, homo-phenylalanine ("homo-Phe"), seleno-methionine, ethionine, S-nitroso-homocysteine, thia-proline, 3-thienyl-alanine, homo-allyl-glycine, trifluoroisoleucine, trans and cis-2-amino-4-hexenoic acid, 2-butynyl-glycine, allyl-glycine, para-azido-phenylalanine, para-cyano-phenylalanine, para-ethynyl-phenylalanine, hexafluoroleucine, 1,2,4-triazole-3-alanine, 2-fluoro-histidine, L-methyl histidine, 3-methyl-L-histidine, β.-2-thienyl-L-alanine, β-(2-thiazolyl)-DL-alanine, homopropargyglycine (HPG) and azidohomoalanine (AHA) and the like.

In certain embodiments a natural or non-natural amino acid may be present that comprises an aromatic side chain, as found, for example, in phenylalanine or tryptophan or analogues thereof including in other natural or non-natural amino acids based on the structures of which the skilled person will readily recognize when an aromatic ring system is present, typically in the form of an aromatic monocyclic or multicyclic hydrocarbon ring system consisting only of hydrogen and carbon and containing from 6 to 19 carbon atoms, where the ring system may be partially or fully saturated, and which may be present as a group that includes, but need not be limited to, groups such as fluorenyl, phenyl and naphthyl.

In certain embodiments a natural or non-natural amino acid may be present that comprises a hydrophobic side chain as found, for example, in alanine, valine, isoleucine, leucine, proline, phenylalanine, tryptophan or methionine or analogues thereof including in other natural or non-natural amino acids based on the structures of which the skilled person will readily recognize when a hydrophobic side chain (e.g., typically one that is non-polar when in a physiological milieu) is present. In certain embodiments a natural or non-natural amino acid may be present that comprises a basic side chain as found, for example, in lysine, arginine or histidine or analogues thereof including in other natural or non-natural amino acids based on the structures of which the skilled person will readily recognize when a basic (e.g., typically polar and having a positive charge when in a physiological milieu) is present.

Angiotensin-like factor polypeptides and proteins disclosed herein may include L- and/or D-amino acids so long as the biological activity of the polypeptide is maintained. The isolated angiotensin-like factor polypeptides and proteins also may comprise in certain embodiments any of a variety of known natural and artificial post-translational or post-synthetic covalent chemical modifications by reactions that may include glycosylation (e.g., N-linked oligosaccharide addition at asparagine residues, O-linked oligosaccharide addition at serine or threonine residued, glycation, or the like), fatty acylation, acetylation, PEGylation, and phosphorylation. Polypeptides herein disclosed may further include analogs, alleles and allelic variants which may contain amino acid deletions, or additions or substitutions of one or more amino acid residues with other naturally occurring amino acid residues or non-natural amino acid residues.

Peptide and non-peptide analogs may be referred to as peptide mimetics or peptidomimetics, and are known in the pharmaceutical industry (Fauchere, J. Adv. Drug Res. 15:29 (1986); Evans et al. J. Med. Chem. 30: 1229 (1987)). These compounds may contain one or more non-natural amino acid residue(s), one or more chemical modification moieties (for example, glycosylation, pegylation, fluorescence, radioactivity, or other moiety), and/or one or more non-natural peptide bond(s) (for example, a reduced peptide bond: —CH$_2$—NH$_2$—). Peptidomimetics may be developed by a variety of methods, including by computerized molecular modeling, random or site-directed mutagenesis, PCR-based strategies, chemical mutagenesis, and others.

Hence according to certain presently disclosed embodiments an angiotensin-like factor may comprise a polypeptide of no more than 20, 19, 18, 17, 16, 15, 14, 13, 12, 11, 10, 9, 8, 7, 6, 5, 4 or 3 amino acids, or a peptidomimetic thereof, of general formula I:

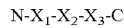

$$N\text{-}X_1\text{-}X_2\text{-}X_3\text{-}C \quad\quad\quad [I]$$

wherein N is an amino terminus of the peptide or peptidomimetic and consists of 0, 1, 2, 3, 4, 5, 6, 7, 8, 9, 10, 11, 12, 13, 14, 15, 16 or 17 amino acids that are independently selected from natural and non-natural amino acids, C is a carboxy terminus of the peptide or peptidomimetic and consists of 0, 1, 2, 3, 4, 5, 6, 7, 8, 9, 10, 11, 12, 13, 14, 15, 16 or 17 amino acids that are independently selected from natural and non-natural amino acids, $X_1$ is a natural or non-natural amino acid having an aromatic side chain, $X_2$ is a natural or non-natural amino acid having as hydrophobic side chain, and $X_3$ is as natural or non-natural amino acid having a basic side chain.

Accordingly in these and other embodiments it will be appreciated that the amino terminus of certain angiotensin-like factors may consist of 1-17 independently selected natural or non-natural amino acids, and/or that in certain embodiments the carboxy terminus of the angiotensin-like factor may consist of 1-17 independently selected natural or non-natural amino acids, where such amino and carboxy termini may have any sequence so long as the isolated angiotensin-like factor is of no more than 3-20 amino acids and comprises N-$X_1$-$X_2$-$X_3$-C as recited herein, and is capable of specifically binding to the cell surface c-Met receptor.

Disclosed herein are a number of representative angiotensin-like factors that comprise N-$X_1$-$X_2$-$X_3$-C [I], and/or N-$X_1$-$X_2$-$X_3$-$X_4$-$X_5$-$X_6$-$X_7$-C [III], as recited herein and that are capable of specifically binding to the cell surface c-Met receptor and/or of inhibiting (including competitively inhibiting) binding of a native HGF hinge polypeptide (e.g., a polypeptide comprising the amino acid sequence set forth in SEQ ID NO:82) to the cell surface c-Met receptor and/or of substantially inhibiting assembly of non-covalent native HGF homodimers, such that in view of the present disclosure those familiar with the art will be able readily to make and use additional angiotensin-like factors according to the present embodiments. For example, determination of the three-dimensional structures of representative angiotensin-like factors may be made through routine methodologies such that substitution of one or more amino acids with selected natural or non-natural amino acids can be virtually modeled for purposes of determining whether a so derived structural variant retains the space-filling properties of presently disclosed species. See, for instance, Donate et al., 1994 Prot. Sci. 3:2378; Bradley et al., Science 309: 1868-1871 (2005); Schueler-Furman et al., Science 310:638 (2005); Dietz et al., Proc. Nat. Acad. Sci. USA 103:1244 (2006); Dodson et al., Nature 450: 176 (2007); Qian et al., Nature 450:259 (2007). Some additional non-limiting examples of computer algorithms that may be used for these and related embodiments, such as for rational design of angiotensin-like factors as provided herein, include Desktop Molecular Modeler (See, for example, Agboh et al., J. Biol. Chem., 279, 40: 41650-57 (2004)), which allows for determining atomic dimensions from space-filling models (van der Waals radii) of energy-minimized conformations; GRID, which seeks to determine regions of high affinity for different chemical groups, thereby enhancing binding, Monte Carlo searches, which calculate mathematical alignment, and CHARMM (Brooks et al. (1983) J. Comput. Chem. 4:187-217) and AMBER (Weiner et al (1981) J. Comput. Chem. 106: 765), which assess force field calculations, and analysis (see also, Eisenfield et al. (1991) Am. J. Physiol. 261:C376-386; Lybrand (1991) J. Pharm. Belg. 46:49-54; Froimowitz (1990) Biotechniques 8:640-644; Burbam et al. (1990) Proteins 7:99-111; Pedersen (1985) Environ. Health Perspect. 61:185-190; and Kini et al. (1991) J. Biomol. Struct. Dyn. 9:475-488).

In certain other presently disclosed embodiments the isolated angiotensin-like factor may comprise a polypeptide of no more than 20, 19, 18, 17, 16, 15, 14, 13, 12, 11, 10, 9, 8, 7, 6, 5, 4 or 3 amino acids, or a peptidomimetic thereof, said polypeptide comprising (i) a tripeptide having an amino acid sequence that is selected from the group consisting of: Lys-Asp-Tyr, Leu-Asp-Tyr, Asp-Tyr-Ile, Tyr-Ile-Arg, Ile-Arg-Asn, and Arg-Asn-Cys, and (ii) at least one of an amino terminus and a carboxy terminus as described herein, each of said amino terminus and said carboxy terminus consisting of 0, 1, 2, 3, 4, 5, 6, 7, 8, 9, 10, 11, 12, 13, 14, 15, 16 or 17 amino acids that are independently selected from natural and non-natural amino acids, as also described herein. In certain related embodiments such a polypeptide or peptidomimetic comprises the amino acid sequence Nle-Tyr-Leu-Ψ-His-Pro-Phe as set forth in SEQ ID NO:43, wherein ill consists of a reduced peptide bond of formula II:

—CH$_2$—NH$_2$—      [II].

In certain other presently disclosed embodiments the isolated angiotensin-like factor may comprise the polypeptide or peptidomimetic of general formula [I] as described above and which comprises at least one amino acid sequence selected from SEQ ID NOS: 9, 25, 33, 41, 42, 45-50, 52-81 and others disclosed herein, which sequences are set forth in the Sequence Listing and certain representative examples of which are also presented here:

```
                                         (SEQ ID NO: 9)
Asp-Arg-Val-Tyr-Ile-His-Pro-Phe-His-Leu, (SEQ ID NO: 25)
Arg-Val-Tyr-Ile-His-Pro-Phe, (SEQ ID NO: 33)
Val-Tyr-Ile-His-Pro-Phe, (SEQ ID NO: 41)
Nle-Tyr-Ile-His-Pro-Phe, (SEQ ID NO: 42)
Val-Ψ-Tyr-Leu-Ψ-His-Pro-Phe,
```

```
                                         (SEQ ID NO: 45)
Nle-Ψ-Tyr-Ile-His-Pro-Phe, (SEQ ID NO: 46)
Leu-Ψ-Tyr-Leu-Ψ-His-Pro-Phe, (SEQ ID NO: 47)
Nle-Tyr-Ile-His, (SEQ ID NO: 48)
Nle-Tyr-Ile-(CH$_2$)$_6$-Phe-amide, (SEQ ID NO: 49)
Nle-Tyr-Ile-Sar-Sar-dPhe, (SEQ ID NO: 50)
Asp-Arg-Val-Tyr-Ile-His-Pro-Phe-His-Leu-Leu-Val-Tyr, (SEQ ID NO: 52)
Nle-Tyr-Ile-6(amino) hexanoic acid amide, (SEQ ID NO: 53)
Nle-Tyr-Ile-His-Pro, (SEQ ID NO: 54)
Lys-Tyr-Ile-His-Pro-Phe, (SEQ ID NO: 55)
benzyl-cysteine-Tyr-Ile-His-Pro-Phe, (SEQ ID NO: 56)
dNle-Tyr-Ile-His-Pro-Phe, (SEQ ID NO: 57)
Nle-Tyr-Ile-Ψ-His-Pro-Phe,

[SEQ ID NO: 58]
Nle-Tyr-Val-Ψ-His-Pro-Phe,

[SEQ ID NO: 59]
Nle-Tyr-Nle-Ψ-His-Pro-Phe,

[SEQ ID NO: 60]
Nle-Phe-Leu-Ψ-His-Pro-Phe,

[SEQ ID NO: 61]
Nle-Phe-Ile-Ψ-His-Pro-Phe,

[SEQ ID NO: 62]
Nle-Phe-Val-Ψ-His-Pro-Phe,

[SEQ ID NO: 63]
Nle-Phe-Nle-Ψ-His-Pro-Phe,

[SEQ ID NO: 64]
Nle-Tyr-Leu-Ψ-Arg-Pro-Phe,

[SEQ ID NO: 65]
Nle-Tyr-Ile-Ψ-Arg-Pro-Phe,

[SEQ ID NO: 66]
Nle-Tyr-Val-Ψ-Arg-Pro-Phe,

[SEQ ID NO: 67]
Nle-Tyr-Nle-Ψ-Arg-Pro-Phe,

[SEQ ID NO: 68]
Nle-Phe-Leu-Ψ-Arg-Pro-Phe,

[SEQ ID NO: 69]
Nle-Phe-Ile-Ψ-Arg-Pro-Phe,

[SEQ ID NO: 70]
Nle-Phe-Val-Ψ-Arg-Pro-Phe,

[SEQ ID NO: 71]
Nle-Phe-Nle-Ψ-Arg-Pro-Phe,
```

-continued

Nle-Tyr-Leu-Ψ-Lys-Pro-Phe, [SEQ ID NO: 72]

Nle-Tyr-Ile-Ψ-Lys-Pro-Phe, [SEQ ID NO: 73]

Nle-Tyr-Val-Ψ-Lys-Pro-Phe, [SEQ ID NO: 74]

Nle-Tyr-Nle-Ψ-Lys-Pro-Phe, [SEQ ID NO: 75]

Nle-Phe-Leu-Ψ-Lys-Pro-Phe, [SEQ ID NO: 76]

Nle-Phe-Ile-Ψ-Lys-Pro-Phe, [SEQ ID NO: 77]

Nle-Phe-Val-Ψ-Lys-Pro-Phe, [SEQ ID NO: 78]

Nle-Phe-Nle-Ψ-Lys-Pro-Phe, [SEQ ID NO: 79]

γ-aminobutyric acid-Tyr-Ile, and [SEQ ID NO: 80]

β-Ala-Tyr-Ile, [SEQ ID NO: 81]

D-Nle-Tyr-Ile-6(amino)hexanoic acid amide, [SEQ ID NO: 52]

D-Nle-Cys-Ile-6(amino)hexanoic acid amide. [SEQ ID NO: 143]

wherein Ψ consists of a reduced peptide bond of formula II:

—CH₂—NH₂—  [II].

Examples of angiotensin-like factors that may be used according to certain embodiments include peptides, polypeptides or peptidomimetics thereof having the following structural formulae, where it is to be understood that according to certain other embodiments it is expressly contemplated that one or more of the following peptides or peptidomimetics thereof may not be used. Accordingly, in these and related embodiments an angiotensin-like factor may include at least one peptide or polypeptide, or a peptidomimetic thereof, comprising any one of: at least amino acids 4-6 of the native angiotensinogen precursor (SEQ ID NO:50), at least amino acids 4-6 of native angiotensin I (SEQ ID NO:9), at least amino acids 4-6 of native angiotensin II (SEQ ID NO:17), at least amino acids 4-6 of native angiotensin III (SEQ ID NO:25), native angiotensin IV (SEQ ID NO:33); COMPOUND 1 (SEQ ID NO:41) [Nle-Tyr-Ile-His-Pro-Phe]; COMPOUND 2 (SEQ ID NO:43) [Nle-Tyr-Leu-Ψ-His-Pro-Phe]; COMPOUND 3 (SEQ ID NO:47) [Nle-Tyr-Ile-His]; COMPOUND 4 [Nle-Tyr-Ile-6(amino) hexanoic acid amide] (SEQ ID NO:52); COMPOUND 5 (SEQ ID NO:42) [Val-Ψ-Tyr-Leu-Ψ-His-Pro-Phe]; COMPOUND 6 (SEQ ID NO:45) [Nle-Ψ-Tyr-Ile-His-Pro-Phe]; COMPOUND 8 (SEQ ID NO:46) [Leu-Ψ-Tyr-Leu-Ψ-His-Pro-Phe]; COMPOUND 9 (SEQ ID NO:48) [Nle-Tyr-Ile-(CH₂)₆-Phe-amide]; COMPOUND 10 (SEQ ID NO:49) [Nle-Tyr-Ile-Sar-Sar-dPhe], COMPOUND 11 (SEQ ID NO:53) [Nle-Tyr-Ile-His-Pro]; COMPOUND 12 (SEQ ID NO:54) [Lys-Tyr-Ile-His-Pro-Phe]; COMPOUND 13 (SEQ ID NO:55) [benzyl-cysteine-Tyr-Ile-His-Pro-Phe]; COMPOUND 14 [γ-aminobutyric acid-Tyr-Ile]; COMPOUND 15 [β-Ala-Tyr-Ile]; COMPOUND 16 (SEQ ID NO:56) [dNle-Tyr-Ile-His-Pro-Phe];

Nle-Tyr-Ile-Ψ(CH2-NH2)-His-Pro-Phe, [SEQ ID NO: 57]

Nle-Tyr-Val-Ψ(CH2-NH2)-His-Pro-Phe, [SEQ ID NO: 58]

Nle-Tyr-Nle-Ψ(CH2-NH2)-His-Pro-Phe, [SEQ ID NO: 59]

Nle-Phe-Leu-Ψ(CH2-NH2)-His-Pro-Phe, [SEQ ID NO: 60]

Nle-Phe-Ile-Ψ(CH2-NH2)-His-Pro-Phe, [SEQ ID NO: 61]

Nle-Phe-Val-Ψ(CH2-NH2)-His-Pro-Phe, [SEQ ID NO: 62]

Nle-Phe-Nle-Ψ(CH2-NH2)-His-Pro-Phe, [SEQ ID NO: 63]

Nle-Tyr-Leu-Ψ(CH2-NH2)-Arg-Pro-Phe, [SEQ ID NO: 64]

Nle-Tyr-Ile-Ψ(CH2-NH2)-Arg-Pro-Phe, [SEQ ID NO: 65]

Nle-Tyr-Val-Ψ(CH2-NH2)-Arg-Pro-Phe, [SEQ ID NO: 66]

Nle-Tyr-Nle-Ψ(CH2-NH2)-Arg-Pro-Phe, [SEQ ID NO: 67]

Nle-Phe-Leu-Ψ(CH2-NH2)-Arg-Pro-Phe, [SEQ ID NO: 68]

Nle-Phe-Ile-Ψ(CH2-NH2)-Arg-Pro-Phe, [SEQ ID NO: 69]

Nle-Phe-Val-Ψ(CH2-NH2)-Arg-Pro-Phe, [SEQ ID NO: 70]

Nle-Phe-Nle-Ψ(CH2-NH2)-Arg-Pro-Phe, [SEQ ID NO: 71]

Nle-Tyr-Leu-Ψ(CH2-NH2)-Lys-Pro-Phe, [SEQ ID NO: 72]

Nle-Tyr-Ile-Ψ(CH2-NH2)-Lys-Pro-Phe, [SEQ ID NO: 73]

Nle-Tyr-Val-Ψ(CH2-NH2)-Lys-Pro-Phe, [SEQ ID NO: 74]

Nle-Tyr-Nle-Ψ(CH2-NH2)-Lys-Pro-Phe, [SEQ ID NO: 75]

Nle-Phe-Leu-Ψ(CH2-NH2)-Lys-Pro-Phe, [SEQ ID NO: 76]

Nle-Phe-Ile-Ψ(CH2-NH2)-Lys-Pro-Phe, [SEQ ID NO: 77]

Nle-Phe-Val-Ψ(CH2-NH2)-Lys-Pro-Phe, and [SEQ ID NO: 78]

Nle-Phe-Nle-Ψ(CH2-NH2)-Lys-Pro-Phe, [SEQ ID NO: 79]

wherein Ψ consists of a reduced peptide bond of formula II:

—CH₂—NH₂—  [II].

Certain other herein disclosed embodiments relate to an isolated angiotensin-like factor that comprises an antibody, including antibodies that specifically bind to the c-Met receptor, and further including those that compete successfully with HGF for binding to the c-Met receptor. Antibodies in these and related embodiments still further may include, in preferred embodiments, antibodies that structurally and/or functionally mimic the HGF hinge region (Lys-Asp-Tyr-Ile-Arg-Asn-Cys, [SEQ ID NO:82]). Accordingly and in certain related embodiments, it is contemplated for the first time that antibodies may be selected for their ability specifically to inhibit competitively the binding interaction between an HGF hinge region as described herein (e.g., a polypeptide that comprises SEQ ID NO:82) and a c-Met receptor. Such antibodies may also in certain embodiments include an anti-idiotype antibody that may be generated against, and specific for, one or more complementarity determining region (CDR) of an immunoglobulin that specifically binds to a HGF hinge region epitope, for example that specifically binds to all or a portion of SEQ ID NO:82 as may occur in a native HGF polypeptide, thereby to find use of such an anti-idiotype antibody as an angiotensin-like factor as provided herein.

Antibodies may be obtained from a variety of sources and may comprise one or more immunoglobulins of any class or subclass (for example, IgG, IgM, IgD, IgE, IgA, or any combination thereof, including, e.g., human $IgG_1$, $IgG_2$, $IgG_3$, $IgG_4$, $IgA_1$, and $IgA_2$, etc., murine $IgG_1$, $IgG_{2A}$, $IgG_{2B}$, etc.) (Harlow, E., and Lane, D., *Antibodies: A Laboratory Manual*, Cold Spring Harbor Laboratory, Cold Spring Harbor, N.Y., 343-348 (1988)). Antibody-producing cells may undergo isotype class switching such that a nucleic acid molecule encoding an Ig $V_L$ or $V_H$ is isolated using methods known in the art and such that it does not include any nucleic acid sequences encoding $C_L$ or $C_H$. The nucleic acid molecule encoding $V_L$ or $V_H$ is then operatively linked to a nucleic acid sequence encoding a $C_L$ or $C_H$ from a different class of immunoglobulin molecule. This may be accomplished by using a vector or nucleic acid molecule that comprises a polynucleotide coding sequence for the $C_L$ or $C_H$ chain, thus switching the antibody from one class to another. The antibody may then be expressed in a cell and collected therefrom to obtain the antibody of the desired isotype.

Antibodies according to these and related embodiments, for use as angiotensin-like factors, may encompass intact immunoglobulin molecules as well as anti-idiotypic antibodies, mutants, fusion proteins, monoclonal antibodies (including chimeric antibodies, "humanized" antibodies, "primatized" antibodies, etc.), polyclonal antibodies, multi-specific antibodies (including bispecific antibodies), affinity matured, as well as antibody fragments of any of these (including Fv, Fab, Fab', F(ab')$_2$, etc.), heteroconjugate antibodies, immunoconjugates, immunoliposomes, or other modifications that comprise an immunoglobulin antigen recognition site of an appropriate specificity, such as an antigen binding site that is capable of specifically binding to a cell surface c-Met receptor in a manner that competitively inhibits HGF binding via the HGF hinge region (SEQ ID NO:82) to the c-Met receptor. Non-limiting examples of forms of antibodies that may be used in these and related embodiments include diabodies, minibodies, Janusins and the like. Antibodies may be produced by any means known in the art, including recombinant or chemical synthesis, or purification from hybridoma cell lines.

In addition, antibodies may be labeled or marked by chemical, physical or physico-chemical means including by conjugation to a detectable agent for use in diagnostic or therapeutic uses. Some examples of detectable agents include enzymes, radioisotopes, fluorescent compounds, colloidal metals, chemiluminescent compounds, and bioluminescent compounds. One skilled in the art will know how readily to implement these or other suitable detectable agents according to relevant immunochemical methodologies by no more than routine experimentation. Antibodies may also, according to related embodiments, be covalently or non-covalently bound to any number of carriers including solid-phase carriers, whether active or inert, and including glass, polystyrene, polypropylene, polyethylene, dextran, nylon, amylases, natural and modified celluloses, polyacrylamides, agarose, magnetite and other suitable carriers.

Certain embodiments contemplate angiotensin-like factors that may be provided as humanized antibodies, which may be obtained, for example, by substituting $C_{H1}$, $C_{H2}$, $C_{H3}$, immunoglobulin hinge domains and/or immunoglobulin framework domains of a non-human antibody with the corresponding human sequence(s) while maintaining one or more or all of the CDRs of the heavy chain or light chain or both. Chimeric antibodies are thus contemplated and generally include antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies. (See U.S. Pat. No. 4,816,567.)

Certain embodiments of the present invention include substantially pure or isolated antibodies, which refers to antibodies that have been removed from native or naturally occurring antibodies and the purified or isolated antibodies are substantially free of contaminants relating to a native or naturally occurring antibody environment.

In other embodiments, there are provided nucleic acid molecules, vectors and host cells that may be used to make mutated antibodies. Such antibodies may be mutated in the variable domains of the heavy and/or light chains to alter a binding property of the antibody (for example, to change the binding affinity), or may be made in a framework region or constant domain (for example, to increase the half-life of the antibody). In still other embodiments, a fusion antibody or immunoadhesin may be made which comprises all or a portion of the antibody linked to another polypeptide. For example, the variable region may be linked to another polypeptide, or the $V_H$ domain may be linked to a first polypeptide while the $V_L$ domain is linked to a second polypeptide that interacts with the first polypeptide. The resulting fusion antibodies may be used to target a particular tissue or cell, as the polypeptide(s) may contain therapeutic agents, such as a toxin, growth factor, or other regulatory protein, or may be a diagnostic agent, such as an enzyme that can be visualized or tracked. Furthermore, fusion antibodies may be generated with two or more single-chain antibodies linked together, forming a divalent or polyvalent antibody on a single polypeptide chain, or a bispecific antibody.

In other embodiments, single chain Fv or scFV antibodies are also contemplated. For example, Kappa bodies (Ill et al., Prot. Eng. 10: 949-57 (1997); minibodies (Martin et al., EMBO J. 13: 5305-9 (1994); diabodies (Holliger et al., PNAS 90: 6444-8 (1993); or Janusins (Traunecker et al., EMBO J. 10: 3655-59 (1991) and Traunecker et al. Int. J. Cancer Suppl. 7: 51-52 (1992), may be prepared using standard molecular biology techniques following the teachings of the present application with regard to selecting antibodies having the desired specificity. In still other embodiments, bispecific or chimeric antibodies may be made that encompass the ligands of the present invention. For example, a chimeric antibody may comprise CDRs and framework regions from different antibodies, while bispecific antibodies may be generated that bind specifically to c-Met through one binding domain and to a second molecule through a second binding domain. These antibodies may be produced through recombinant molecular biological techniques or may be physically conjugated together.

Any of the antibodies considered herein may be derivatized or linked to another molecule (such as a peptide or other label). Typically, the antibodies or portions thereof (whether intact or modified in form) may be derivatized such that the c-Met binding is not adversely affected. For instance, an antibody or antibody portion of the presently disclosed embodiments may be linked (by chemical coupling, genetic fusion, noncovalent association or otherwise), to one or more other agents including another antibody, detection agent, cytotoxic agent, therapeutic agent, and/or a protein or peptide.

Any angiotensin-like factor as provided herein that is capable of altering (e.g., increasing or decreasing in a statistically significant manner) a hepatocyte growth factor activity or a c-Met receptor activity and that is capable of specifically binding to a cell surface c-Met receptor may be used to practice certain presently disclosed embodiments, including a native sequence angiotensin molecule or a precursor, fragment or functional subunit thereof, or a peptide homologue or analogue thereof including an organic small molecule or peptide, and/or a polypeptide variant of a native sequence c-Met receptor ligand.

It should be noted that according to certain preferred embodiments described herein, an angiotensin-like factor comprises all or a portion of an isolated naturally or non-naturally occurring molecule that is capable of functionally and/or structurally mimicking an HGF hinge region, for example, SEQ ID NO: 82 or a polypeptide having 2, 3, 4, 5, 6 or 7 of the amino acids that are present at positions 122-128 of SEQ ID NO:1, or a peptide or non-peptide analogue thereof (such as those exemplified above) as described herein and as will be appreciated by one skilled in the art based on the present disclosure.

Certain related embodiments contemplate a functional molecule, for use as an angiotensin-like factor, that may be capable of producing the same or similar biological effects (i.e., alteration of a HGF activity or a c-Met receptor activity) as those which result from interaction of a specific herein disclosed angiotensin-like factor with a cell surface c-Met receptor, which functional molecule may occur as an organic small molecule, a peptide, an antibody, a glycopeptide, a glycolipid, a polysaccharide, an oligosaccharide, a nucleic acid, a peptidomimetic, an anti-sense polynucleotide, a ribozyme, a nucleic acid triple helix, or a derivative, metabolite, catabolite, precursor, prodrug, or analog thereof, including isolated enantiomeric, diastereomeric and geometric isomers thereof, and mixtures thereof; or a composition or medicament that includes said compound or mixture comprising compounds as described herein.

Figure 1A:
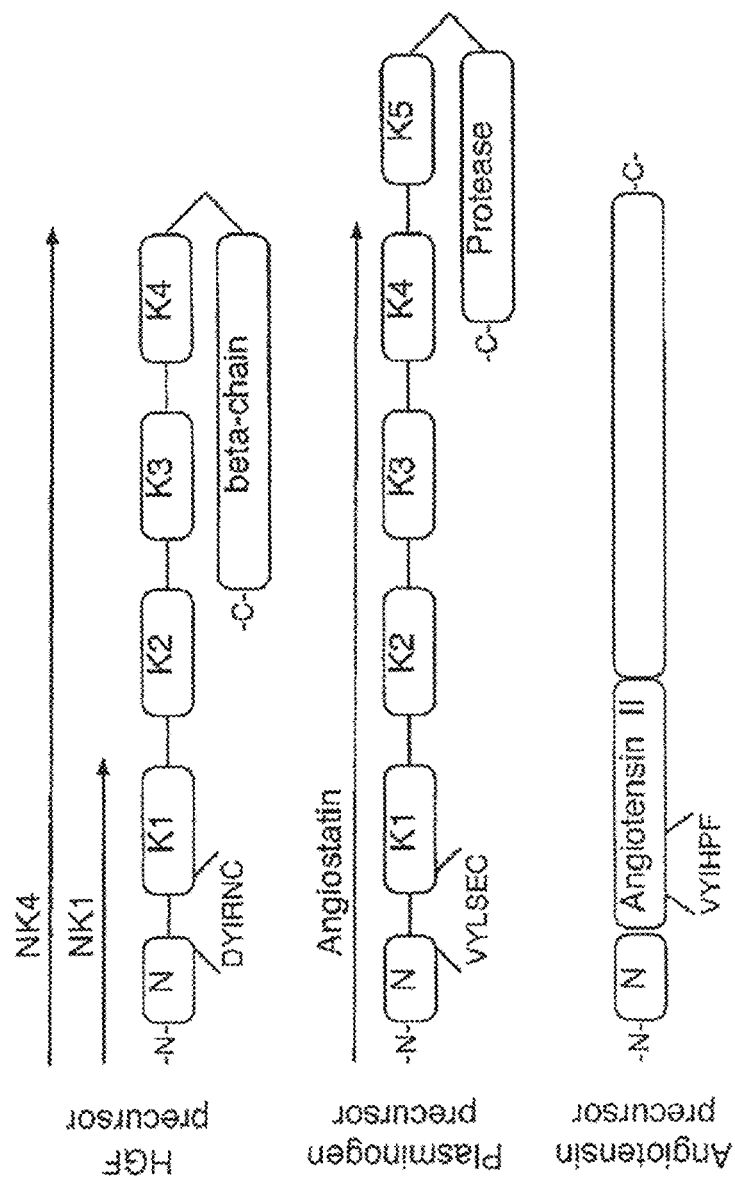
FIG. 1 shows (FIG. 1A) a schematic illustration of HGF, angiostatin and angiotensin homology structures and (FIG. 1B) angiotensin system members and receptor interactions.
Figure 1B:
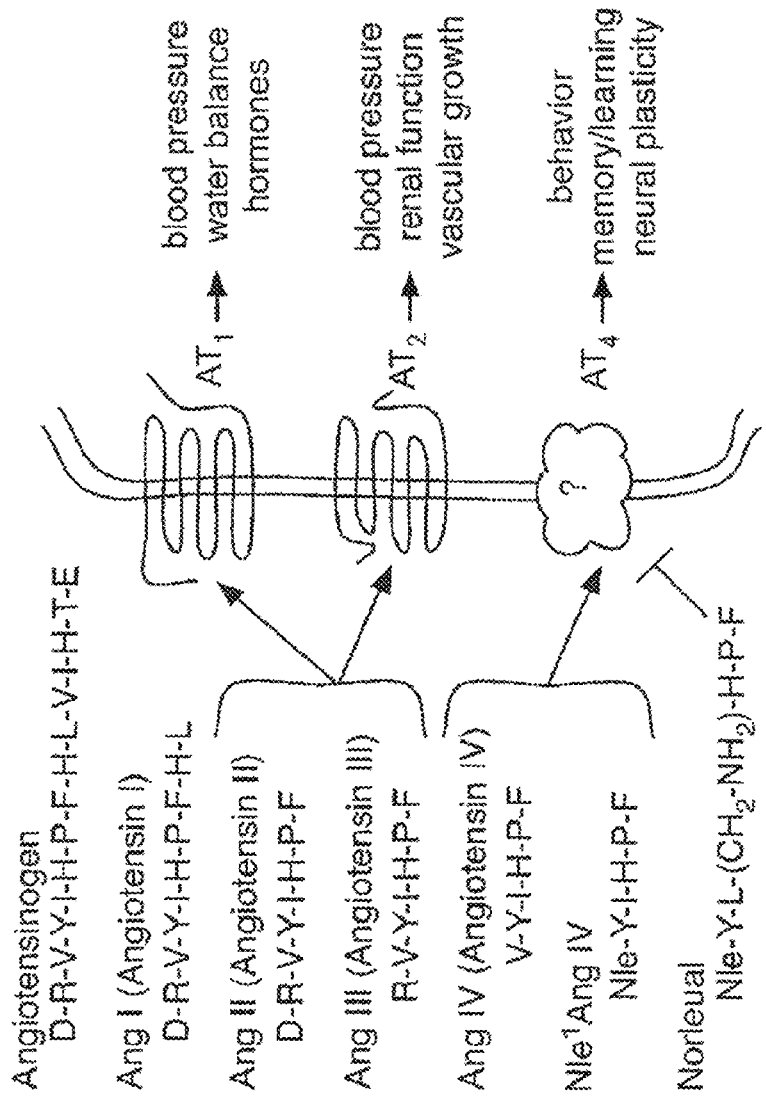

Thus, an angiotensin-like factor according to certain herein disclosed embodiments may refer to part of any angiotensin molecule, including the angiotensinogen precursor molecule, or any part of an angiotensin molecule for which no known receptor has yet been identified. Since presently known or isolated angiotensin peptides are related splice products of the angiotensinogen precursor (see, e.g., FIG. 1), each angiotensin peptide shares amino acid sequence identity, in particular in the regions toward the amino terminal end and middle sections of each angiotensin peptide. As described herein for certain embodiments, these regions appear to be relevant for binding of angiotensin-like factors to the c-Met receptor. Thus, certain embodiments, such as the methods of diagnosing, preventing or treating a condition associated with c-Met receptor dysregulation, relate to the use of an angiotensin-like factor that may comprise the amino acid (or encoding nucleic acid) sequences that are common among angiotensin peptides, including the angiotensinogen precursor, angiotensin 1, angiotensin II, angiotensin III, and angiotensin IV. In certain such embodiments, the angiotensin-like factor may therefore, in addition to being capable of binding to a cell surface c-Met receptor, also be capable of binding to one or several other angiotensin receptors, which in some embodiments may include an angiotensin II receptor and in certain other embodiments may include an angiotensin IV receptor (e.g., IRAP).

However, an angiotensin-like factor according to certain embodiments disclosed herein expressly may not encompass the known full-length native sequence of the angiotensinogen precursor, or any of the known full-length native sequences of the angiotensin I, II, III, or IV peptides or nucleic acids.

Certain embodiments relate to nucleic acid molecules encoding an angiotensin-like factor. Methods for production of desired nucleic acids and/or polypeptides are well known in the art. For example, nucleic acids and/or polypeptides may be isolated from cells or synthesized de novo by chemical synthesis. Such nucleic acids or polypeptides may be incorporated into a vector, and transformed into a host cell. Host cells may be cultured in standard nutrient media plus necessary supplements or additives for inducing promoters, selecting transformants or amplifying the appropriate sequences.

As also described above, certain embodiments also relate to peptidomimetics, or "artificial" polypeptides. Such polypeptides may contain one or more amino acid insertions, deletions or substitutions, one or more altered or artificial peptide bond, one or more chemical moiety (such as polyethylene glycol, glycosylation, label, toxin, or other moiety), and/or one or more non-natural amino acid. Synthesis of peptidomimetics is well known in the art and may include altering naturally occurring proteins or polypeptides by chemical mutagenesis, single or multi-site-directed mutagenesis, PCR shuffling, use of altered aminoacyl tRNA or aminoacyl tRNA synthetase molecules, the use of "stop" codons such as amber suppressors, use of four or five base-pair codons, or other means.

Without wishing to be bound by any particular theory, tumor angiogenesis, or angiogenesis in other contexts such as adipogenesis as may be present in obesity or a condition associated with obesity, such as diabetes or other metabolic diseases, may be promoted by HGF secretion from vascular endothelial cells. Once the endothelial cells are stimulated, proteinases are activated that degrade the local extracellular matrix, which allows the cells to move into the stroma. The endothelial cells proliferate and may ultimately form tubular structures that are capable of fusing with other blood vessels. Tumor angiogenesis is typically not as well orchestrated as angiogenesis related to embryogenesis, corpus luteum formation, wound healing (including dermal, epidermal or other skin wounds), or adipose tissue development, and may result in leaky or non-functional vessels. Thus, one of the problems with administration of present chemotherapy or other tumor-destroying pharmaceutical drugs is that the pharmaceuticals are not able to fully reach the entire tumor, due to this inadequate blood supply. However, the blood supply is typically sufficient enough to allow the established tumor mass to continue to grow.

Further, the binding of HGF to the c-Met receptor is believed to be by way of a functional domain located in the N-terminal portion of the molecule. (Chirgadze et al., Nature Struct. Biol. 6:72 (1999); Schiering et al., PNAS 100(22): 12654 (2003); Gherardi et al., 2003 Proc. Nat. Acad. Sci. USA 100:12039 Gherardi et al., 2006 Proc. Nat. Acad. Sci.

USA 103:4046.) HGF and HGF variants are described, for example, in U.S. Pat. Nos. 5,227,158; 5,316,921; and 5,328,837.

The practice of certain embodiments of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

Unless the context requires otherwise, throughout the specification and claims which follow, the word "comprise" and variations thereof, such as, "comprises" and "comprising" are to be construed in an open, inclusive sense, that is as "including, but not limited to".

Reference throughout this specification to "one embodiment" or "an embodiment" or "an aspect" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Certain embodiments relate to methods, compositions and kits or altering hepatocyte growth factor activity in a cell or plurality of cells. A cell generally indicates a single cell, whereas a plurality of cells indicates more than one cell. The cells may comprise a tissue, organ or entire organism. Furthermore, the cell or cells may be located in vivo, in vitro, or ex vivo. Maintaining cell, tissue and organ cultures are routine procedures for one of skill in the art, the conditions and media for which can be easily ascertained. (See, for example, Freshney, Culture of Animal Cells: A Manual of Basic Technique, Wiley-Liss 5th Ed. (2005); Davis, Basic Cell Culture, Oxford University Press 2nd Ed. (2002)).

In certain embodiments of the present invention, one or more angiotensin-like factors may be used to identify agents that alter hepatocyte growth factor activity or c-Met receptor activity. Such agents may inhibit or enhance signal transduction via an intracellular signaling cascade, leading to cell proliferation. An agent that alters hepatocyte growth factor activity or c-Met receptor activity may alter expression and/or stability of HGF or c-Met, HGF or c-Met protein activity and/or the ability of HGF or c-Met to change phosphorylation states of a substrate. Agents that may be screened within such assays include, but are not limited to, antibodies and antigen-binding fragments thereof, competing substrates or peptides that represent, for example, a catalytic site or a dual phosphorylation motif, antisense polynucleotides and ribozymes that interfere with transcription and/or translation of HGF or c-Met and other natural and synthetic molecules, for example small molecule inhibitors, that bind to and inactivate HGF or c-Met.

Candidate agents for use in a method of screening for an agent that alters HGF activity or c-Met receptor activity according to certain of the present invention embodiments may be provided as a library or collection of compounds, compositions or molecules. Molecules of such a library may typically include compounds known in the art as "small molecules" and having molecular weights less than 1,000 Daltons, and may be less than 900, 800, 700, 600, 500, 400, or 300 Daltons, or any weight therebetween. For example, members of a library of test compounds can be administered to a plurality of samples, each containing at least one HGF or c-Met polypeptide as provided herein, and then assayed for their ability to enhance or inhibit HGF-mediated or c-Met-mediated binding to a substrate, or alteration in the phosphorylation state of a substrate. Compounds so identified as capable of influencing HGF or c-Met function are valuable for therapeutic and/or diagnostic purposes, since they permit treatment and/or detection of diseases associated with HGF activity or c-Met activity. Such compounds are also valuable in research directed to molecular signaling mechanisms that involve HGF or c-Met, and to refinements in the discovery and development of future HGF or c-Met compounds exhibiting greater specificity.

Candidate agents further may be provided as members of a combinatorial library, which preferably includes synthetic agents prepared according to a plurality of predetermined chemical reactions performed in a plurality of reaction vessels. For example, various starting compounds may be prepared employing one or more of solid-phase synthesis, recorded random mix methodologies and recorded reaction split techniques that permit a given constituent to traceably undergo a plurality of permutations and/or combinations of reaction conditions. Furthermore, a number of computer algorithms available in the art allow for generation of members with desired characteristics relating to a particular molecular structure, including a receptor. (See, for example, Pabo et al., Biochem., 25: 5987-5991 (1986); Lazar et al., Prot. Sci., 6: 1167-1178 (1997); Lee, et al. Nature, 352: 448-451 (1991); Colombo et al., J. Am. Chem. Soc., 121: 6895-6903 (1999); Weiner, et al., J. Am. Chem. Soc., 106: 765-784 (1984)).

The resulting products comprise a library that can be screened followed by iterative selection and synthesis procedures, such as a synthetic combinatorial library of peptides (see e.g., PCT/US91/08694, PCT/US91/04666) or other compositions that may include small molecules as provided herein (see e.g., PCT/US94/08542, EP 0774464, U.S. Pat. No. 5,798,035, U.S. Pat. No. 5,789,172, U.S. Pat. No. 5,751, 629). Such a library is included in certain embodiments of the disclosed invention and comprises multiple c-Met ligands, including agonists, partial agonists, and antagonists. Some of the ligands from the disclosed library comprise peptides, as well as peptidomimetics and have exhibited receptor affinities in the sub-picomolar to nanomolar range.

Agents which alter HGF activity or c-Met activity may be identified by combining a candidate agent with a HGF or c-Met receptor polypeptide or a polynucleotide encoding such a polypeptide, in vitro or in vivo, and evaluating the effect of the candidate agent on the HGF activity or c-Met activity using, for example, a representative assay described herein.

For example, HGF activity or c-Met activity may be measured in whole cells transfected with a reporter gene whose expression is dependent upon the activation of an appropriate substrate. For example, appropriate cells (i.e., cells that express HGF or c-Met) may be transfected with a substrate-dependent promoter linked to a reporter gene. In such a system, expression of the reporter gene (which may be readily detected using methods well known to those of ordinary skill in the art) depends upon activation of a substrate. Changes in phosphorylation states of a substrate may be detected based on a change in reporter activity. Candidate agents may be added to such a system, as described above, to evaluate their effect on HGF activity or c-Met activity.

Within other aspects, animal models are provided in which an animal either does not express a functional HGF ligand or c-Met receptor, or expresses an altered HGF ligand or c-Met receptor. Such animals may be generated using standard homologous recombination strategies. Animal models generated in this manner may be used to study activities of HGF ligand or c-Met receptor polypeptides and agents capable of altering HGF activity or c-Met activity in vivo.

Certain embodiments as herein disclosed relate to an angiotensin-like factor that is capable of specifically binding to a c-Met receptor in a cell membrane. A cell membrane may include any cellular membrane, and typically refers to membranes that are in contact with cytosolic components, including intracellular membrane bounded compartments such as mitochondrial inner and outer membranes, intracellular vesicles, vacuoles, ER-Golgi constituents, chloroplasts, other organelles and the like, as well as the plasma membrane.

Angiotensin-like factors that are capable of specifically binding to a c-Met receptor include the angiotensin-like factors that react at a detectable level with the c-Met receptor, and may also react with an angiotensin receptor, but do not react detectably with receptor polypeptides having unrelated sequences. In certain embodiments, the angiotensin-like factor reacts with an angiotensin II receptor. In other specific embodiments, the angiotensin-like factor does not react with an angiotensin II receptor. In some specific embodiments, the angiotensin-like factor reacts with an angiotensin IV receptor. In other specific embodiments, the angiotensin-like factor does not react with an angiotensin IV receptor.

The present disclosure further provides methods for identifying a molecule that interacts with, or specifically binds to, c-Met (or HGF). Such a molecule generally associates with c-Met (e.g. binds specifically to the c-Met receptor) with an affinity constant ($K_a$) of at least $10^4$, preferably at least $10^5$, more preferably at least $1^6$, still more preferably at least $10^7$ and most preferably at least $10^8$. Affinity constants may be determined using well known techniques. Methods for identifying interacting molecules may be used, for example, as initial screens for agents that are capable of altering HGF activity or c-Met receptor activity, or to identify factors that are involved in the in vivo HGF activity or c-Met activity. In addition to standard binding assays, there are many other techniques that are well known for identifying interacting molecules, including yeast two-hybrid screens, phage display and affinity techniques. Such techniques may be performed using routine protocols, which are well known to those having ordinary skill in the art (see, e.g., Bartel et al., In Cellular Interactions in Development: A Practical Approach, D. A. Harley, ed., Oxford University Press (Oxford, UK), pp. 153-179, 1993). Within these and other techniques, candidate interacting proteins (e.g., putative HGF substrates or c-Met substrates) may be phosphorylated prior to assaying for interacting proteins.

Certain embodiments of the disclosed invention comprise an angiotensin-like factor which may include a native angiotensinogen precursor, a native angiotensin amino acid sequence or a fragment or a functional subunit thereof. A fragment of any particular amino acid sequence may include at least one component of a larger amino acid sequence whether or not such fragment is functional. A functional subunit includes at least one component of a larger amino acid sequence that retains a function compared to the larger amino acid sequence from which it was derived. The function of the functional subunit may be the same as the larger sequence, or it may be different in magnitude, in outcome, etc. Thus, functional subunits may include molecules that function as wild-type molecules, dominant negative molecules, or constitutively active molecules.

In addition, encoding polynucleotides or polypeptide variants of an angiotensin-like factor may contain, respectively, one or more nucleotide or amino acid substitutions, additions, deletions, and/or insertions relative to a native (e.g. wildtype, or a predominant or naturally occurring allelic form). In some embodiments, a variant comprises a molecule in which the N-terminal L-amino acid is replaced with a D-amino acid, and in certain other embodiments one or more other amino acids (e.g., not situated at the N-terminus) may, additionally or alternatively, be replaced with a D-amino acid. In certain embodiments, a variant comprises a molecule in which the N-terminal alpha amino acid is replaced with a beta or gamma amino acid. Variants preferably exhibit at least about 75%, 78%, 80%, 85%, 87%, 88% or 89% identity and more preferably at least about 90%, 92%, 95%, 96%, 97%, 98%, or 99% identity to a portion of a native polypeptide sequence or of a polynucleotide sequence that encodes such a native molecule (for example, native HGF, c-Met receptor, or angiotensin-like factor). The percent identity may be readily determined by comparing sequences of the polypeptide or polynucleotide variants with the corresponding portion of a full-length polynucleotide or polypeptide. Some techniques for sequence comparison include using computer algorithms well known to those having ordinary skill in the art, such as Align or the BLAST algorithm (Altschul, J. Mol. Biol. 219: 555-565, 1991; Henikoff and Henikoff, PNAS USA 89:10915-10919, 1992), which is available at the NCBI website (see [online] Internet:<URL: http://www/ncbi.nlm.nih.gov/cgi-bin/BLAST). Default parameters may be used.

Additionally, it has been discovered that rotatability of the chemical bond, for instance, between the hydrophobic and basic amino acids in the general formula described above, may determine whether a particular angiotensin-like factor acts as an agonist or as an antagonist for the c-Met receptor. In particular, as provided herein a number of angiotensin-like factors comprise peptides or polypeptides having one or more reduced peptide bonds, which are known to confer greater freedom of rotation to the atoms on either side of the bond than is permitted by a conventional naturally occurring peptide bond. As such, and according to non-limiting theory, the presence of one or more reduced peptide bonds (e.g., where a conventional peptide bond (—C(=O)NH—) between two amino acids is replaced by —$CH_2$—$NH_2$+—, often symbolized herein as "Ψ" in certain embodiments of the presently described angiotensin-like factors provides flexibility at the molecular level that may enhance the ability of these angiotensin-like factors to interact with c-Met receptor binding sites for HGF and/or with HGF hinge regions. Further according to theory, the presence and location of the reduced peptide bond(s) in an angiotensin-like factor may favor its activity as a c-Met receptor antagonist. Accordingly, in certain preferred embodiments the angiotensin-like factor may comprise one or more reduced peptide bonds, and according to certain embodiments may comprise two, three, four, five, six or more reduced peptide bonds. Thus, as a non-limiting illustrative example, in a heptapeptide such as the peptide having the amino acid sequence set forth in SEQ ID NO:82, or a variant or mutant or fragment or peptidomimetic thereof, a reduced peptide bond may be present in place of any one or more of the peptide bonds linking the amino acids or amino acid analogues at positions 1 and 2, positions 2 and 3, positions 3 and 4, positions 4 and 5, positions 5 and 6, and positions 6 and 7 therein. Typically when such a reduced peptide bond is present in a presently disclosed angiotensin-like factor, it is notated as "Ψ" and comprises or consists of a reduced peptide bond of formula II:

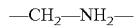
　　　　—CH$_2$—NH$_2$—　　　　　　　　　　　　[II].

Furthermore, computer algorithms are available in the art that enable the skilled artisan to predict the three-dimensional structure of a protein (up to approximately 80 amino acids in size), peptide or peptidomimetic, in order to ascertain functional variants of a particular polypeptide. For instance, variants can be identified wherein all or a portion of the three-dimensional structure is not substantially altered by one or more modification, substitution, addition, deletion and/or insertion. (See, for example, Bradley et al., Science 309: 1868-1871 (2005); Schueler-Furman et al., Science 310:638 (2005); Dietz et al., Proc. Nat. Acad. Sci. USA 103:1244 (2006); Dodson et al., Nature 450:176 (2007); Qian et al., Nature 450:259 (2007)). In this way, one of skill in the art can readily determine whether a particular polypeptide variant, fragment or functional unit thereof is capable of binding a c-Met receptor, and/or is capable of altering hepatocyte growth factor activity or c-Met activity (including but not limited to, e.g., by interfering with non-covalent assembly of full-length HGF polypeptide monomers into the native HGF homodimer), and/or structurally and functionally mimics an HGF hinge region peptide [SEQ ID NO:82] that as disclosed herein, interacts with a c-Met receptor to alter a c-Met activity, including such specific activities as inducing cell proliferation, inducing cell scattering, inducing cell migration, inducing dysregulation of DNA repair, inducing chromosomal repair, inducing cell proliferation, inducing extracellular matrix disruption, inducing dysregulation of apoptosis, inducing cellular extravasation, inducing expression of an adhesion molecule, inducing expression of an angiogenesis-related molecule or otherwise promoting angiogenesis (including, e.g., tumor angiogenesis, adipogenesis or other angiogenesis), inducing neurite growth or axon guidance, inducing cell differentiation, inducing bone regeneration, inducing tissue repair, and inducing activation of intracellular signaling molecules, such as Gab1.

As used herein, inducing may refer to either initiating the response or activity, or up-regulating (i.e. increasing in a statistically significant way) the response or activity once such response or activity is already underway, or both.

Certain encoding polynucleotides, or polypeptide variants, are substantially homologous to a portion of a native (e.g., a naturally occurring, predominant form) gene or peptide, respectively (for example, HGF, c-Met, or angiotensin-like factor). Single-stranded nucleic acids derived (e.g., by thermal denaturation) from such polynucleotide or polypeptide variants are capable of hybridizing under moderately stringent conditions to a naturally occurring DNA or RNA sequence encoding a native polypeptide (or a complementary sequence). A polynucleotide that detectably hybridizes under moderately stringent conditions may have a nucleotide sequence that includes at least 10 consecutive nucleotides, more preferably 11, 12, 13, 14, 15, 16, 17, 18, 19, 20, 21, 22, 23, 24, 25, 26, 27, 28, 29 or 30 consecutive nucleotides complementary to a particular polynucleotide. In certain preferred embodiments such a sequence (or its complement) will be unique to a polypeptide for which alteration of expression is desired, and in certain other embodiments the sequence (or its complement) may be shared by HGF and/or an angiotensin-like factor, and/or c-Met receptor.

Suitable moderately stringent conditions include, for example, pre-washing in a solution of 5×SSC, 0.5% SDS, 1.0 mM EDTA (pH 8.0); hybridizing at 50° C.-70° C., 5×SSC for 1-16 hours (e.g., overnight); followed by washing once or twice at 22-65° C. for 20-40 minutes with one or more each of 2×, 0.5× and 0.2×SSC containing 0.05-0.1% SDS. For additional stringency, conditions may include a wash in 0.1×SSC and 0.1% SDS at 50-60° C. for 15-40 minutes. As known to those having ordinary skill in the art, variations in stringency of hybridization conditions may be achieved by altering the time, temperature, and/or concentration of the solutions used for pre-hybridization, hybridization, and wash steps. Suitable conditions may also depend in part on the particular nucleotide sequences of the probe used, and of the blotted nucleic acid sample. Accordingly, it will be appreciated that suitably stringent conditions can be readily selected without undue experimentation when a desired selectivity of the probe is identified, based on its ability to hybridize to one or more certain sequences while not hybridizing to certain other sequences.

Preferred embodiments of the disclosed invention include angiotensin-like factors that are capable of binding specifically to a cell surface c-Met receptor. Once bound, a given angiotensin-like factor may act as an agonist, a partial agonist, or an antagonist. Generally, it is understood in the art that a c-Met receptor agonist refers to any molecule that mimics the effect of HGF to alter a biological activity mediated by the c-Met receptor, and specifically changes the function or expression of the receptor, or alters the efficiency of signaling through the c-Met receptor, thereby altering (i.e. increasing or decreasing in a statistically significant manner) an existing biological activity or triggering a new biological activity, such as those described herein. For example, angiotensin-like factors that are capable, as disclosed herein, of acting as agonist ligands of the c-Met receptor may support c-Met-mediated cell behavior such as cellular proliferation, tubular morphogenesis, and/or cell migration. In vivo, c-Met agonists may facilitate wound healing, enhance angiogenesis, increase cognitive function or participate in mechanisms that mediate other physiological processes.

Alternatively, a c-Met receptor antagonist may generally refer to any molecule that partially or fully blocks, inhibits or neutralizes a biological activity mediated by a c-Met receptor, by preventing the binding of another ligand (such as HGF) to the c-Met receptor or otherwise interfering with the signaling of the receptor, thereby substantially blocking, e.g., inhibiting in a statistically significant manner at least 10%, 20%, 30%, 40%, 50%, 60%, 70%, 75%, 80%, 85%, 90%, 95%, 96%, 97%, 98% or more, of the biological activity mediated by the receptor in the absence of the antagonist.

Certain embodiments relate to methods and compositions (and kits) for diagnosing, preventing or treating a subject with a condition associated with c-Met receptor dysregulation. Certain embodiments contemplate such a subject which may refer to any organism to be treated (either preventatively or responsively), or diagnosed by the compositions and/or methods disclosed herein. Such organism may include, but need not be limited to a vertebrate, including in certain embodiments a mammal, which in certain further embodiments may be a human; in other embodiments the vertebrate may be a bird, a fish, an amphibian, a reptile or another vertebrate.

Certain embodiments relate to nucleic acids that encode the polypeptides contemplated herein, for instance, angiotensin-like factor polypeptides. As one of skill in the art will recognize, a nucleic acid may refer to a single and/or a double stranded DNA, cDNA or RNA in any form, and may include a positive and a negative strand of the nucleic acid which complement each other, including anti-sense DNA, cDNA and RNA. Also included are siRNA, microRNA, RNA-DNA hybrids, ribozymes, and other various naturally occurring or synthetic forms of DNA or RNA.

Certain embodiments include nucleic acids contained in a vector. One of skill in the art can readily ascertain suitable vectors for use with certain herein disclosed embodiments. A typical vector may comprise a nucleic acid molecule capable of transporting another nucleic acid to which it has been linked, or which is capable of replication in a host organism Some examples of vectors include plasmids, viral vectors, cosmids, and others. Some vectors may be capable of autonomous replication in a host cell into which they are introduced (e.g. bacterial vectors having a bacterial origin of replication and episomal mammalian vectors), whereas other vectors may be integrated into the genome of a host cell upon introduction into the host cell and thereby replicate along with the host genome. Additionally, some vectors are capable of directing the expression of genes to which they are operatively linked (these vectors may be referred to as "expression vectors"). According to related embodiments, it is further understood that, if one or more agents is co-administered to a subject, that each agent may reside in separate or the same vectors, and multiple vectors (each containing a different agent the same agent) may be introduced to a cell or cell population or administered to a subject.

In certain embodiments, the nucleic acid of interest may be operatively linked to certain elements of a vector. For example, polynucleotide sequences that are needed to effect the expression and processing of coding sequences to which they are ligated may be operatively linked. Expression control sequences may include appropriate transcription initiation, termination, promoter and enhancer sequences; efficient RNA processing signals such as splicing and polyadenylation signals; sequences that stabilize cytoplasmic mRNA; sequences that enhance translation efficiency (i.e. Kozak consensus sequences); sequences that enhance protein stability; and possibly sequences that enhance protein secretion. Expression control sequences may be operatively linked if they are contiguous with the gene of interest and expression control sequences that act in trans or at a distance to control the gene of interest.

In addition to vectors, certain embodiments relate to host cells that comprise the vectors disclosed. One of skill in the art readily understands that many suitable host cells are available in the art. A host cell may include any individual cell or cell culture which may receive a vector or the incorporation of nucleic acids and/or proteins, as well as any progeny cells. The term also encompasses progeny of the host cell, whether genetically or phenotypically the same or different. Suitable host cells may depend on the vector and may include mammalian cells, animal cells, human cells, simian cells, insect cells, yeast cells, and bacterial cells. These cells may be induced to incorporate the vector or other material by use of a viral vector, transformation via calcium phosphate precipitation, DEAE-dextran, electroporation, microinjection, or other methods. For example, See Sambrook et al. Molecular Cloning: A Laboratory Manual 2d ed. (Cold Spring Harbor Laboratory, 1989).

Certain embodiments also contemplate transgenic animals or transgenic plants comprising one or more nucleic acid molecule(s) such as polynucleotides encoding one or more of an angiotensin-like factor, a c-Met receptor and HGF, that may be used to generate "knock-out" animals or that may be used to produce angiotensin-like factors. Some examples of transgenic animals that may be used include goats, cows, horses, pigs, rats, mice, rabbits, hamsters, or other animals. The transgenic animals may be chimeric, non-chimeric heterozygotes, or non-chimeric homozygotes. (See, for example, Hogan et al., Manipulating the Mouse Embryo: A Laboratory Manual 2 ed., Cold Spring Harbor Press (1999); Jackson et al., Mouse Genetics and Transgenics: A Practical Approach, Oxford Univ. Press (2000); Pinkert, Transgenic Animal Technology: A Laboratory Handbook, Academic Press (1999).)

Other Therapeutic Agents

In certain embodiments, the present invention provides for administering a second compound comprising at least one therapeutic agent in conjunction with a first compound comprising an angiotensin-like factor. The therapeutic agent may comprise a chemotherapeutic agent, a nucleic acid disrupting agent (for example, a DNA or RNA disrupting agent), a proliferative or anti-proliferative agent, radiation therapy including one or more radiotherapy compounds, a cytotoxic agent, an adhesion molecule (such as an integrin), an anti-inflammatory agent, a cytokine, an antibody, a polypeptide, a polynucleotide, a pro-apoptotic agent, a hormone, a statin, a growth factor, any combination of these or other therapeutic agents.

In certain aspects, synergistic benefits may include the ability to use a lesser dosing or schedule frequency due to higher efficacy of the one or more therapeutic agent; the ability to use the one or more therapeutic agent for a longer duration in the regimen (over days, months or years) due to lower dose needed; the ability to use different, less toxic, therapeutic agents due to increased efficacy; the ability to increase survival of a subject due to reduced toxicity; the ability to decrease non-target tissue or organ damage due to reduced toxicity (including, for example, reduced toxicity to liver, kidneys, immune system or nervous system); and other benefits.

Any number of chemotherapeutic agents may be used with the presently described embodiments in conjunction with administration of an angiotensin-like factor. For example, alkylating agents, such as melphalan ($C_{13}H_{18}C_{12}N_2O_2$) and mitoxantrone; anthracyclines, such as doxorubicin, idarubicin, epirubicin, and daunorubicin; cytokines, such as Interferon-α, Interferon-β, TNF-α, IL-4; monoclonal antibodies (regardless of the source), such as MYLOTRAG® (anti-CD33), anti-CD95, anti-CD20, anti-CD20/yttrium 90, anti-CEA, anti-HER-2, anti-CD20/iodine 131, IgG2a, anti-CD52, anti-CD25, anti-CD30, anti-p185 neu, anti-VEGF, anti-EGR, anti-HER/neu-anti-Fc gamma RI, anti-CTLA-4; statins; vitamins, such as vitamin C (ascorbic acid), super oxide dismutase (SOD-1) or other antioxidants; nucleoside analogs, such as cytosine arabinoside, cyclosporine; rapamycin; silominus; cytoxan; mitoxanthrone; steroids; gemcitabine; proteasome inhibitors, such as Bortezomib® (also called VELCADE®) [(1R)-3-methyl-1-[[(2S)-1-oxo-3-phenyl-2-[(pyrazinylcarbonyl)amino]propyl-]amino]butyl]boronic acid; MG-132; radiation; taxanes, such as paclitaxel and docetaxel; vinca alkaloids, such as vincristine; Arsenic Trioxide; cis-diaminodichroplatanium (II); bleomycin ($C_{55}H_{84}N_{17}O_{21}S_3$); Tamoxifen ($C_{26}H_{29}NO$); cisplatin; alitretinoin; anastrozole; azathioprine; bicalutamide; Trichostatin A, Trichostatin C, Oxamflati, Trapoxin A, FR901228, Apicidin, HC-Toxin, WF27082, Chlamydocin, Salicylihydroxamic acid, Suberoylanilide Hydroxamic Acid, Azelaic Bishydroxamic acid, MW2796, MW2996, 6-(3-chlorophenylureido)carpoic Hydroxamic acid, sodium butyrate, isovalerate, valerate, 4-phenylbutyrate, phenylbutyrate, propionate, butrymide, isobutyramide, phenylacetate, 3-bromopropinate, tributyrin, busulfan; capecitabine; carboplatin; cyclophosphamide; cytarabine; etoposide; exemestane; finasteride; fluorouracil; fulvestrant; gemtuzumab ozogamicin; hydroxyurea; ibritumomab; ifosfamide; imatinib; letrozole; megestrol acetate;

methotrexate; mifepristone; temozolomide; tretinoin; triptorelin; vinorelbine, histone deacetylase inhibitors (HDACs), including sodium valproate, and HDAC class I, class II, class III or others; VEGF receptor ligands; PDGF receptor ligands; Kit inhibitors; Ret inhibitors; AMG706 (available from Amgen, Inc.); EGF receptor ligands; ZD6474 (available from AstraZeneca); MP-412A (available from Aveo Pharmaceuticals, Inc.); serine/theronine inhibitors; RAF inhibitors; FLT-3 ligands; sorafenib (available from Bayer Corp.); BAY 43-9006 (available from Onyx Pharmaceuticals, Inc.); SRC/ABL kinase inhibitors (including dasatinib, available from Bristol-Myers Squibb); trk inhibitors (including lestaurtinib, available from Cephalon, Inc); HER2 inhibitors, EphB4 receptor tyrosine kinase inhibitors (including XL647, available from Exelixis, Inc.); FGF receptor ligands; XL999 (available from Exelixis, Inc.); ErbB-2 inhibitors (such as lapatinib, available from GlaxoSmithKline); c-Kit inhibitors (including MLH518 available from Millennium Pharmaceuticals, Inc.); PKC inhibitors (including PKC412, available from Novartis); STI571 (available from Novartis); AMN107 (available from Novartis); AEE788 (available from Novartis); OSI-930 (available from OSI Pharmaceuticals); OSI-817 (available from OSI Pharmaceuticals); CSF-1R inhibitors, such as sunitinib maleate and SU11248, both available from Pfizer; VDGF-2 inhibitors, including AG-013736, available from Pfizer; SIR2 family members, such as Hst1p and Sir2p, Sir3p, and Sir4p; MICA or MICB ligands; statins; demethylating agents (including decitabine and 5-deazacytidine); gemcitabine; adjuvants; anti-sense RNA or DNA; siRNA; ribozymes or other enzymes; oligonucleotides, including DNA, RNA or any combination thereof; cancer vaccines; or others.

In certain embodiments of the invention, a polynucleotide, polypeptide, cytokine (or cytokine inhibitor), or hormone (or hormone blocker) may be a therapeutic agent. Some non-limiting examples include, COX-2, Epidermal Growth Factor (EGF), Erythropoietin ("EPO"), Factor IX, Factor VII, Factor VIII, Factor X, Fibroblast Growth Factor (FGF), G-CSF, GM-CSF, Insulin, Insulin-like Growth Factor (IGF), interferons (e.g., interferon-$\alpha$, interferon-$\beta$, interferon-$\gamma$, interferon-$\epsilon$, interferon-$\zeta$, interferon-$\eta$, interferon-$\kappa$, interferon-$\lambda$, interferon-$\tau$, interferon-$\varsigma$, interferon-$\omega$), interleukins (e.g., IL-1, IL-2, IL-3, IL-4, IL-5, IL-6, IL-7, IL-8, IL-9, IL-10, IL-11, IL-12, etc.), leukemia inhibitory factor, Neutrophil inhibitory factor (NIF), oncostatin M, Matrix metalloproteinases (e.g. MMP-1, MMP-2, MMP-3, MMP-4, MMP-5, MMP-6, MMP-7, MMP-8, MMP-9, MMP-10, MMP-11, MMP-12, MMP-13, etc.), PDGF, SCF, Soluble complement receptor I, Soluble I-CAM 1, Soluble interleukin receptors (IL-1, 2, 3, 4, 5, 6, 7, 9, 10, 11, 12, 13, 14, 15), soluble adhesion molecules, Soluble TNF receptor, Tissue plasminogen activator, Tumor necrosis factor $\beta$ (TNF$\beta$), Tumor necrosis factor receptor (TNFR), Tumor necrosis factor-$\alpha$ (TNF$\alpha$), VEGF, Erb, ERbB2, farnesyl protein transferase, or others or inhibitors of any of these. As is evident from the foregoing, any anti-proliferating, pro-apoptotic, cytotoxic, anti-angiogenic or anti-neoplastic agent may be used according to certain embodiments of the present invention. Alternatively, inhibitors of such agents, or agents that promote or favor angiogenesis, cell proliferation, cell motility, etc. may be used in other embodiments of the invention, depending on the desired outcome.

Methods for Diagnosis, Prevention and Treatment

Certain embodiments provided herein are directed to assay and diagnostic methods to identify agents useful to detect, prevent or treat a condition associated with c-Met dysregulation. Potential candidate agents may be screened according to assays described herein and may be performed on cell samples that are in vivo, in vitro, or ex vivo. Included in these particular embodiments are cell samples, ranging from a single cell or cell contents, to multiple cells, tissues or organs. Any assay that measures the ability of an angiotensin-like factor to interact with a cell or cell contents may be used for a diagnostic assay as described herein. For example, Western blot, ELISA, immunoassay, immunoprecipitation, cross-linking, chromatography, two-hybrid system, RIA, tissue immunohistochemistry, Northern blot, mass spectrometry (including MS-MALDI), IR, x-ray crystallography, immunoblot, FACS, laser scanning imaging, binding to a solid support (such as beads, arrays, columns, etc.) PCR, RT-PCR, or other methods are contemplated.

These diagnostic methods may also be used to determine if a particular cell, tissue, organ, or bodily fluid contains high (e.g. relative in a statistically significant manner, to the level in a control sample from a subject known to be free of c-Met dysregulation) levels of c-Met, which may be indicative of outcome for a subject.

Certain of the presently disclosed invention embodiments include preventative treatment of a subject or cells, tissues or organs of a subject, that is suspected of having or susceptible to a condition associated with c-Met dysregulation. The preventative treatment may be the same as or different from the regimen (dosing and schedule, as well as choice of angiotensin-like factor and/or other therapeutic agents) employed to treat a subject or cells, tissues or organs of a subject that has been confirmed to have a condition associated with c-Met dysregulation. Prevention and/or treatment may also include the use of vaccines comprising compositions disclosed herein, for example by way of illustration and not limitation, one or more angiotensin-like factors and/or c-Met-specific antibodies.

A condition associated with c-Met dysregulation includes any disorder or condition in which underactivity, overactivity or improper activity of a c-Met cellular or molecular event is present. A subject having such a disorder or conditions would benefit from treatment with a composition or method of the presently described embodiments. Some conditions associated with c-Met dysregulation include chronic and acute disorders and diseases, such as those pathological conditions that predispose the subject to a particular disorder. Alternatively, a condition associated with c-Met dysregulation may also be non-pathological (such as, for example, benign skin outgrowths, pregnancy, repair of broken bones or teeth, hair growth or re-growth).

Some non-limiting examples of conditions associated with c-Met receptor dysregulation include hyperproliferative disorders, which refer to states of activated and/or proliferating cells (which may also be transcriptionally overactive) in a subject including tumors, neoplasms, cancer, inflammatory conditions or disease, deposition of adipose tissue, etc. In addition to activated and/or proliferating cells, the hyperproliferative disorder may also include an aberration or dysregulation of cell death processes, whether by necrosis or apoptosis. Such aberration of cell death processes may be associated with a variety of conditions, including inflammatory diseases, viral infections (whether the subject shows symptoms of a viral infection or not), cancer (including primary, secondary malignancies as well as metastasis) and other conditions (such as osteoarthritis and atherosclerosis). Other conditions associated with c-Met receptor dysregulation include arthritis, diabetic retinopathy, macular degeneration, obesity and conditions associated with obesity as described herein and known to the art. In addition, neurological diseases and conditions including but not limited to dementia, Amyotrophic Lateral Sclerosis, Parkinson's Disease, multiple sclerosis, Traumatic Brain Injury (TBI) and/or Spinal Cord Injury may be treated.

According to certain embodiments, virtually any type of cancer may be treated through the use of compositions and methods (and kits) disclosed herein, including but not limited to, organ cancers (e.g. cancer of the liver, kidney, or brain, glioblastoma or other cancer of the nervous system, stomach, ovarian, breast, prostate, other uro-genital, colon or other gastrointestinal, heart, lung, nasopharyngeal, skin, eye, oral, bone, or connective tissue cancer, etc.), as well as hematological cancers (T or B cell lymphomas, myeloma, leukemia, multiple myeloma, acute myeloid leukemia) are considered. Furthermore, "cancer" may refer to any accelerated proliferation of cells, including solid tumors, ascites tumors, blood or lymph or other malignancies; connective tissue malignancies; metastatic disease; minimal residual disease following transplantation of organs or stem cells; multi-drug resistant cancers, primary or secondary malignancies, angiogenesis related to malignancy, or other forms of cancer. Also contemplated by the presently claimed invention are specific embodiments wherein only one of the above types of disease are included, or specific embodiments are not included.

Other conditions associated with c-Met dysregulation include any number of inflammatory and other diseases, including cancer, cirrhosis, AIDS, bacterial or viral infections, endometriosis, inflammatory joint disease, such as arthritis (including osteoarthritis and rheumatoid arthritis), autoimmune disease, allergies (including irritation of skin, mucous membranes, bronchial airways, gastro-intestinal tract, or other tissues as a reaction to foods, airborne or water borne irritants, skin-contacted irritants or other agents), asthma, dermatitis, vasculitis, sequelae of stem cell transplantation, including graft-versus-host diseases, organ transplantation, opthalmologic diseases (such as glaucoma, retinitis, diabetic retinopathy, uveitis, ocular photophobia, macular degeneration), pain associated with any of these, and any combination of these conditions.

Conditions associated with c-Met receptor dysregulation may also include autoimmune diseases, which generally refer to any disease state governed by an abnormal immune response or a self-destructive immune response. Autoimmune disease is associated with a chronic inflammatory condition, with activated immune cells and a persistent inflammatory response that may include infiltration of mononuclear cells, proliferation of fibroblasts, increased connective tissue and blood vessels, pain and tissue destruction. Various autoimmune diseases are well known and well-characterized, for example, rheumatoid arthritis, systemic lupus erythematosus (SLE), Hashimoto's thyroiditis, autoimmune hemolytic anemia, Celiac Sprue, kidney disease (including acute renal failure); Alzheimer's Disease; Huntington's Disease; other neuroinflammation; peripheral neuropathy; inflammatory lung disease; chronic fatigue syndrome, fibromyalgia, scleroderma, type I diabetes, ulcerative colitis, lichen planus, autoimmune hepatitis, Berger's disease, idiopathic thrombocytopenia purpura, rheumatic fever, Graves' disease, chronic fatigue syndrome, multiple sclerosis, vitiligo, pernicious anemia, type I diabetes, pemphigus, polymyositis, dermatomyositis, myasthenia gravis, Crohn's disease, ulcerative colitis, inflammatory bowel disease, psoriasis, dermatitis, scleroderma, Sjogren syndrome, meningitis, encephalitis, uveitis, eczema, respiratory distress syndrome, Reynaud's syndrome, glomerulonephritis, microglial malfunction, chronic infiltrating lung diseases, as well as immune responses associated with acute and delayed hypersensitivity mediated by cytokines and T-lymphocytes typically found in tuberculosis, sarcoidosis, polymyositis, granulomatosis and vasculitis; pernicious anemia (Addison's disease), multiple organ injury syndrome, hemolytic anemia, and others. Also contemplated by the presently claimed invention are specific embodiments wherein only one of the above conditions or diseases are included, or any one or more of the specific conditions or diseases are not included.

Another method of treatment or prevention contemplated by certain embodiments of the present invention includes administering a composition that comprises a desired nucleic acid molecule such that it stably integrates into the chromosome of certain desired cells. For example, such compositions may be integrated into tumor cells or immune system cells in order to regulate growth and/or antibody production.

In other embodiments, the condition associated with c-Met dysregulation includes alteration of angiogenesis. Angiogenesis generally refers to growth of blood vessels or lymphatic vessels. The presently disclosed compositions and methods include those that may find use in diagnosis, prevention and/or treatment of conditions associated with the need for increased angiogenesis, or decreased angiogenesis. In certain instances, increased angiogenesis is desired, such as in diabetes, limb perfusion, hepatic disease, renal disease, neurodegeneration, preeclampsia, respiratory distress, organ transplant, bone or tooth regeneration, hair re-growth, wound or tissue healing, fetal or placental abnormalities, infertility or other reproductive dysfunction, central nervous system impairment or repair, and augmenting or restoring blood flow to ischemic tissues, such as heart or brain following myocardial infarction or stroke. Alternatively, in other instances, decreased angiogenesis is desired, such as for inhibiting tumor growth or metastasis, for treating diabetic retinopathy, for reduction of adipose tissue or prevention of deposition of adipose tissue, or in the field of reproductive biology or animal husbandry, in order to reduce the number of developing embryos in a pregnant subject, as an abortifacient, or as a means to achieve a biochemical infertility or castration of a subject.

With regard to those instances in which it may be desirable to regulate angiogenesis in order to reduce pre-existing adipose tissue or to prevent deposition of adipose tissue, certain herein disclosed embodiments may be used to treat or prevent obesity or a condition associated with obesity. For example, the condition associated with obesity may include a pre-diabetic or diabetic condition, non-alcoholic fatty liver disease, dyslipidemia, hypercholesterolemia, a cardiovascular disease or condition, increased inflammatory activity, thrombosis, immobility, gout, osteoarthritis, a respiratory condition, a psychological condition, and cancer, among other obesity-related conditions known to a person skilled in the relevant art.

In certain instances, the pre-diabetic or diabetic condition may include insulin resistance, type 2 diabetes mellitus, and impaired glucose tolerance. In other instances, the cardiovascular disease or condition may include coronary heart disease, hypertension, congestive heart failure, enlarged heart, cor pulmonalle, varicose veins, pulmonary embolism, atherosclerosis, cardiomyopathy, heart failure, and arrhythmia/sudden death, such as from a heart attack. Respiratory conditions associated with obesity may include dyspnea, obstructive sleep apnea. hypoventilation syndrome, Pickwickian syndrome, and asthma. Psychological conditions associated with obesity may include depression, social stigmatization, body dismorphic disorder, and low self esteem. Obesity related cancerous conditions may include breast, endometrial, colorectal, kidney, prostate, gallbladder, pancreatic and esophogeal, thyroid, lung, cervical, ovarian, liver, and thyroid cancers, among others known to a person skilled in the art.

The compositions and methods of treatment described herein generally relate to both therapeutic treatment and prophylactic or preventive treatment, for instance, in certain embodiments to prevent or lessen an undesired physiological change or disorder, such as the development of a disease, including inflammatory disease or cancer, or in certain other embodiments to promote reduction in another condition, such as loss of body fat or adipose tissue. Further, beneficial or desired clinical results may include, but not be limited to, alleviation or amelioration of symptoms, diminishment of extent of disease, stabilized (not worsening) state of disease, delay or slowing of disease progression, amelioration or palliation of the disease state, and remission (whether partial or total), whether measurable or immeasurable, whether detectable or undetectable, but in preferred embodiments in a manner that can be determined to be statistically significant, such as through the use of established clinical metrics.

In some embodiments of the presently disclosed invention, treatment may refer to prolonging survival of a subject compared to the expected survival if the subject does not receive treatment. Some subjects that may be treated would have already been identified as having a condition associated with c-Met dysregulation. Other subjects that may be treated may be prone to or suspected of having a condition associated with c-Met dysregulation. Typically treatment may include, for example, a regimen that involves administration of an angiotensin-like factor such as a c-Met receptor agonist, or antagonist, or both, at various stages of the disease or conditions to be treated, as well as combination treatment employing such agonists or antagonists, along with other therapeutic agents. Preventative treatment may further involve measuring or quantitatively or qualitatively detecting levels of c-Met or HGF, and/or determining that the level of c-Met or HGF in a subject is abnormally high, potentially diagnosing the subject as being at risk for having or susceptible to or otherwise predisposed to a disease associated with high levels of c-Met or HGF, and implementing a corresponding treatment regimen involving administration of one or more c-Met ligand(s) alone or in conjunction with administration of one or more other therapeutic agent(s). (For example, the angiotensin-like factor compositions may be both neuroprotective as well as neuroregenerative).

In certain instances, the level of c-Met or HGF in a specific tissue, organ, tumor, or biological sample (including a bodily fluid, such as blood, lymph, ascites, urine, saliva, serum, plasma; a cell or plurality of cells, a tissue or plurality of tissues; or an organ, or a plurality of organs, or a biopsy or component of any of these) is about 2-3 times higher than the level of c-Met or HGF in a normal sample. In other instances, the level of c-Met or HGF may be about 3-5, 5-10, 10-100 times or more the amount of c-Met or HGF in a normal sample.

As used herein, administration of a composition or therapy such as an angiotensin-like factor as herein disclosed, or a pharmaceutical composition comprising an angiotensin-like factor, refers to delivering the same to a subject, regardless of the route or mode of delivery. Administration may be effected continuously or intermittently, systemically or locally. Administration may be for treating a subject already confirmed of having a recognized condition, disease or disease-state, or for subjects susceptible to or at risk of developing such a condition, disease or disease-state. Co-administration may include simultaneous and/or sequential delivery of multiple agents in any order and on any dosing schedule.

An effective amount of a therapeutic or pharmaceutical composition refers to an amount sufficient, at dosages and for periods of time needed, to achieve the desired clinical results or beneficial treatment, as described herein. An effective amount may be delivered in one or more administrations. If the administration is to a subject already known or confirmed to have a disease or disease-state, the term "therapeutic amount" may be used in reference to treatment, whereas "prophylactically effective amount" may be used to describe administrating an effective amount to a subject that is susceptible or at risk of developing a disease or disease-state as a preventative course.

Kits and Articles of Manufacture

In certain embodiments, the present invention relates to kits and articles of manufacture relating to one or more compositions and/or methods of the presently disclosure. Kits and/or articles of manufacture may comprise components and/or compositions that are features of the herein disclosed embodiments, as well as packaging materials, instructions for using the components and/or methods, containers, buffers, additional detection reagents, as well as any apparatus necessary for practicing the methods relating to such kits or articles of manufacture.

In certain embodiments, a kit may be used to detect hepatocyte growth factor activity and/or c-Met activity. In certain embodiments, the kit may be used to diagnose a condition associated with c-Met dysregulation. The kit may comprise an indicator, which may be a calorimetric marker, a number, or a computerized sound for indicating the presence or alteration (increase or decrease) of hepatocyte growth factor activity or c-Met receptor activity in a biological sample. The kit may further comprise an apparatus or device for administering the angiotensin-like factor to the biological sample.

In other embodiments, a kit may be used to treat a condition associated with c-Met dysregulation in a subject or biological sample, wherein the kit comprises a first compound comprising an angiotensin-like factor that alters activity of hepatocyte growth factor, and wherein the angiotensin-like factor is capable of specifically binding to a c-Met receptor in a cell membrane. The kit may also contain an apparatus or device for administering the angiotensin-like factor to the subject or biological sample.

Pharmaceutical Compositions

In certain embodiments of the disclosed invention, a pharmaceutical composition comprising at least one herein disclosed composition, such as an angiotensin-like factor as herein disclosed, or a pharmaceutical composition comprising an angiotensin-like factor is administered to a subject. As used herein, a pharmaceutical composition generally refers to the combination of an active pharmaceutical drug or other therapeutic agent and an excipient or carrier, whether inert or active, wherein the pharmaceutical composition comprises at least one angiotensin-like factor that is suitable for therapeutic use, including prophylactic use, in vivo, in vitro, or ex vivo.

In certain embodiments, the present invention relates to formulations of one or more compositions disclosed herein in pharmaceutically-acceptable excipients or carriers for administration to a cell or a subject either alone, or in combination, with one or more other modalities of therapy. It is understood that, if desired, a composition as disclosed herein may be administered in combination with other agents as well, including therapeutic agents. Such compositions may be synthesized de novo or purified from host cells or other biological sources.

It will be apparent that any of the pharmaceutical compositions described herein can contain pharmaceutically acceptable excipients or other carriers, and may contain acceptable salts. Such salts can be prepared, for example, from pharmaceutically acceptable non-toxic bases, including organic bases (e.g. salts of primary, secondary and tertiary amines and basic amino acids) and inorganic bases (e.g. sodium, potassium, lithium, ammonium, calcium and magnesium salts).

While any suitable carrier known to those of ordinary skill in the art may be employed in the pharmaceutical compositions as described herein (e.g., pharmaceutical compositions that comprise the presently disclosed angiotensin-like factor), the type of carrier will typically vary depending on the mode of administration. Compositions of the present invention may in certain embodiments be formulated for any appropriate manner of administration, including for example, topical, oral, nasal, mucosal, intravenous, intratumor, rectal, parenteral, intraperitoneal, subcutaneous and intramuscular administration.

Carriers for use with such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the route of administration, the rate and expected duration of release and the nature of the condition to be treated or prevented.

Certain embodiments of the invention may utilize an alkalinizing agent, which is typically soluble in aqueous phase under physiological pH conditions. Such alkalinizing agents are well known to those in the art and may include alkali or alkaline-earth metal hydroxides, carbonates, bicarbonates, phosphates, sodium borate, as well as basic salts (as discussed herein).

In another illustrative embodiment, biodegradable microspheres (e.g., polylactate polyglycolate) are employed as carriers for the compositions that are herein disclosed. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Another illustrative carrier/delivery system employs a carrier comprising particulate-protein complexes, such as those described in U.S. Pat. No. 5,928,647, which are capable of inducing a class I-restricted cytotoxic T lymphocyte response in a host.

In another illustrative embodiment, calcium phosphate core particles are employed as carriers, adjuvants, or as controlled release matrices for the compositions of this invention. In certain embodiments, an adjuvant may be necessary in order to increase the immune response of the subject. Adjuvants are well known in the art and may include cytokines, dead viruses or bacteria or fragments thereof, antibodies, or any other agent that heightens an immune response.

The pharmaceutical compositions as provided herein will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions described herein may be formulated as lyophilizates.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assailable edible carrier, or they may be enclosed in hard- or soft-shell gelatin capsule, or they may be compressed into tablets, or they may be incorporated directly with the food of the diet. The pharmaceutical composition may take the form of tablets, lozenges, pills, troches, capsules, elixirs, powders, granules, suspensions, emulsions, syrups, or tinctures. Slow-release or delayed-release forms may also be prepared (for example, in the form of coated particles, multi-layer tablets or microgranules).

The compositions may also contain any of a variety of additional components, for example, pharmaceutically acceptable binders, such as gum tragacanth, gum acacia, sodium alginate, carboxymethylcellulose, polyethylene glycol, cornstarch, or gelatin; excipients, such as dicalcium phosphate; a disintegrating agent, such as corn starch, potato starch, methylcellulose, polyvinylpyrrolidone, xanthan gum, bentonite, agar, alginic acid and the like; a lubricant, such as magnesium stearate; a sweetening agent, such as sucrose, lactose, glucose, aspartame or saccharin may be added; a diluent, such as lactose, sorbitol, mannitol, dextrose, kaolin, cellulose, calcium carbonate, calcium silicate or dicalcium phosphate; a flavoring agent, such as peppermint, oil of wintergreen, orange, raspberry, bubblegum, or cherry flavoring, coating agents, such as polymers or copolymers of acrylic acid and/or methacrylic acid and/or their esters, waxes, fatty alcohols, zein, shellac or gluten; preservatives, such as sodium benzoale, vitamin E, alpha-tocopherol, ascorbic acid, methyl paraben, propyl paraben, or sodium bisulphate; lubricants, such as magnesium stearate, stearic acid, sodium oleate, sodium chloride or talc; and/or time delay agents, such as glyceryl monostearate or glyceryl distearate.

In certain embodiments, a tablet or pill may be in the form of a compression coating or alternatively in the form of a spray coating. A compression coating may include a small tablet or pill utilized as part of the compression of a second tablet and wherein the small tablet is located nearly in the center of the rest of the powder compressed outside. A spray coating may include an overcoating of a tablet with the coating preparation containing an active substance.

In certain embodiments, the pharmaceutical compositions of the present invention include "slow-release" or "immediate release" forms. As used herein, "slow-release" generally refers to a release of 20% to 60% in 1 hour and greater than 70% in 6 hours or 40% to 80% in 2 hours, and greater than 70% in 6 hours in 500 ml of water (HCl 0.1N) in USP apparatus 1 (37° C., 100 RPM). Whereas, "immediate release" generally refers to a release of more than 70% in 30 minutes, in 500 ml of water (HCl 0.1N) in USP apparatus 1 (37° C., 100 RPM).

In addition, certain embodiments of the disclosed invention include pharmaceutical compositions in the form of an oral tablet or pill. Such oral formulations may include sections or discrete volumes that contain an active drug. A section of a tablet may form, for example, a layer of a multilayer tablet (i.e. a layer of a bilayer tablet) or a core of a tablet or a coating fully or partially covering a core of a tablet. A section may also be a particle fully or partially covered by a coating or a coating fully or partially covering a particle. The oral formulations described may contain a "fast release" or "slow release" component, or one or more of each. In some embodiments, the pharmaceutical composition comprises multiple therapeutic agents, which may be separated into different sections. In certain embodiments, each section is substantially free of another agent. For example, one section of a tablet comprising an active agent (such as a c-Met receptor ligand) is substantially free of a second compound comprising another therapeutic agent. Substantially free generally refers to less than 10%, less than 5%, less than 3%, less than 1%, less than 0.5%, or less than 0.2% by weight. Furthermore, in certain embodiments, a barrier section may separate components or agents in the pharmaceutical drug formulation.

In certain embodiments, the tablet or pill weighs in the range of 100 mg, 200 mg, 300 mg, 400 mg, 500 mg, 600 mg, 700 mg, 800 mg, and any value therebetween or greater. The oral dosage formulations of certain embodiments of the present invention may be manufactured according to known methods in the art, and may be packaged as known, including in a moisture and/or oxygen and/or light protective packaging material.

In addition, liquid forms of the pharmaceutical compositions may include a liquid carrier, such as water, oils (olive oil, peanut oil, sesame oil, sunflower oil, safflower oil, arachis oil, coconut oil), liquid paraffin, ethylene glycol, propylene glycol, polyethylene glycol, ethanol, propanol, isopropanol, glycerol, fatty alcohols, triglycerides, or mixtures thereof.

If the subject composition is administered parenterally, the composition may also include sterile aqueous or oleaginous solution or suspension. Suitable non-toxic parenterally acceptable diluents or solvents include water, Ringer's solution, isotonic salt solution, 1,3-butanediol, ethanol, propylene glycol or polythethylene glycols in mixtures with water. Aqueous solutions or suspensions may further comprise one or more buffering agents, such as sodium acetate, sodium citrate, sodium borate or sodium tartrate. Of course, any material used in preparing any dosage unit formulation should be pharmaceutically pure and substantially non-toxic in the amounts employed. In addition, the active compounds may be incorporated into sustained-release preparation and formulations. Dosage unit form, as used herein, refers to physically discrete units suited as unitary dosages for the subject to be treated; each unit may contain a predetermined quantity of active compound calculated to produce the desired therapeutic effect in association with the required pharmaceutical carrier. The specification for the dosage unit forms are largely dictated by and directly dependent on the unique characteristics of the active compound and the particular therapeutic or prophylactic effect to be achieved, as well as the limitations inherent in the art of compounding such an active compound for treatment in subjects. Exemplary and non-limiting dosage ranges may be from 0.1-10 mg/kg, 1.0-20 mg/kg, 5.0-50 mg/kg, 10-100 mg/kg, or any values therebetween.

Typically, these formulations will contain at least about 0.01% of the active compound or more by weight of the active substance. However, the percentage of the active ingredient(s) may be varied and may conveniently be between about 1-99%, including about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions presently disclosed may alternatively be incorporated with one or more excipients in the form of a mouthwash, dentifrice, buccal tablet, oral spray, or sublingual orally-administered formulation. Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein topically, orally, subcutaneously, parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. Moreover, for human administration, preparations preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. No. 5,756,353 and U.S. Pat. No. 5,804,212. Likewise, the delivery of drugs using intranasal microparticle resins (Takenaga et al., J Controlled Release 1998 Mar. 2; 52(1-2):81-7) and lysophosphatidyl-glycerol compounds (U.S. Pat. No. 5,725,871) are also well-known in the pharmaceutical arts. Likewise, illustrative transmucosal drug delivery in the form of a polytetrafluoroethylene support matrix is described in U.S. Pat. No. 5,780,045.

In certain embodiments, liposomes, nano capsules, microparticles, microencapsulation, lipid particles, vesicles, and the like, are used for the introduction of the presently disclosed compositions into suitable host cells/organisms. In particular, such compositions may be formulated for delivery either encapsulated in a lipid particle, a liposome, a vesicle, a nanosphere, microsphere or microparticle, a nanoparticle or the like. Alternatively, compositions disclosed herein can be bound, either covalently or non-covalently, to the surface of such carrier vehicles.

The formation and use of liposome and liposome-like preparations as potential drug carriers is generally known to those of skill in the art. Liposomes have been used successfully with a number of cell types that are normally difficult to transfect by other procedures, including T cell suspensions, primary hepatocyte cultures and PC 12 cells (Renneisen et al., J Biol. Chem. 1990 Sep. 25; 265(27):16337-42; Muller et al., DNA Cell Biol. 1990 April; 9(3):221-9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, the use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way. To avoid side effects due to intracellular polymeric overloading, such ultrafine particles (sized around 0.1 μm) may be designed using polymers able to be degraded in vivo. Such particles can be made as described, for example, by Couvreur et al., Crit Rev Ther Drug Carrier Syst. 1988; 5(1):1-20; zur Muhlen et al., Eur J Pharm Biopharm. 1998 March; 45(2):149-55; Zambaux et al. J Controlled Release, 1998 Jan. 2; 50(1-3):31-40; and U.S. Pat. No. 5,145,684.

Dosing Schedules

Routes and frequency of administration of the therapeutic compositions described herein, as well as dosage, will vary from individual to individual, and may be readily established using standard techniques. In general, the pharmaceutical compositions may be administered by injection (e.g., intracutaneous, intramuscular, intravenous or subcutaneous), intranasally (e.g., by aspiration) or orally. Suitable dosage formulations and methods of administering the agents are readily determined by those of skill in the art. In certain instances, the angiotensin-like factor compounds may be administered at about 1 mg/kg, 5 mg/kg, 10 mg/kg, 20 mg/kg, 25 mg/kg, 30 mg/kg, 35 mg/kg 40 mg/kg, 45 mg/kg, 50 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg or any value therebetween or greater. When the angiotensin-like factor compounds described herein are co-administered with at least one other therapeutic agent (such as a chemotherapeutic agent), a synergistic drug interaction may occur that allows for an effective amount dosage to be less than when the particular agent is administered alone.

If more than one angiotensin-like factor compound or more than one therapeutic agent are co-administered, the agents may be administered using different modes, routes or different formulations, as well as different dosing schedules. In addition, multiple same or different angiotensin-like factor compounds and/or multiple same or different other therapeutic agents may be combined in a particular dosing schedule.

In certain instances, angiotensin-like factor doses (and optionally, at least one other therapeutic agent dose) may be provided between 1 day and 14 days over a 30 day period. In certain instances, angiotensin-like factor doses (and optionally, at least one other therapeutic agent dose) may be provided 1, 2, 3, 4, 5, 6, 7, 8, 9, 10, 11, 12, 13, or 14 days over a 60 day period. Alternatively, dosing may be for about 2 weeks, 4 weeks, 6 weeks or 8 weeks. Administering may comprise 1, 2, 3, 4, 5, 6, 7, 8 or more cycles of treatment. Alternate protocols may be appropriate for individual subjects. A suitable dose is an amount of a compound that, when administered as described above, is capable of altering or ameliorating symptoms of a condition associated with c-Met dysregulation, or is at least 10-50% above the basal (i.e., untreated) level, which can be monitored by measuring specific levels of blood components, for example, cytokines, or pharmaceutical drug metabolites.

In general, dosage of any pharmaceutical drug depends on a variety of factors, including age, weight, gender, genetic background, route of administration, disease state, physical condition and other factors. Thus, suitable dosage sizes for the first compound comprising an angiotensin-like factor will vary with the subject, and can be calculated according to various formulas known in the art. In some regimens, only one dose will be administered to a subject per day, and in other regimens multiple doses will be administered in a single day. In addition, the dosing schedule may vary over a period of hours, days, weeks, months or years depending on the goal of the therapy and the disease state of the subject. In certain embodiments, the angiotensin-like factor can be delivered prior to, concurrently with or subsequent to the dosing of two or more therapeutic agents.

In addition, the dosage range of the first compound comprising an angiotensin-like factor may be co-administered with another therapeutic agent in accordance with certain embodiments of the invention. As used herein, "co-administration" includes administration of the first compound substantially simultaneously with at least one other therapeutic agent, or substantially sequentially (either prior to or subsequent to) at least one second compound comprising a therapeutic agent. Thus, the dosage range for co-administration of the first compound with the second compound may be more than or less than the dosage for either compound alone. In certain embodiments of the invention, a synergy results in co-administration, and a lower dosage range for the first compound and/or the second compound would be employed In certain aspects, "co-administration" refers to administration of either the first compound or the second compound within about 10, 20, 30, 40, 50, 60, 70, 80, 90, 100, 120 minutes or less from the time of administering a dose of the other compound (either second compound or first compound, respectively). In other aspects, "co-administration" refers to administration of at least the first compound or the second compound within about 1, 2, 3, 4, 5, 6, 7, 8, 9, 10, 15, 24, 48, 72 hours or less from administering a dose of the other compound (either second or first compound, respectively). In still other embodiments of the present invention, "co-administration" refers to administration of the first compound or the second compound within about 1, 2, 3, 4, 5, 6, 7 days or less from the time of administering a dose of the second compound or first compound, respectively. Thus, in certain instances the first compound comprising an angiotensin-like factor may be administered prior to, concurrently with, or subsequent to at least one second compound comprising another therapeutic agent. In some instances when more than one other therapeutic agent is administered to a subject, the angiotensin-like factor may be administered prior to, concurrently with, or subsequent to one or more or even all of the other therapeutic agents. In other instances the angiotensin-like factor may be administered multiple times while the one or more other therapeutic agents are administered once only, or multiple times. If both the angiotensin-like factor and at least one other therapeutic agent are administered multiple times, then they may be interspaced, or all of one compound may be delivered prior to, concurrently with, or subsequent to one or more other compounds. Thus, any combination of dosing schedules and regimen may be employed within embodiments contemplated according to the present invention.

Also contemplated are multiple doses or dosing schedules, including alternating administering the first compound comprising an angiotensin-like factor and a second compound comprising at least one therapeutic agent, or alternating the first compound with multiple therapeutic agents. If such dosing schedule is employed, it is recognized that "co-administration" of the first compound and the other therapeutic agent(s) may include multiple rounds of administration, in any order of delivering the compounds or agents. The present invention further contemplates that it may be necessary in certain embodiments to administer to the subject a higher initial loading dose of the first compound to achieve peak blood levels, followed by lower maintenance doses. Furthermore, one particular route of administration may be continuous over the course of several minutes, hours or days, while the other therapeutic agent(s) or angiotensin-like factor(s) may be administered by an alternate route or the same route, over the course of several minutes, hours or days.

According to the present disclosure, the first compound comprising an angiotensin-like factor compound and at least a second compound comprising one other therapeutic agent may in some embodiments be delivered to the subject by the same route of administration or different routes of administration, regardless of whether or not they are "co-administered" to the subject.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated subjects as compared to non-treated subjects. Increases in preexisting immune responses to a tumor protein generally correlate with an improved clinical outcome. Such immune responses may generally be evaluated using standard proliferation, cytotoxicity or cytokine assays, which are routine in the art and may be performed using samples obtained from a subject before and after treatment.

The present disclosure also contemplates methods of modifying and derivatizing the herein disclosed angiotensin-like factor(s) to increase desirable properties (for example, binding affinity, activity or the like) or to minimize undesirable properties (such as nonspecific reactivity, toxicity and the like). The principles of chemical derivatization are well understood. In some embodiments, iterative design and chemical synthesis approaches are used to produce a library of derivatized child components from a parent compound. In other embodiments, rational design methods are used to predict and model in silico ligand-receptor interactions prior to confirming results by routine experimentation.

EQUIVALENTS

While particular steps, elements, embodiments and applications of the present invention have been shown and described herein for purposes of illustration, it will be understood, of course, that the invention is not limited thereto since modifications may be made by persons skilled in the art, particularly in light of the foregoing teachings, without deviating from the spirit and scope of the invention. Accordingly, the invention is not limited except as by the appended claims.

The following Examples are presented by way of illustration and not limitation.

EXAMPLES

Example 1

Materials and Methods

This Example describes materials and methods used in the Examples that follow and also in the generation of data for FIGS. 1-19; additional detail regarding experimental procedures and results can be found above under "Brief Description of the Drawings".

Compounds. Norleual (Compound 2, SEQ ID NO:43) was synthesized by Syngene (Bangalore, India) and purified by reverse phase HPLC. HGF (SEQ ID NO:83) was purchased from R&D systems (Minneapolis, Minn., USA).

Antibodies. Antibodies specific for c-Met (SEQ ID NO:84), Gab1, and phospho-tyrosine were purchased from Upstate Biotechnology Inc. (Lake Placid, N.Y., USA). Anti-phospho-tyrosine, HAM1676, was purchased from R&D systems. Phospho-Akt- and Erk-specific antibodies were purchased from Cell Signaling (Danvers, Mass., USA). GAPDH-specific antibody was purchased from Biodesign (Saco, Me., USA).

Cell culture. Cell lines HEK293, MDCK, B16-F0 and B16-F10 (all available from ATCC, Manassas, Va.) were grown in DMEM, 10% fetal bovine serum (FBS). Human Umbilical Vein Endothelial Cells (HUVEC) were grown in EGM-2 (Lonza, Basel Switzerland).

Iodination of $^{125}$I-HGF and $^{125}$I-Norleual. Carrier free HGF was iodinated using the chloramine T method described by Higuchi et al., 1991 Biochem. Biophys. Res. Commun. 176: 599-607. 10 µl of 1.5M NaPO$_4$ (pH 7.4), 4 µl~1 mCi Na $^{125}$I (Perkin Elmer, Waltham Mass., USA), 10 µl of 1 ng/ml HGF were added to 5 µl of 0.1 mg/ml chloramine-T which was added four times at 90 second intervals and stopped by 50 µl of 50 mM N-acetyl-1-tyrosine, 200 µl of 60 mM NaI, and 200 µl of 1.2 mg/ml urea. $^{125}$I-HGF was separated using a G-25 Sephadex (1.5×20 cm) filtration column. Norleual was iodinated using the chloramine-T method as described (Hanesworth et al., 1993 J. Pharmacol. Exp. Ther. 266: 1036-1042). The reaction was performed in 0.2 M sodium phosphate buffer (pH 7.2) containing a total volume of 118 µl (50 µl [1 ng/ml] Norleual, 50 µl additional buffer, 10 µl chloramine T (4 mg/ml), and 8 µl consisting of 2 mCi Na$^{125}$I (Perkin Elmer)]. The reaction was incubated for 2 minutes at room temperature (RT) and stopped with 50 µl Na$_2$S$_2$O$_5$ (5 mg/ml). $^{125}$I-Norleual was purified by HPLC.

$^{125}$I-HGF binding assay. Mouse liver was homogenized in hypotonic buffer fortified with 0.1% bovine serum albumin as described by Hanesworth et al. (1993). 600 µg of membrane protein was incubated with 50 pM $^{125}$I-HGF with various concentrations of HGF or Norleual in a total volume of 100 µl phosphate-buffered saline (PBS) fortified with 0.1% BSA. Binding occurred for one hour on ice. Membranes were pelleted by centrifugation and washed twice with incubation buffer. Radioactivity was counted with a gamma counter (Isomedic 10/880, ICN, Cost Mesa, Calif., USA). Specific binding was calculated and normalized to control counts. Competition fits by PRISM® statistical analysis software (GraphicPad, San Diego, Calif.) were performed according to the manufacturer's instructions.

$^{125}$I-Norleual binding assay. HEK293 cells were grown to confluency in DMEM fortified with 10% FBS. Media was aspirated and cells were washed twice with ice-cold PBS. Cells were lysed with hypotonic buffer and homogenized as described by Zhang et al. (1999, J Pharmacol. Exp. Ther. 289: 1075-1083; 2003 J. Cell Biochem, 88: 408-417). 450 µl of membrane protein was incubated with 1.5 nM $^{125}$I-Norleual with or without Norleual or HGF in a total volume of 250 µl PBS, 0.1% BSA. Tubes were spun and binding was carried out for 60 minutes at RT. Bound and free ligands were separated by vacuum filtration using (Brandel Cell Harvester, Schleicher & Schull, Keene, N.H., USA) 32 glass filters. Radioactivity retained by the filters was measured using a gamma counter. Total counts were normalized to the average of non-displaced $^{125}$I-Norleual (control) and displayed as percent control. Data analysis was preformed using PRISM® statistical analysis software (GraphicPad) per the supplier's recommendations.

Immunoprecipitation and Western blotting. Cells were serum starved for two hours in DMEM before treatment. Cells were harvested using RIPA lysis buffer (Upstate Biotechnol. Inc., Lake Placid, N.Y.) with phosphatase inhibitor cocktails 1 and 2 (Sigma, St Louis, Mo., USA). Protein concentration was determined using the RCA assay (Pierce, Rockford, Ill., USA). Lysates were incubated with antibody overnight at 4° C. Immunoprecipitation controls received mouse non-specific Ig (Upstate). Proteins were captured with protein-A agarose (Upstate) and were washed with PBS. Proteins were resolved using SDS-PAGE electrophoresis (Criterion, BioRad, Hercules, Calif., USA), transferred to nitrocellulose, and incubated with appropriate antibodies. Proteins were visualized using the Supersignal West Pico Chemiluminescent Substrate system (Pierce). The film images were digitized and analyzed using TotalLab™ software (AmershamPharmacia/GE HealthCare, Piscataway, N.J.).

Aortic ring assay. 48-well plates were coated with Growth Factor Reduced MATRIGEL™ (BD Biosciences, San Jose, Calif., USA, thick gel method). Under microscopic dissection, the thoracic aorta of a 6 week-old C57 mouse was cut into 0.5 mm sections, washed in PBS, and placed in the MATRIGEL™-coated wells. The rings were incubated for 4 days in growth-factor-containing EGM-2 (Lonza Biosciences, Rockland, Me. and Basel, Switzerland) with or without Notional at 37° C. in 5% CO$_2$/air. Photos were taken and angiogenic area was measured using Image J (Image Processing and Data Analysis in Java, available from NIH, Bethesda, Md.). Areas were normalized to average control area.

Scattering assay. MDCK cells were grown to confluency on coverslips. The coverslips were transferred to fresh plates and Norleual, HGF, and/or vehicle were added. Plates were incubated at 37° C. with 5% CO$_2$ for 48 hours. Media was removed and cells were methanol fixed. Cells were stained with Diff-Quik Wright-Giemsa (Dade-Behring, Newark, Del., USA). Digital images of each coverslip sector (top, bottom, left, and right) were acquired using a Zeiss Axiovert 40 inverted microscope. Scattering was scored in blinded fashion by comparison to a set of calibration scattering images by two investigators. The scores for each cover slip were averaged and HGF and HGF+Norleual coverslip scattering was normalized to control scattering.

Scratch Assay. Confluent B16-F10 cells in 48 well plates were scratched with a 200 µl pipette tip. Wells were treated with vehicle, HGF, and/or Norleual. Photos were taken at various time points. Photos were graded by two investigators.

Primary tumor melanoma cancer model. Six-month old male C57BL/16 mice were anesthetized and 500 000 B16-F0 cells were injected subcutaneously, and a slow release ethylene vinyl acetate, ELVAX® drug pellets (DuPont, Wilmington, Del., USA) containing Norleual or BSA were surgically implanted intramuscularly into the gluteus maximus at a dose of 21 µg/kg/day. Tumors were measured with digital calipers every two to three days and volumes were calculated using the equation: $[V=(4/3)*pi*r^3]$. Upon daily visual assessment, appropriate measures were taken if warranted (adhering to the guidelines of Part 3 of the Washington State University Guide for the Care and Use of Laboratory Animals).

In vivo metastasis. Six to eight month old C57BL/6 mice were injected with 400 000 B16-F10 cells in 200 µl PBS by tail vein injection. Two to three weeks later, mice were anesthetized and lungs were perfused with PBS and removed. Photos were taken and lungs were solubilized in 1% TRITON™ X-100, 20 mM Tris, 0.15 M NaCl, 2 mM EDTA, and 0.02% sodium azide. Samples were disrupted by sonicaton (Mixonix, Farmingdale, N.Y. USA.) and spun. The supernate was transferred to a 96 well plate and melanin absorbance at 410 nm was measured using a plate reader (Biotek SYNERGY™ 2 plate reader, Winooski, Vt., USA).

Statistics. Independent one-way analysis of variance (ANOVA)s (InStat v.3.05, GraphPad and PRISM® statistical analysis software) were used to determine differences among groups, Tukey-Kramar or Bonferroni's multiple comparison post-hoc tests were performed where necessary. Statistical comparisons of two groups were determined using the two-tailed Student's t-test (InStat and PRISM® statistical analysis software) with a level of significance of 0.05.

Example 2

Figures 2A, 2B:
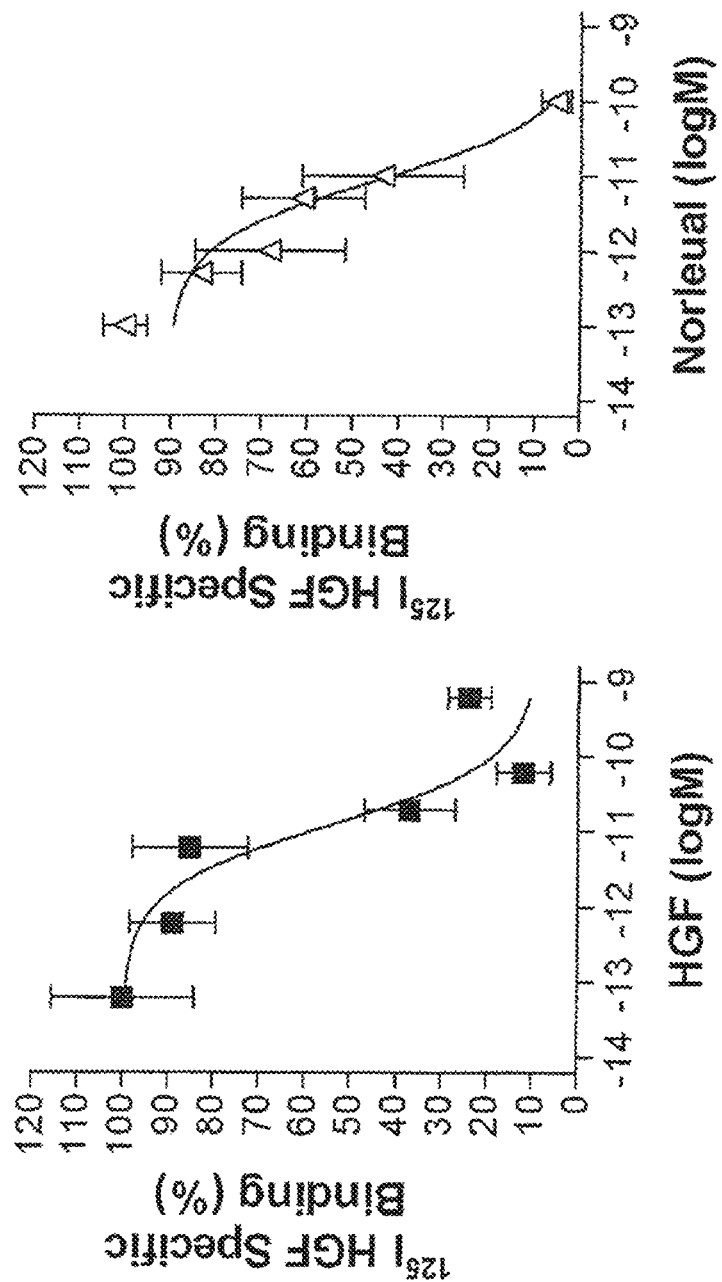
FIG. 2 shows the effects on $^{125}$I-HGF binding to mouse liver membranes of unlabeled HGF (FIG. 2A) and (FIG. 2B) norleual (Compound 2, SEQ ID NO:43). Mouse liver plasma membranes were incubated with 50 μM $^{125}$I-HGF and the indicated concentrations of HGF or Norleual. Results are presented as percent of specific $^{125}$I-HGF binding and error bars indicate +/−standard error of mean (SEM). Competition experiments included quadruplicate data points and each experiment was repeated in triplicate.
Figure 3A:
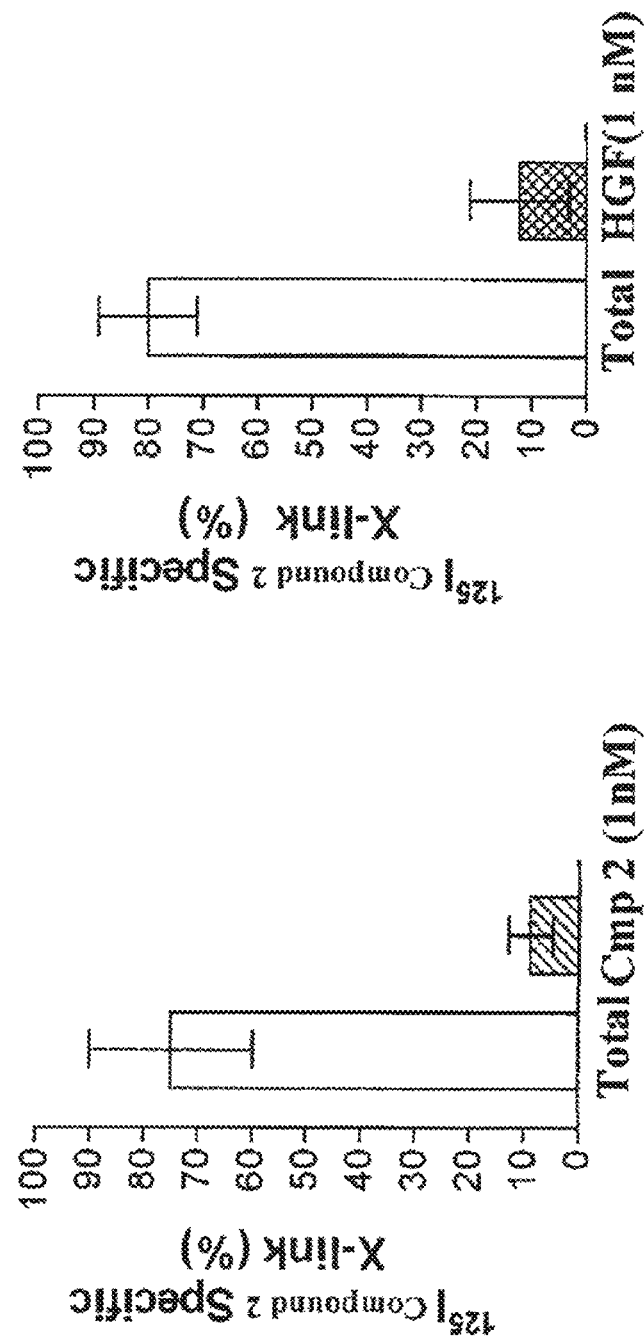
FIG. 3 shows the effects of unlabeled HGF (FIG. 3A, right panel) or unlabeled norleual (FIG. 3A, left panel) on $^{125}$I-norleual (FIG. 3A, Compound 2, SEQ ID NO:43) binding to HEK293 cells, and of unlabeled HGF (FIG. 3B, left panel) or unlabeled norleual (FIG. 3B, right panel) on $^{125}$HGF binding to HEK293 cells.
FIG. 3C: $^{125}$I-Norleual was bound to HEK membranes in the presence or absence of 1.5 nM HGF (n=8) or 1 .mu.M Norleual (n=6). Total binding is reported as percent control (n=10), (*p<0.001). Error bars indicate +/−SD.
FIG. 3D shows the effects of the indicated concentrations of unlabeled Norleual on binding of $^{125}$I-Norleual to HEK293 membranes, with data subject to PRISM® nonlinear regression analysis (GraphPad Software Inc., San Diego, Calif.) showing significantly better data fit for two-site competition model than for one-site model (F=7.335, P=0.0074). IC50 values for Norleual were calculated as 43 pM and 7.4 nM. Error bars indicate SD and data points were performed in duplicate. A repeat experiment showed similar results (F=7.825 and P=0.0023).
Figure 3B:
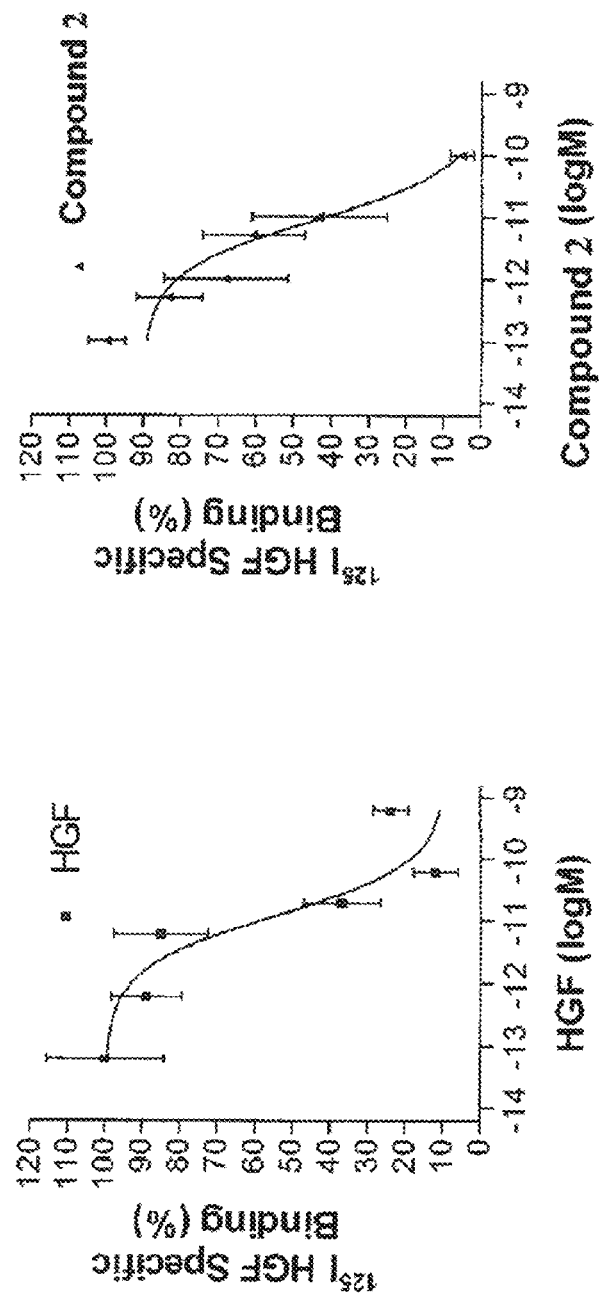
Figure 3C:
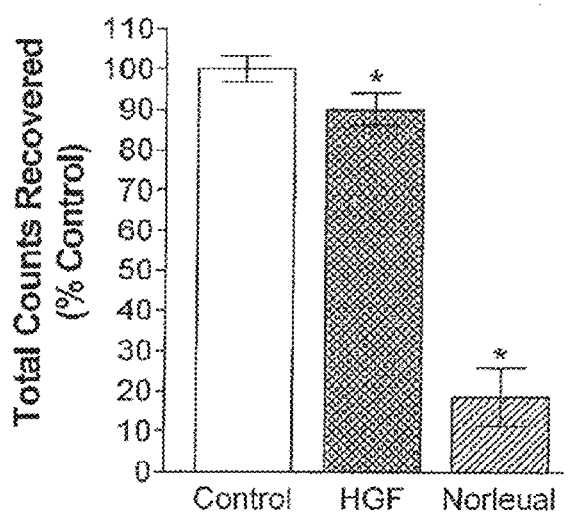
Figure 3D:
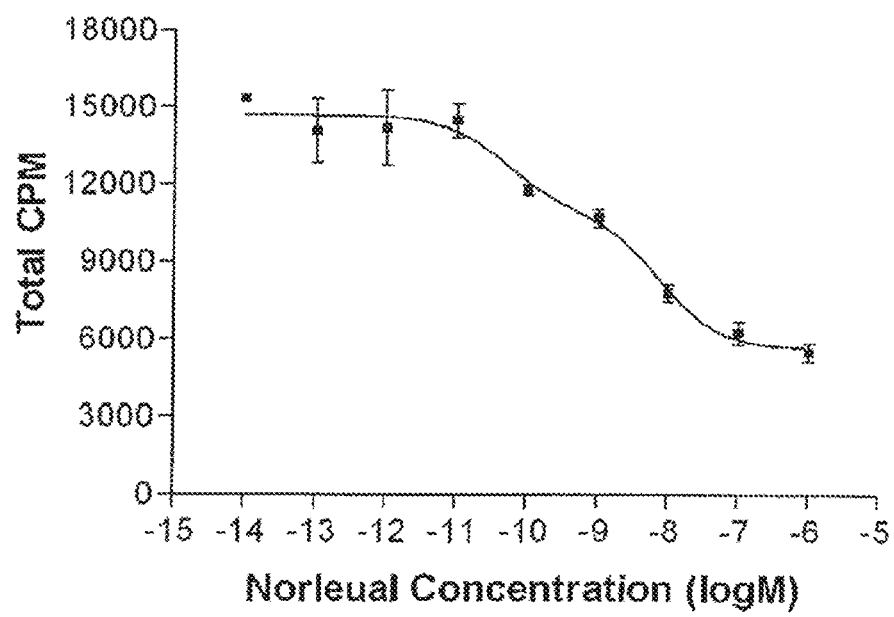

The Angiotensin-Like Factor Norleual Competes with HGF for Binding to the C-Met Receptor This Example shows that the $AT_4$ receptor antagonist, Norleual (Compound 2, SEQ ID NO:43, [Nle-Y-L-Ψ-(CH$_2$—NH$_2$)-H-P-F], Davis et al., 2006 Neuroscience. 137: 1369) competed with HGF for binding to c-Met on cell surfaces and in a cell membrane. Materials and Methods were as described in Example 1. In separate tests of unlabeled competitors, both Norleual and HGF competed with $^{125}$I-HGF for high affinity binding to mouse liver plasma membranes (FIG. 2A, 2B). The $IC_{50}$ values for Norleual and HGF were 3.1±2.1 pM and 29.4±14.7 pM (mean±SEM, n=3), respectively; the latter value was similar to that reported previously (Higuchi et al. 1991 Biochem. Biophys. Res. Commun. 176: 599-607). To further test the hypothesis that Norleual interacted with the c-Met system, $^{125}$I-Norleual was bound to HEK293 cell membranes alone or in the presence of HGF or Norleual. Both ligands competed for $^{125}$I-Norleual specific binding to HEK293 cell membranes, and Norleual also apparently interacted with binding sites on HEK293 membranes that were not shared with HGF (FIGS. 3C and 3D). Together, these findings were consistent with a direct interaction between Norleual and c-Met or HGF.

Whether the interaction of Norleual with the c-Met receptor had functional consequences regarding c-Met signaling was next investigated by determining whether Norleual could alter the phosphorylation status of cellular protein tyrosine phosphate (FIG. 4) and more specifically, of c-Met (i.e., c-Met activation), and also whether Norleual could modulate Gab1 association with c-Met. Human embryonic kidney HEK293 cells were activated by HGF in the presence or absence of Norleual. Solubilized membranes were immunoprecipitated (IP) with an anti-c-Met antibody and immunoblotted (IB) for total c-Met, anti-phospho-tyrosine to detect the activated form of c-Met, and anti-Gab1 to detect c-Met/Gab1 association. FIG. 5A shows that c-Met auto-phosphorylation was induced in a dose-dependent manner by HGF with saturation occurring at 550 pM. Norleual applied alone did not alter c-Met phosphorylation, while Norleual at 20 pM significantly reduced HGF-dependent c-Met and Gab1 phosphorylation (FIG. 5B, 5E, FIG. 6). In addition, Norleual significantly reduced HGF-initiated association between Gab1 and c-Met (FIG. 5C, 5F). To confirm these findings, treated HEK293 lysates were precipitated with anti-Gab1 and blotted for total Gab1 and phospho-Gab1, its activated form. Again, Norleual inhibited HGF-induced Gab1 phosphorylation (FIG. 5D, 5G). Collectively, these data indicated that the $AT_4$ antagonist Norleual (Compound 2, SEQ ID NO:43) markedly attenuated HGF-dependent c-Met activation.

Example 3

Inhibition of HGF-Induced Cell Scattering by an Angiotensin-Like Factor

To explore the physiological significance of the angiotensin-like factor Norleual's ability to depress c-Met signaling, Norleual's effect on HGF induced cell scattering of Madin-Darby canine kidney (MDCK) cells was assessed with the coverslip assay (Miao et al., 2003 J. Cell Biol. 162: 1281-1292). See Example 1 for other Materials and Methods. Norleual inhibited HGF-induced MDCK cell scattering, yielding a response that was similar to controls (FIG. 8A).

Example 4

Anti-Cancer Activity of the Angiotensin-Like Factor Norleual

In this Example, anti-cancer activity of the angiotensin-like factor Norleual (Compound 2, SEQ ID NO:43) was demonstrated. See Example 1 for Materials and Methods. Norleual was applied to HGF treated B16-F10 murine melanoma cells in a scratch wound assay. HGF accelerated the wound closure, however Norleual was able to attenuate HGF stimulated closure six hours after scratch (FIG. 11A).

In addition, molecules associated with proliferation and migration signal transduction in B16-F10 melanoma cells were investigated in the scratch wound assay. HGF alone promoted enhanced phosphorylation of the signal transduction molecules Erk1/2, an effect that was attenuated by the presence of Norleual (FIG. 11B). Specificity of this effect of Norleual for a signal transduction pathway in which Erk1/2 components are present was demonstrated by the observation that Norleual did not affect Akt phosphorylation that was induced by HGF (FIG. 11B). These data show inhibition by Norleual of HGF-induced signaling.

Example 5

Effect of an Angiotensin-Like Factor on Angiogenesis

In this Example, anti-angiogenic activity of the angiotensin-like factor Norleual (Compound 2, SEQ ID NO:43) was demonstrated. See Example 1 for Materials and Methods. Angiogenesis was evaluated with the ex vivo mouse aortic ring assay in the presence and absence of Norleual.

Robust angiogenic sprouts were observed in control rings, while angiogenic growth was significantly attenuated in Norleual-treated aortic rings (FIG. 16A). Because c-Met activation promotes angiogenesis in endothelial cells (Jiang et al., 2005 *Crit. Rev. Oncol. Hematol.* 53: 35), the effect of Norleual on c-Met signaling in endothelial cells was investigated. Norleual inhibited HGF-induced Met/Gab1 association in human umbilical vein endothelial cells (HUVEC) in vitro (FIG. 16B). Together, these observations indicated that inhibition of angiogenesis by Norleual may be the result of attenuation by Norleual of c-Met signaling in endothelial cells.

Example 6

In Vivo Anti-Cancer Activity of the Angiotensin-Like Factor Norleual

In this example, the effect of Norleual on in vivo tumor growth was tested. A role for c-Met signaling in B16-F10 tumor invasion and metastasis has been reported (Ferraro, et al., 2006 *Oncogene.* 25: 3689-3698). Materials and Methods were as described herein including in Example 1. Norleual inhibited primary B16-F0 murine melanoma growth in male C57 mice (FIG. 13A). When the effect of the angiotensin-like factor Norleual was tested on secondary tumor growth using the in vivo pulmonary B16-F10 melanoma metastasis model in mice (Fidler and Nicolson, 1976 *J Natl Cancer Inst.* 57: 1199), striking results were obtained. As shown in FIG. 13, Norleual dramatically inhibited B16-F10 lung metastasis in mice (FIG. 13B, 13C).

Example 7

Effect of Several Angiotensin-Like Factors on Angiogenesis

This Example shows alteration of angiogenesis by angiotensin-like factors as provided herein, in particular, that $Nle^1$-AngIV, an $AT_4$ receptor agonist, augmented the proliferation and migration of human endothelial calls, while NORLEUAL, an $AT_4$ receptor antagonist, inhibited these processes. Materials and methods were as described in this Example and in Example 1.

Disc Angiogenesis Assay. Granulation tissue was experimentally induced by implantating a polyvinyl alcohol foam disc 10 mm in diameter and 2 mm thick (Fajardo et al., 1988). A 2 mm core was removed from the center of each disc, saturated with 50 μg of $Nle^1$-AngIV (SEQ ID NO:41), $Nle^1$-$Leu^3$-$\Psi(CH_2NH_2)^{3-4}$-AngIV, Hexamide, or ethanol (control), air dried, then sealed using a fixative (ELVAX®, DuPont) to allow sustained delivery of the drug treatment into the disc and adjacent tissues. The cores were dried for 30 min, then reinserted into the sponge discs. Impermeable top and bottom covers were prepared by coating 10 mm diameter paper discs with a plexiglass coating, then glued to the top and bottom of the sponge discs, leaving only the rim of the disc available for centripetal cellular penetration. Just prior to implantation, the discs were soaked briefly in sterile saline.

Thirty-two Sprague Dawley female rats (225-275 gr) were used to evaluate four compounds for angiogenic or anti-angiogenic properties using the disc angiogenesis assay. Animals were anesthetized using sodium pentobarbital (40 mg/kg IP). The dorsum was then shaved and aseptically prepped. Each animal received four discs. Animals receiving treated discs were implanted with 2 treated discs and 2 ethanol-soaked control discs. Thus, in a group of 4 animals there were 8 treatment discs, and 8 control discs. These control discs were used to determine whether the ligand had potential systemic effects. Another group of 4 animals received only ethanol-soaked control discs (spontaneous growth controls or SGC discs) for an n=16. However, one SGC was fragmented during processing leaving an n=15.

Four 2 cm cutaneous incisions were made along the dorsum (left thoracic, right thoracolumbar, left thoracolumbar, and right lumbar), and subcutaneous pouches opened in the fascia using blunt dissection. Discs were moistened in sterile saline, inserted deep to the pouch, and the skin closed with sterile surgical staples. Animals were recovered under heat lamps until sternally recumbent, then individually housed for 14 days in an AAALAC accredited facility (water and food ad libitum; 12/12 hour light cycle).

After 14 days the animals were euthanized in a $CO_2$ chamber and the discs were removed. The outer plexiglass covers were discarded and the sponge discs were individually inserted into plastic cassettes, placed in neutral buffered formalin (10%) for 48-72 hours, followed by saturation in 70% ethanol for 24 hours, and then paraffin embedded. Six planar 3 μm sections were cut from each disc and mounted on electrostatic slides (Sigma). Slides were deparaffinized, then hydrated in ethanol of decreasing dilution with water (100%-50%), and then stained with 0.33 mg/ml toluidine blue for 30 sec to permit visualization of the area of the disc penetrated by migrating cells. Three washes with water followed, then dehydration by reversal of the alcohol baths. Finally, the slide was rinsed in Clear Rite 3 and coverslipped. Cellular penetration into the discs was quantified using a digital imaging system (Imaging Research Inc., St. Catharines, Ontario, Canada). The total area of the disc was calculated, as was the area containing stained cells. Data were then reported as total cellular area as a proportion of disc area.

Results. Following staining with toludine blue or Factor VIII, neovascularization was quantitated by densitometry. Results are summarized in FIG. 19. A comparison of SGC discs (n=15) to treatment discs indicated all treatments were anti-angiogenic at the tested doses, p<0.01 in all cases except Nle1-AngIV (SEQ ID NO:41), the lone AT4 receptor agonist. Those compounds exhibiting antagonist activity included Nle-Tyr-Ile-His, Nle-Tyr-Ile-(6)aminohexanoic amide, and NORLEUAL.

Example 8

In Vivo Anti-Cancer Activity of the Angiotensin-Like Factor Norleual

This Example describes Norleual effects in a mouse model of breast cancer in which animals were orthotopically injected with +SA WAZ-2T mouse mammary carcinoma cells ($5 \times 10^3$) into the mammary fat pad of 11-week old female Balb/c mice. The +SA cell line was chosen due to its aggressive nature and ability to form highly vascularized tumors with 100% incidence per injection (Danielson et al., 1986). NORLEUAL (SEQ ID NO:43) was delivered via ELVAX® slow release pellets at doses of 0.3 mg/pellet, 0.03 mg/pellet, and 0.003 mg/pellet, implanted into the mammary glands immediately prior to tumor cell injection. These pellets provided an estimated continuous release of NORLEUAL at doses equivalent to 37.5 μg/kg/day, 3.75 μg/kg/day, and 0.375 μg/kg/day, respectively (based on in vitro release assays of pellets, data not shown). This method of drug administration was consistent with previous reports demonstrating increased efficacy of angiogenic inhibitors delivered on a low-dose, continuous schedule (Kisker, et al., 2001), as opposed to conventional cytotoxic chemotherapy, which is administered in a bolus injection of the maximum tolerated dose. Tumor growth was monitored every 2-3 days, based on caliper measurements of the two longest diameters and calculating tumor volume.

Control tumors typically required a 7 day lag period before a palpable tumor mass arose, a timeframe consistent with previous in vivo studies using this same cell line (Danielson et al., 1986). NORLEUAL treatment, however, increased the delay in onset up to 21 days (0.3 mg/pellet; n=6). In addition, NORLEUAL treatment significantly decreased tumor volume in a dose-dependent manner, with the most effective dose demonstrating 97% inhibition of tumor volume compared to control (control tumor volume: 389.6±107 mm$^3$; 0.3 mg/pellet NORLEUAL-treated tumor volume: 20.2±12 mm$^3$, n=6, P<0.001). NORLEUAL given at 0.03 mg/pellet and 0.003 mg/pellet also significantly reduced tumor volume compared to that of control tumors (70.5±47 mm$^3$, n=6, P<0.007 and 112.7±61 mm$^3$, n=6, P<0.02, respectively). Furthermore, control tumors removed at the conclusion of the experiment were visibly vascularized, while treated tumors were pale in color with a total lack of visible vascularization. Further analysis of tumor vascularization by immunohistochemical staining with Factor VIII antibody confirmed the reduced vascularization of treated tumors compared to that of control tumors, both in the surrounding normal mammary tissue and within the tumor mass (control tumor mean vessel count/high power field 27.8±3 vs. 0.3 mg/pellet NORLEUAL-treated tumor mean vessel count/high power field 3.0±0.9; n=5, P<0.0001).

Example 9

Preparation of Angiotensin-Like Factors

A library of synthetic angiotensin IV receptor ligands was constructed as candidate angiotensin-like factors, by computer modeling and rational drug design approaches. Briefly, acidic, basic, aromatic or branch chain amino acids were systematically substituted for each position in an angiotensin IV polypeptide. Additionally, each constituent amino acid residue was either deleted or converted to a d-amino acid form, and peptide bond isosteres were constructed with several amino acids. Putative agonist and antagonist molecules were modeled to yield a pharmacophore structure, including comparison with known molecules at ten atomic centers.

Figure 4A:
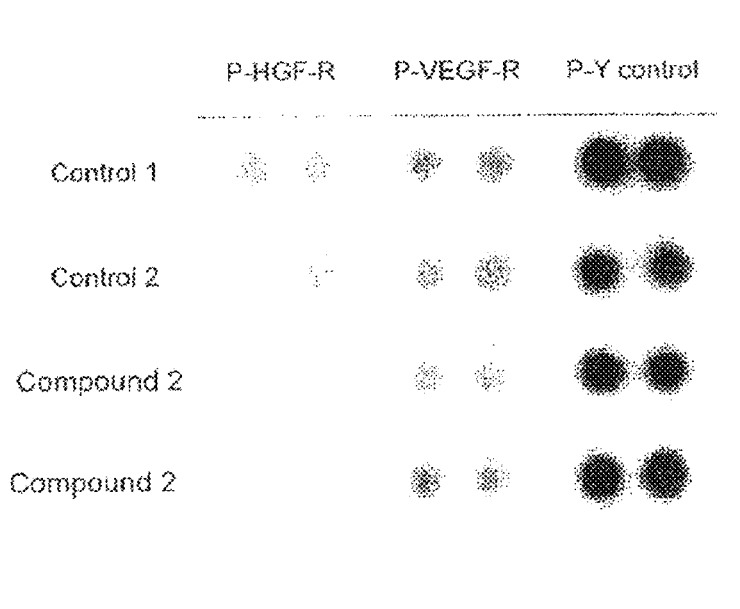
FIG. 4 shows the effects of Norleual (Compound 2, SEQ ID NO:43) on receptor protein tyrosine phosphorylation in a tyrosine kinase receptor protein array (FIG. 4A), with quantification of relative receptor protein tyrosine phosphorylation shown in FIG. 4B: P-HGF-R control, protein from hepatocyte growth factor receptor control; P-HGF-R Compound 2, protein from hepatocyte growth factor receptor treated with Compound 2; P-VEGF1-R control, protein from VEGF1 receptor control; P-VEGF1-R Compound 2, protein from VEGF1 receptor treated with Compound 2.
Figure 4B:
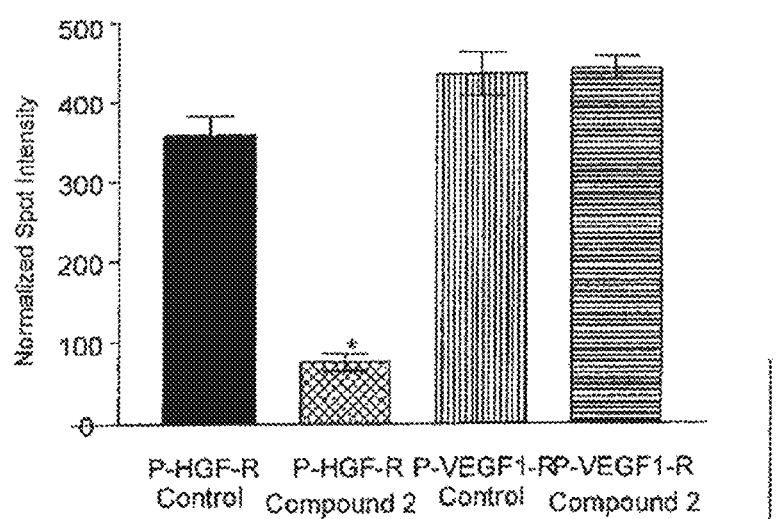

Screening of a ligand for its ability to inhibit c-Met receptor phosphorylation was tested by tyrosine kinase receptor protein array. Briefly, human umbilical vein endothelial cells (HUVECs) grown to confluence were treated for 5 minutes with COMPOUND 2 (SEQ ID NO:43). Cells were then lysed and total protein collected. As illustrated in FIGS. 4A and 4B, the angiotensin ligand inhibited c-Met phosphorylation when compared with controls.

Example 10

Angiotensin-Like Factor Competes with HGF for Binding to C-Met Receptor in Cell Membranes The ability of COMPOUND 2 (SEQ ID NO:43, Norleual) acting as a ligand to compete with hepatocyte growth factor for binding to the c-Met receptor was tested in human embryonic kidney cells 293 (HEK 293). See Example 1 for materials and methods.

Briefly, COMPOUND 2 was iodinated with $^{125}$I and bound and cross-linked to HEK cell membranes with or without 1 nM COMPOUND 2 or 1 nM hepatocyte growth factor. Following solubilization and separation of free label by molecular sieving, total radioactive counts were determined. The results showed that hepatocyte growth factor blocked $^{125}$I-COMPOUND 2 binding to HEK cells, as presented in FIG. 3A. The ability of the ligand COMPOUND 2 to compete with hepatocyte growth factor binding to the c-Met receptor was also tested using mouse liver plasma membranes and intact HEK293 cells. Briefly, mouse liver was homogenized and incubated with $^{125}$I-HGF with various concentrations of HGF or COMPOUND 2. Membranes were pelleted and unbound label was removed by washing, and total radioactive counts were determined. Next, HEK293 cell membranes were cross-linked with $^{125}$I-HGF with unlabeled HGF or COMPOUND 2. Results indicated COMPOUND 2 is a competitive inhibitor of HGF binding to the c-Met receptor, as illustrated in FIG. 3B. The $K_D$ for HGF was approximately 29 pM, while the $K_D$ for COMPOUND 2 was approximately 3 pM.

Example 11

Angiotensin-Like Factor Alters Gene Expression in Endothelial Cells

Angiotensin-like factors as candidate c-Met receptor ligands were tested for the ability to modulate expression of extracellular matrix-related proteins in human umbilical vein endothelial cells (HUVECs) by gene microarray. Briefly, HUVECs were treated for 8 days in the presence or absence of test compounds at a concentration of 1 pM; Norleual (Compound 2, SEQ ID NO:43) was used as an exemplary angiotensin-like factor. RNA was harvested and transcriptional activities of 96 extracellular matrix related genes were assessed using gene microarrays. Gene expression levels that differed from the levels in control samples by at least two fold for cells treated with Compound 2 included: CD44, catenin, catenin β, catenin δ1, MMP-1, PAI-1, thrombospondin 1, and integrin α-2.

Example 12

Norleual Alteration of Angiogenesis-Related Gene Expression

Angiotensin-like factor Norleual (COMPOUND 2) was tested for its ability to modulate angiogenic genes in murine mammary tumors. Briefly, Balb/c mice grafted with +SA murine mammary cancer cells were treated with Compound 2. After 28 days of intraperitoneal administration via an osmotic pump (at a dose of 1 mg/kg/day), primary tumors were harvested and RNA was collected. Transcriptional activities of 96 angiogenesis-related genes were assessed using gene microarrays. Genes that differed from control by at least five-fold included: Adamts 1, CD36, Connective tissue growth factor, PECAM 1, Cxcl 4, restin, Ccl 2, TNF-α, VEGF-α, and VEGF-β.

Example 13

Angiotensin-Like Factor Alteration of Cell Scattering

The ability of an angiotensin-like factor, Norleual (COMPOUND 2), to inhibit hepatocyte growth factor-dependent functions, including proliferation, cell scattering, and c-Met mediated collagen I invasion in Madin-Darby canine kidney (MDCK) cells was tested using methodologies described in Example 1. Briefly, MDCK cells were grown to confluence, and COMPOUND 2 and/or heptocyte growth factor were added as appropriate. For the proliferation assay, hepatocyte growth factor was used at 10 ng/ml, and COMPOUND 2 was used at $10^{-6}$M, $10^{-8}$M, $10^{-10}$ M, $10^{-12}$M, or $10^{-14}$M. For the scattering assay, hepatocyte growth factor was used at 20 ng/ml, and COMPOUND 2 was used at $10^{-10}$ M. For the collagen assay, hepatocyte growth factor was used at 20 ng/ml, and COMPOUND 2 was used at $10^{-10}$M, $10^{-11}$M, or $10^{-12}$M. For all assays, cells were fixed in methanol and stained with Diff-Quick Wright-Giemsa (Dade-Behring). As illustrated in representative FIG. 7, COMPOUND 2 inhibited hepatocyte growth factor-dependent cell scattering. Compound 2 also inhibited cellular proliferation, and c-Met mediated collagen I invasion by MDCK cells.

Example 14

In Vivo Anti-Cancer Activity of Angiotensin-Like Factors

This example shows anti-cancer activity of several angiotensin-like factors in the C57BL/6 murine model of in vivo metastasis using B16-F10 melanoma cells, as also described in Examples 1 and 6. Briefly, ALZET® osmotic pumps (Durect Corp., Cupertino, Calif.) containing indicated angiotensin-like factor or vehicle control were surgically implanted into the peritoneal cavity of C57BL/6 mice (according to the pump manufacturer's surgical implantation protocol). The following day, mice were inoculated with 400,000 B16-F10 cells in 200 μl PBS by tail vein injection. At fourteen days, mice were killed and lungs were dissected and weighed. Average age-matched control lung weights were subtracted from lung weights to determine tumor burden and normalized to control values. Results are shown in FIG. 20, wherein animals received one of the following angiotensin-like factors via an intrapertoneal osmotic pump implanted the day before B16F10 tail vein inoculation: Control group, none (FIG. 20, "Control"); Group A, D-Nle-Cys-Ile-6-aminohexanoic amide [SEQ ID NO:142] (FIG. 20 "A"); Group B, Norleual [SEQ ID NO:43] (FIG. 20, "B"); Group C, D-Nle-Tyr-Ile-6-aminohexanoic amide [SEQ ID NO:143] (FIG. 20, "C"); Group D, Lys-Asp-Tyr-Ile-Arg-Asn-Cys [SEQ ID NO:82] (FIG. 20, "D").

Example 15

Angiotensin-Like Factor Affects Mammalian Body Weight

This example shows the effects of the angiotensin-like factor Norleual (Nle-Tyr-Leu-Ψ-His-Pro-Phe) [SEQ ID NO:43] on body weight in CB57/BL6 mice. Twenty-four five-week old CB57BL/6 male mice were equally and randomly assigned to two groups. One group was assigned as control and the other treated. Treated mice were administered intermuscular (IM) injections of Norleual at 21 μg/kg/day, (40 μl injectable volume) every 48 hours for the duration of one hundred and one days. Injection sites were alternated between left and right gluteus medius. BD Ultra-Fine 3/10 cc insulin syringes were used as delivery apparatus. Mice were housed two per cage and had unlimited access to food and water. Mice were monitored daily for signs of morbidity. Mice were also weighed on a weekly basis, C57/BL6 mice were treated either with vehicle control or with Norleual chronically for 101 days.

The average weights for each group were plotted against time, as shown in FIG. 21 (control weights (diamonds) and Norleual-treated weights (squares); error bars indicate +/−SEM and n=11. Upon visual inspection, Norleual-treated animals were visibly less bulky than control animals.

To assess body composition of the mice, the Comparative Orthopedic Research Laboratory at the Washington State University Veterinary School was utilized. A Hologic QDR4500A fan beam dual-energy X-ray absorptiometer (DXA, Hologic Inc., Bedford, Mass.) was used to assess the lean body mass (muscle), fat, and bone composition of each mouse on day one hundred one of the experiment. Mice were sacrificed and DXA scans were performed. Due to the volume limitations of the DXA instrument and to permit time for gross pathology, half of the mice were sacrificed and analyzed on day 101. The remaining mice were sacrificed and analyzed 22 hours later. Control and treated mice were split evenly among the two sacrifice episodes. Data were collected and the control group was compared to the Norleual treated group by two-tailed student's t-tests using InStat software (GraphPad, San Diego, Calif.). Figures were created using GraphPad Prism software.

Results are shown in FIG. 22. FIG. 22A shows a comparison of mouse weights determined by scale measurement and DXA measurement on day 101. (FIG. 22A, Left panel), scale measured weights of Norleual treated mice ("T") were significantly lower than control mice ("C") (p=0.0130). (FIG. 22A, Right panel), DXA measured mass of Norleual mice ("T") was significantly lower than that of control mice ("C") (p=0.0146). FIG. 22B shows the DXA measured area of Norleual-treated mice ("Norleual") was significantly lower than that of control mice ("Control") (p=0.023). FIG. 22C shows the DXA measured bone mineral density was not statistically significant between Norleual-treated mice ("Norleual") and control mice ("Control"). FIG. 22D shows the percent fat of Norleual-treated mice ("Norleual") was significantly lower than that of control mice ("Control") when measured by DXA (p<0.0001). FIG. 22E shows the lean body mass+bone mineral content (BMC) of Norleual-treated mice (hatched) was not significantly different than control mice (white) when measured by DXA (p=0.18). All error bars in FIG. 22 indicate SEM and n=11.

Gross pathology and microscopic pathological evaluation on autopsy tissue were performed in blinded fashion on animals following sacrifice, with attention to multiple organs. A marked reduction in the distribution of lipid vacuoles in the liver of Norleual-treated mice relative to control animals was observed.

Example 16

Figure 23A:
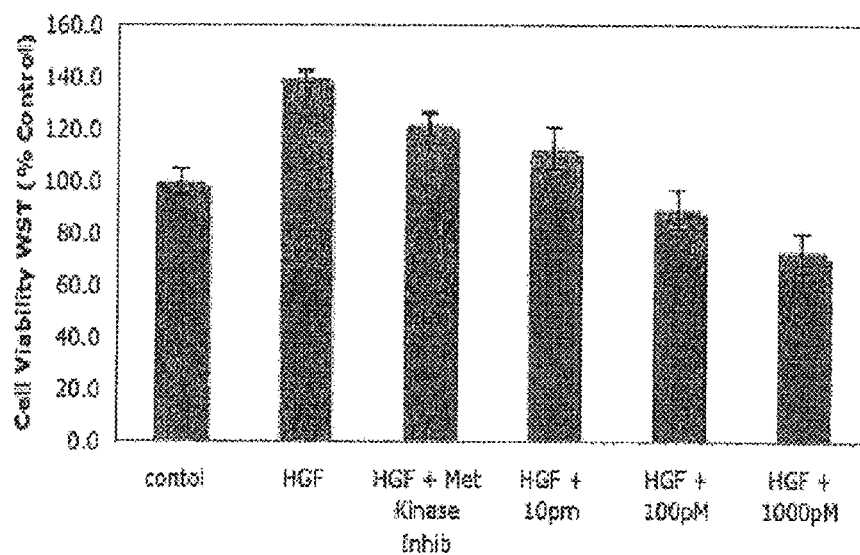
Figure 23B:
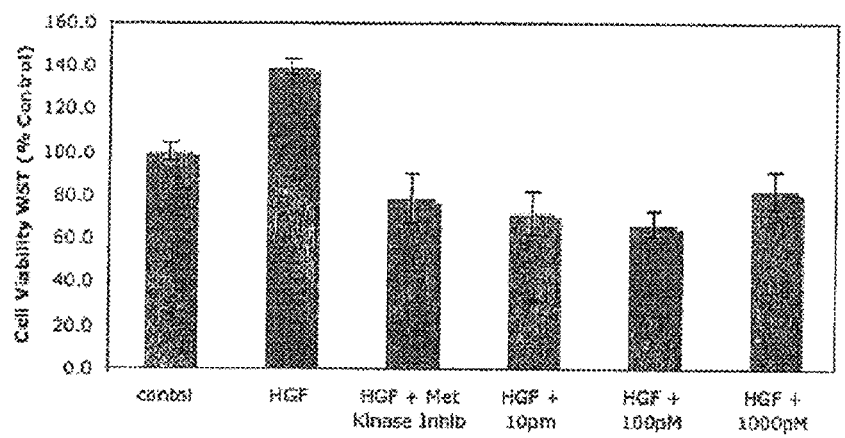

Effect of Angiotensin-Like Factors on HGF-Induced Enhanced Endothelial Cell Viability This example shows the effect of angiotensin-like factors on enhanced endothelial cell viability induced by HGF via the c-Met receptor, an in vitro model of relevance to angiogenesis. Human Umbilical Vein Endothelial Cells (HUVEC) were seeded at $2 \times 10^3$ cells/well in 96-well plates in EGM-2 media (Lonza Biosciences, Basel, Switzerland). Cells were allowed to attach overnight. The following day, media was replaced with EBM-2 media (Lonza) supplemented with 1% FBS only ("control"), or also containing HGF (25 ng/ml) with or without 10-1000 µM of the angiotensin-like factor D-Nle-Cys-Ile-6-aminohexanoic amide [SEQ ID NO:142] or Lys-Asp-Tyr-Ile-Arg-Asn-Cys [SEQ ID NO:82]. Additional control groups received HGF and a c-Met kinase inhibitor. After 24 hours incubation in a 37° C., 5% $CO_2$ cell culture incubator (Binder Inc., Great River, N.Y.), WST reagent (Quick Cell Proliferation Assay Kit II, Biovision, Mountain View, Calif.) was added to each well for determination of mitochondrial dehydrogenase activity as a quantitative indicator of cell viability according to the supplier's instructions. After four hours, absorbance at 400 nm was measured (BioTek SYNERGY™ plate reader, BioTek Instruments, Winooski, Vt.). Blank well subtraction preceded normalization to obtain average control absorbance. The results are shown in FIG. 23 for Lys-Asp-Tyr-Ile-Arg-Asn-Cys [SEQ ID NO:82] (FIG. 23A) and D-Nle-Cys-Ile-6-aminohexanoic amide (FIG. 23B); error bars indicate +/−SEM.

From the foregoing it will be appreciated that, although specific embodiments of the invention have been described herein for purposes of illustration, various modifications may be made without deviating from the spirit and scope of the invention. Accordingly, the invention is not limited except as by the appended claims.

REFERENCES

Bai L, Lennon D P, Caplan A I, Dechant A, Hecker J, Kranso J, Zaremba A, Miller R H. (2012) Hepatocyte growth factor mediates mesenchymal stem cell-induced recovery in multiple sclerosis models. *Nat. Neurosci.* May 20. [Epub ahead of print]

Dikmen S S, Corrigan J D, Levin H S, Machamer J, Stiers W, Weisskopf M G (2009) Cognitive outcome following traumatic brain injury. *J Head Trauma Rehabil.* 24:430-438.

Fafalios A, Ma J, Tan X, Stoops J, Luo J, Defrances M C, Zarnegar R. (2011) A hepatocyte growth factor receptor (Met)-insulin receptor hybrid governs hepatic glucose metabolism. *Nat. Med.* 17:1577-84.

Gao X, Deng P, Xu Z C, Chen J (2011) Moderate traumatic brain injury causes acute dendritic and synaptic degeneration in the hippocampal dentate gyrus. *PLoS One;* 6:e24566.

Ieraci A, Formi P E, Ponzetto C. Viable hypomorphic signaling mutant of the Met receptor reveals a role for hepatocyte growth factor in postnatal cerebellar development. (2002) *Proc Natl Acad Sci USA.* 99:15200-5.

Kane M J, Angoa-Perez M, Briggs D I, Viano D C, Kreipke C W, Kuhn D M (2011). A mouse model of human repetitive mild traumatic brain injury. *J Neurosci Methods.* September 12. [Epub ahead of print]

Kaplan G B, Vasterling J J, Vedak P C (2010) Brain-derived neurotrophic factor in traumatic brain injury, post-traumatic stress disorder, and their comorbid conditions: role in pathogenesis and treatment. *Behav Pharmacol.* 21:427-437.

Kato N, Nakanishi K, Nemoto K. Efficacy of HGF gene transfer for various nervous injuries and disorders. (2009) *Cent Nerv Syst Agents Med. Chem.* 9:300-6.

Kitamura K, Fujiyoshi K, Yamane J, Toyota F, Hikishima K, Nomura T, Funakoshi H, Nakamura T, Aoki M, Toyama Y, Okano H, Nakamura M. (2011) Human hepatocyte growth factor promotes functional recovery in primates after spinal cord injury. *PLoS One.* 6:e27706.

Koike H, Ishida A, Shimamura M, Mizuno S, Nakamura T, Ogihara T, Kaneda Y, Morishita R. Prevention of onset of Parkinson's disease by in vivo gene transfer of human hepatocyte growth factor in rodent model: a model of gene therapy for Parkinson's disease. (2006) *Gen Ther* 13:1639-1644.

Lan F, Xu J, Zhang X, Wong V W, Li X, Lu A, Lu W, Shen L, Li L. Hepatocyte growth factor promotes proliferation and migration in immortalized progenitor cells. (2008) *Neuroreport.* 19:765-9.

Lim C S and Walikonis R S. Hepatocyte growth factor and c-Met promote dendritic maturation during hippocampal neuron differentiation via the Akt pathway. (2008) *Cell Signal.* 20: 825-35.

Maina F and Klein R. Hepatocyte growth factor, a versatile signal for developing neurons. (1999) *Nat Neurosci* 2: 213-217.

Masel B E, DeWitt D S (2010) Traumatic brain injury: a disease process, not an event. *J Neurotrauma.* 27:1529-1540.

Nakamura T, Sakai K, Nakamura T, Matsumoto K. Hepatocyte growth factor twenty years on: Much more than a growth factor. (2011) *Journal of Gastroenterology and Hepatology* 26 Suppl. 1; 188-202

Nicoleau C, Benzakour O, Agasse F, Thiriet N, Petit J, Prestoz L, Roger M, Jaber M, Coronas V. Endogenous hepatocyte growth factor is a niche signal for subventricular zone neural stem cell amplification and self-renewal. (2009) *Stem Cells.* 27:408-19.

Okie S (2005) Traumatic brain injury in the war zone. *N Engl J Med.* 352:2043-2047.

Rangasamy S B, Soderstrom K, Bakay R A E and, Kordower J H. Neurotrophic factor therapy for Parkinson's disease. (2010) *Progress in Brain Research* 184: 237-264.

Richardson R M, Singh A, Sun D, Fillmore H L, Dietrich D W 3rd, Bullock M R (2010) Stem cell biology in traumatic brain injury: effects of injury and strategies for repair. *J. Neurosurg.* 112:1125-1138.

Santos O F, Moura L A, Rosen E M, Nigam S K. Modulation of HGF-induced tubulogenesis and branching by multiple phosphorylation mechanisms. (1993) *Dev Biol.* 160:293-302.

Schwarzbach E, Bonislawski D P, Xiong G, Cohen A S (2006) Mechanisms underlying the inability to induce area CA1 LTP in the mouse after traumatic brain injury. *Hippocampus.* 16:541-550.

Zhang B L, Chen X, Tan T, Yang Z, Carlos D, Jiang R C, Zhang J N (2011) Traumatic brain injury impairs synaptic plasticity in hippocampus in rats. Chin Med J (Engl). 124: 740-745.

Zhang B, Chen, Lin Y, Tan T, Yang Z, Dayao C, Liu L, Jiang R, Zhang J (2011) Impairment of synaptic plasticity in hippocampus is excerbated by methylprednisone in rat model of traumatic brain injury. Brain Res.; 1382:165-172.

We claim:

1. A method for treating angiogenesis or obesity in a subject in need thereof, comprising administering to the subject a therapeutically effective amount of a pharmaceutical composition comprising an isolated angiotensin-like factor, said angiotensin-like factor being selected from the group consisting of:
   (a) a polypeptide of no more than 20, 19, 18, 17, 16, 15, 14, 13, 12, 11, 10, 9, 8, 7, 6, 5, 4 or 3 amino acids, or a peptidomimetic thereof, of general formula I: N-$X_1$-$X_2$-$X_3$-C [I] wherein: N is an amino terminus of the peptide or peptidomimetic and consists of 0, 1, 2, 3, 4, 5, 6, 7, 8, 9, 10, 11, 12, 13, 14, 15, 16 or 17 amino acids that are independently selected from natural and non-natural amino acids, C is a carboxy terminus of the peptide or peptidomimetic and consists of 0, 1, 2, 3, 4, 5, 6, 7, 8, 9, 10, 11, 12, 13, 14, 15, 16 or 17 amino acids that are independently selected from natural and non-natural amino acids, $X_1$ is phenylalanine, tryptophan or tyrosine, $X_2$ is isoleucine, leucine, alanine, valine, phenylalanine, proline, methionine or tryptophan, and $X_3$ is lysine, arginine or histidine;
   (b) a polypeptide of no more than 20, 19, 18, 17, 16, 15, 14, 13, 12, 11, 10, 9, 8, 7, 6, 5, 4 or 3 amino acids, or a peptidomimetic thereof, of general formula I: N-$X_1$-$X_2$-$X_3$-C [I] wherein: N is an amino terminus of the peptide or peptidomimetic and consists of 0, 1, 2, 3, 4, 5, 6, 7, 8, 9, 10, 11, 12, 13, 14, 15, 16 or 17 amino acids that are independently selected from natural and non-natural amino acids, C is a carboxy terminus of the peptide or peptidomimetic and consists of 0, 1, 2, 3, 4, 5, 6, 7, 8, 9, 10, 11, 12, 13, 14, 15, 16 or 17 amino acids that are independently selected from natural and non-natural amino acids, $X_1$ is a natural or non-natural amino acid having an aromatic side chain, $X_2$ is a natural or non-natural amino acid having a hydrophobic side chain, and $X_3$ is a natural or non-natural amino acid having a basic side chain;
   (c) a polypeptide of no more than 20, 19, 18, 17, 16, 15, 14, 13, 12, 11, 10, 9, 8, 7, 6, 5, 4 or 3 amino acids, or a peptidomimetic thereof, said polypeptide comprising (i) a tripeptide having an amino acid sequence that is selected from: Lys-Asp-Tyr, Leu-Asp-Tyr, Asp-Tyr-Ile, Tyr-Ile-Arg, Ile-Arg-Asn, and Arg-Asn-Cys, and (ii) at least one of an amino terminus and a carboxy terminus, each of said amino terminus and said carboxy terminus consisting of 0, 1, 2, 3, 4, 5, 6, 7, 8, 9, 10, 11, 12, 13, 14, 15, 16 or 17 amino acids that are independently selected from natural and non-natural amino acids;
   (d) the polypeptide or peptidomimetic of (a) which comprises the amino acid sequence Nle-Tyr-Leu-Ψ-His-Pro-Phe as set forth in SEQ ID NO:43, wherein Ψ consists of a reduced peptide bond of formula II: —$CH_2$—$NH_2$— [II]; and
   (e) the polypeptide or peptidomimetic of (b) which comprises at least one amino acid sequence selected from SEQ ID NOS: 9, 25, 33, 41, 42, 45-50, 52-80 and 81.

2. A method for treating angiogenesis or obesity in a subject in need thereof, comprising administering to the subject a therapeutically effective amount of a pharmaceutical composition comprising an isolated angiotensin-like factor that inhibits binding of a native HGF hinge region polypeptide to a cell surface c-Met receptor, said native HGF hinge region polypeptide comprising the amino acid sequence Lys-Asp-Tyr-Ile-Arg-Asn-Cys [SEQ ID NO:82], said angiotensin-like factor being selected from the group consisting of:
   (a) a polypeptide of 15, 14, 13, 12, 11, 10, 9, 8, 7, 6, 5, 4, 3 or 2 amino acids, or a peptidomimetic thereof, said polypeptide comprising a peptide having at least one amino acid sequence that is selected from: Lys-Asp, Asp-Tyr, Tyr-Ile, Ile-Arg, Arg-Asn, Asn-Cys, Lys-Asp-Tyr, Asp-Tyr-Ile, Tyr-Ile-Arg, Ile-Arg-Asn, Arg-Asn-Cys, Lys-Asp-Tyr-Ile [SEQ ID NO: 86], Asp-Tyr-Ile-Arg [SEQ ID NO: 87], Tyr-Ile-Arg-Asn [SEQ ID NO: 88], Ile-Arg-Asn-Cys [SEQ ID NO: 89], Lys-Asp-Tyr-Ile-Arg [SEQ ID NO: 90], Asp-Tyr-Ile-Arg-Asn [SEQ ID NO: 91], Tyr-Ile-Arg-Asn-Cys [SEQ ID NO: 92], Lys-Asp-Tyr-Ile-Arg-Asn [SEQ ID NO: 93], Asp-Tyr-Ile-Arg-Asn-Cys [SEQ ID NO: 94], Lys-Asp-Tyr-Ile-Arg-Asn-Cys [SEQ ID NO:82], Gly-Asp-Tyr-Ile-Arg-Asn-Cys [SEQ ID NO: 95], Lys-Gly-Tyr-Ile-Arg-Asn-Cys [SEQ ID NO: 96], Lys-Asp-Gly-Ile-Arg-Asn-Cys [SEQ ID NO: 97], Lys-Asp-Tyr-Gly-Arg-Asn-Cys [SEQ ID NO: 98], Lys-Asp-Tyr-Ile-Gly-Asn-Cys [SEQ ID NO: 99], Lys-Asp-Tyr-Ile-Arg-Gly-Cys [SEQ ID NO: 100] Lys-Asp-Tyr-Ile-Arg-Asn-Gly [SEQ ID NO: 101], (D)-Lys-Asp-Tyr-Ile-Arg-Asn-Cys [SEQ ID NO: 102], Lys-(D)-Asp-Tyr-Ile-Arg-Asn-Cys [SEQ ID NO: 103], Lys-Asp-(D)-Tyr-Ile-Arg-Asn-Cys [SEQ ID NO: 104], Lys-Asp-Tyr-(D)-Ile-Arg-Asn-Cys [SEQ ID NO: 105], Lys-Asp-Tyr-Ile-(D)-Arg-Asn-Cys [SEQ ID NO: 106], Lys-Asp-Tyr-Ile-Arg-(D)-Asn-Cys [SEQ ID NO: 107], and Lys-Asp-Tyr-Ile-Arg-Asn-(D)-Cys [SEQ ID NO: 108], (b) the polypeptide or peptidomimetic thereof of (a) wherein the peptidomimetic of said polypeptide comprises 1, 2, 3, 4, 5 or 6 reduced peptide bonds, each of said peptide bonds having the formula $CH_2$—$NH_2$+, (c) the polypeptide or peptidomimetic thereof of (b) wherein the peptidomimetic is selected from: Lys-Ψ-Asp-Tyr-Ile-Arg-Asn-Cys [SEQ ID NO: 109], Lys-Asp-Ψ-Tyr-Ile-Arg-Asn-Cys [SEQ ID NO: 110], Lys-Asp-Tyr-Ψ-Ile-Arg-Asn-Cys [SEQ ID NO: 111], Lys-Asp-Tyr-Ile-Ψ-Arg-Asn-Cys [SEQ ID NO: 112], Lys-Asp-Tyr-Ile-Arg-Ψ-Asn-Cys [SEQ ID NO: 113], Lys-Asp-Tyr-Ile-Arg-Asn-Ψ-Cys [SEQ ID NO: 114], Lys-Ψ-Asp-Ψ-Tyr-Ile-Arg-Asn-Cys [SEQ ID NO: 115], Lys-Ψ-Asp-Tyr-Ψ-Ile-Arg-Asn-Cys [SEQ ID NO: 116], Lys-Ψ-Asp-Tyr-Ile-Ψ-Arg-Asn-Cys [SEQ ID NO: 117], Lys-Ψ-Asp-Tyr-Ile-Arg-Ψ-Asn-Cys [SEQ ID NO: 118], Lys-Ψ-Asp-Tyr-Ile-Arg-Asn-Ψ-Cys [SEQ ID NO: 119], Lys-Asp-Ψ-Tyr-Ψ-Ile-Arg-Asn-Cys [SEQ ID NO: 120], Lys-Asp-Ψ-Tyr-Ile-Ψ-Arg-Asn-Cys [SEQ ID NO: 121], Lys-Asp-Ψ-Tyr-Ile-Arg-Ψ-Asn-Cys [SEQ ID NO: 122], Lys-Asp-Ψ-Tyr-Ile-Arg-Asn-Ψ-Cys [SEQ ID NO: 123], Lys-Asp-Tyr-Ψ-Ile-Ψ-Arg-Asn-Cys [SEQ ID NO: 124], Lys-Asp-Tyr-Ψ-Ile-Arg-Ψ-Asn-Cys [SEQ ID NO: 125], Lys-Asp-Tyr-Ψ-Ile-Arg-Asn-Ψ-Cys [SEQ ID NO: 126], Lys-Asp-Tyr-Ile-Ψ-Arg-Ψ-Asn-Cys [SEQ ID NO: 127], Lys-Asp-Tyr-Ile-Ψ-Arg-Asn-Ψ-Cys [SEQ ID NO: 128], and Lys-Asp-Tyr-Ile-Arg-Ψ-Asn-Ψ-Cys [SEQ ID NO: 129], wherein Ψ is a peptide bond having the formula $CH_2$—$NH_2$+, and (d) a polypeptide of 15, 14, 13, 12, 11, 10, 9, 8, 7, 6, 5, 4, 3 or 2 amino acids, or a peptidomimetic thereof, of general formula III: $N-X_1-X_2-X_3-X_4-X_5-X_6-X_7-C$ [SEQ ID NO: 130] [III] wherein: N is an amino terminus of the peptide or peptidomimetic and consists of 0, 1, 2, 3, 4, 5, 6, 7, 8, 9, 10, 11, 12, or 13 amino acids that are independently selected from natural and non-natural amino acids, C is a carboxy terminus of the peptide or peptidomimetic and consists of 0, 1, 2, 3, 4, 5, 6, 7, 8, 9, 10, 11, 12, or 13 amino acids that are independently selected from natural and non-natural amino acids, $X_1$ is nothing, Lys, Arg, His, Norleucine or hexanoic acid, $X_2$ is nothing, Asp or Glu, $X_3$ is nothing, Tyr, Phe or homo-Phe, $X_4$ is nothing, Ile, Leu, Val, Phe, Met or Norleucine, $X_5$ is nothing, Arg, Lys or His, $X_6$ is nothing, Asn or Gln, and $X_7$ is nothing, Cys or Cys-amide.

3. The method of claim 1, wherein said isolated angiotensin-like factor is not Nle-Tyr-Leu-Ψ-His-Pro-Phe (Norleual) or Nle-Tyr-Ile-His-Pro-Phe.

4. The method of claim 2, wherein said isolated angiotensin-like factor is not Nle-Tyr-Leu-Ψ-His-Pro-Phe (Norleual).

5. The method of claim 1 wherein said subject is treated for angiogenesis.

6. The method of claim 1 wherein said subject is treated for obesity.

7. The method of claim 2 wherein said subject is treated for angiogenesis.

8. The method of claim 2 wherein said subject is treated for obesity.

* * * * *